(12) United States Patent
Koo et al.

(10) Patent No.: US 10,377,740 B2
(45) Date of Patent: Aug. 13, 2019

(54) HETEROCYCLIC COMPOUND AND ORGANIC LIGHT EMITTING ELEMENT COMPRISING SAME

(71) Applicant: LG Chem, Ltd., Seoul (KR)

(72) Inventors: Kichul Koo, Daejeon (KR); Jungi Jang, Daejeon (KR); Dong Uk Heo, Daejeon (KR); Miyeon Han, Daejeon (KR); Min Woo Jung, Daejeon (KR)

(73) Assignee: LG Chem, Ltd. (KR)

( * ) Notice: Subject to any disclaimer, the term of this patent is extended or adjusted under 35 U.S.C. 154(b) by 22 days.

(21) Appl. No.: 15/556,731

(22) PCT Filed: Sep. 13, 2016

(86) PCT No.: PCT/KR2016/010350
§ 371 (c)(1),
(2) Date: Sep. 8, 2017

(87) PCT Pub. No.: WO2017/048060
PCT Pub. Date: Mar. 23, 2017

(65) Prior Publication Data
US 2018/0051003 A1    Feb. 22, 2018

(30) Foreign Application Priority Data

Sep. 15, 2015  (KR) .................... 10-2015-0130356
Jul. 15, 2016  (KR) .................... 10-2016-0090117

(51) Int. Cl.
*C07D 401/10* (2006.01)
*C07D 403/10* (2006.01)
*C07D 401/14* (2006.01)
*C09K 11/06* (2006.01)
*H01L 51/50* (2006.01)
(Continued)

(52) U.S. Cl.
CPC .......... *C07D 401/10* (2013.01); *C07C 13/567* (2013.01); *C07D 401/14* (2013.01); *C07D 403/10* (2013.01); *C09K 11/06* (2013.01); *H01L 51/0052* (2013.01); *H01L 51/0067* (2013.01); *H01L 51/50* (2013.01); *H01L 51/506* (2013.01);
(Continued)

(58) Field of Classification Search
None
See application file for complete search history.

(56) References Cited

U.S. PATENT DOCUMENTS 8,158,275 B2    4/2012   Ie et al.
2013/0049581 A1  2/2013   Nishide et al.
(Continued)

FOREIGN PATENT DOCUMENTS

CN    104513223 A    4/2015
CN    104829599 A    8/2015
(Continued)

OTHER PUBLICATIONS

Machine English translation of Huang et al. (CN 104829599 A). Dec. 6, 2018.*
(Continued)

*Primary Examiner* — Jay Yang
(74) *Attorney, Agent, or Firm* — Lerner, David, Littenberg, Krumholz & Mentlik, LLP

(57) ABSTRACT

The present specification provides a heterocyclic compound and an organic light emitting device including the same.

12 Claims, 1 Drawing Sheet

(51) Int. Cl.
H01L 51/00 (2006.01)
C07C 13/567 (2006.01)

(52) U.S. Cl.
CPC ...... H01L 51/5076 (2013.01); H01L 51/5092 (2013.01); C09K 2211/1059 (2013.01)

(56) References Cited

U.S. PATENT DOCUMENTS

| | | |
|---|---|---|
| 2013/0324740 A1 | 12/2013 | Scott et al. |
| 2015/0025239 A1 | 1/2015 | Ahn et al. |
| 2016/0197285 A1 | 7/2016 | Zeng et al. |
| 2018/0079744 A1 | 3/2018 | Huang et al. |

FOREIGN PATENT DOCUMENTS

| | | |
|---|---|---|
| DE | 19720289 A1 | 11/1998 |
| JP | 2004059761 A | 2/2004 |
| JP | 2007223928 A | 9/2007 |
| JP | 2008110957 A | 5/2008 |
| JP | 201349640 A | 3/2013 |
| JP | 2015512875 A | 4/2015 |
| JP | 2015518892 A | 7/2015 |
| JP | 2016128432 A | 7/2016 |
| JP | 2018511653 A | 4/2018 |
| KR | 20150034664 A | 4/2015 |
| WO | 2010096462 A1 | 8/2010 |
| WO | WO-2013/022810 A1 * | 2/2013 |
| WO | 2015073343 A1 | 5/2015 |

OTHER PUBLICATIONS

Search report from International Application No. PCT/KR2016/010350, dated Dec. 23, 2016.
Supplementary European Search Report including the Written Opinion for Application No. 16846881.7 dated Apr. 11, 2019, 6 pages.

* cited by examiner

[FIG. 1]
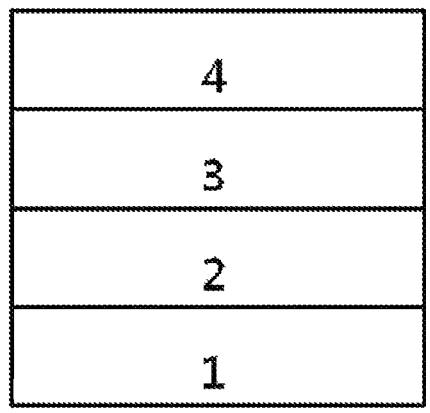
[FIG. 2]
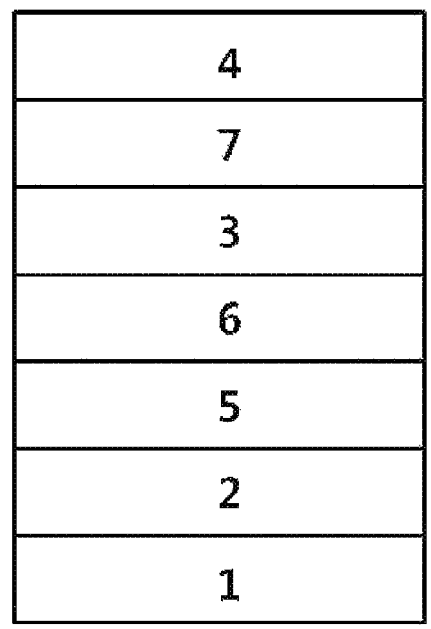

HETEROCYCLIC COMPOUND AND ORGANIC LIGHT EMITTING ELEMENT COMPRISING SAME

The present application is a national phase entry under 35 U.S.C. § 371 of International Application No. PCT/KR2016/010350 filed Sep. 13, 2016, published in Korean, which claims priority from Korean Patent Application No. 10-2015-0130356, filed Sep. 15, 2015, and Korean Patent Application No. 10-2016-0090117, filed Jul. 15, 2016, all of which are incorporated herein by reference.

TECHNICAL FIELD

The present specification claims priority to and the benefits of Korean Patent Application No. 10-2015-0130356, filed with the Korean Intellectual Property Office on Sep. 15, 2015, and Korean Patent Application No. 10-2016-0090117, filed with the Korean Intellectual Property Office on Jul. 15, 2016, the entire contents of which are incorporated herein by reference.

The present specification relates to a heterocyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

Korean Patent Application Laid-Open Publication No. 2015-0034664

DISCLOSURE

Technical Problem

The present specification describes a heterocyclic compound and an organic light emitting device including the same.

Technical Solution

One embodiment of the present specification provides a compound represented by the following Chemical Formula 1:

[Chemical Formula 1]

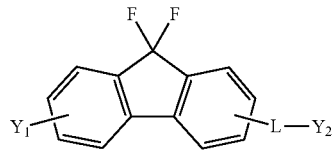

In Chemical Formula 1,

L is a direct bond; a substituted or unsubstituted arylene group; or a substituted or unsubstituted heteroarylene group, $Y_1$ is hydrogen; an aryl group unsubstituted or substituted with one or more $A_1$s; or a heterocyclic group unsubstituted or substituted with one or more $A_1$s, $Y_2$ is hydrogen; an aryl group unsubstituted or substituted with one or more $A_2$s; or a heterocyclic group unsubstituted or substituted with one or more $A_2$s, at least one of $Y_1$ and $Y_2$ is a nitrogen-containing heterocyclic group, $A_1$ and $A_2$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkoxy group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, when $Y_1$ is substituted with two or more $A_1$s, $A_1$s are the same as or different from each other, when $Y_2$ is substituted with two or more $A_2$s, $A_2$s are the same as or different from each other.

Another embodiment of the present specification provides an organic light emitting device comprising a first electrode, a second electrode, and one or more organic material layers disposed between the first electrode and the second electrode, wherein one or more layers of the organic material layers comprise the compound of Chemical Formula 1.

Advantageous Effects

Compounds described in the present specification can be used as a material of an organic material layer of an organic light emitting device. Compounds according to at least one embodiment are capable of enhancing efficiency, low driving voltage and/or enhancing lifespan properties in an organic light emitting device. Particularly, compounds described in the present specification can be used as a material of hole injection, hole transfer, hole injection and hole transfer, electron suppression, light emission, hole suppression, electron transfer or electron injection.

DESCRIPTION OF DRAWINGS

FIG. 1 illustrates an organic light emitting device formed with a substrate (1), an anode (2), a light emitting layer (3) and a cathode (4).

FIG. 2 illustrates an organic light emitting device formed with a substrate (1), an anode (2), a hole injection layer (5), a hole transfer layer (6), a light emitting layer (3), an electron transfer layer (7) and a cathode (4).

REFERENCE NUMERAL

1: Substrate
2: Anode
3: Light Emitting Layer
4: Cathode
5: Hole Injection Layer
6: Hole Transfer Layer
7: Electron Transfer Layer

MODE FOR DISCLOSURE

Hereinafter, the present specification will be described in more detail.

One embodiment of the present specification provides a compound represented by Chemical Formula 1.

Examples of the substituents are described below, however, the substituents are not limited thereto.

In the present specification, the term "substituted or unsubstituted" means being substituted with one or more substituents selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, examples of the halogen group may include fluorine, chlorine, bromine or iodine.

In the present specification, the number of carbon atoms of the carbonyl group is not particularly limited, but is preferably from 1 to 40. Specifically, compounds having structures as below may be included, but the carbonyl group is not limited thereto.

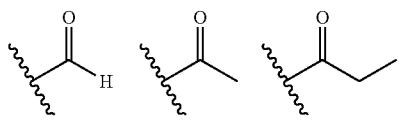

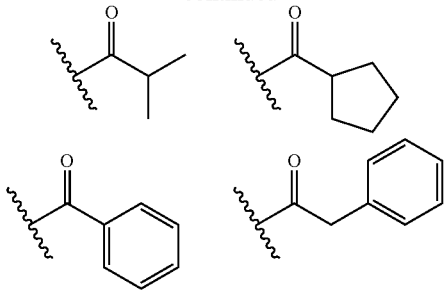

In the present specification, in the ester group, the oxygen of the ester group may be substituted with a linear, branched or cyclic alkyl group having 1 to 40 carbon atoms or an aryl group having 6 to 30 carbon atoms. Specifically, compounds having the following structural formulae may be included, but the ester group is not limited thereto.

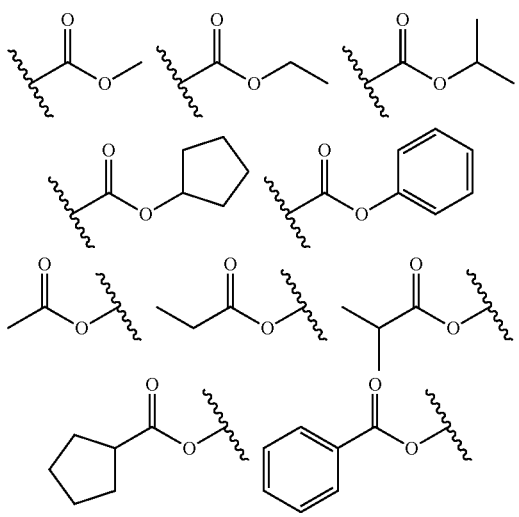

In the present specification, the number of carbon atoms of the imide group is not particularly limited, but is preferably from 1 to 25. Specifically, compounds having structures as below may be included, but the imide group is not limited thereto.

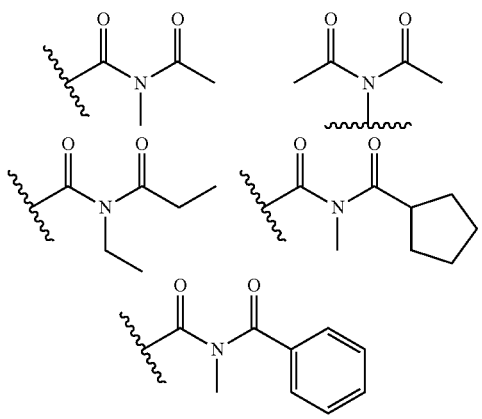

In the present specification, the silyl group may be represented by the chemical formula of —SiR$_a$R$_c$R$_c$, and R$_a$, R$_b$ and R$_c$ may each be hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —BR$_a$R$_b$, and R$_a$ and R$_b$ may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and the number of carbon atoms is not particularly limited, but is preferably from 1 to 40. According to one embodiment, the number of carbon atoms of the alkyl group is from 1 to 20. According to another embodiment, the number of carbon atoms of the alkyl group is from 1 to 10. According to still another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 4-methylhexyl, 5-methylhexyl and the like, but are not limited thereto.

In the present specification, the alkoxy group may be linear, branched or cyclic. The number of carbon atoms of the alkoxy group is not particularly limited, but is preferably from 1 to 40. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

The alkyl group, the alkoxy group and other substituents including an alkyl group part described in the present specification include all of linear or branched forms.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to still another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of carbon atoms of the cycloalkyl group is from 3 to 20. According to still another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the number of carbon atoms of the alkylamine group is not particularly limited, but is preferably from 1 to 40. Specific examples of the alkylamine group may include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, a phenylnaphthylamine group, a ditolylamine group, a phenyltolylamine group, a triphenylamine group and the like, but are not limited thereto.

In the present specification, examples of the arylamine group may include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups.

Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include monocyclic heterocyclic groups, multicyclic heterocyclic groups, or both monocyclic heterocyclic groups and multicyclic heterocyclic groups.

In the present specification, the arylheteroarylamine group means an amine group substituted with an aryl group and a heterocyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both monocyclic aryl groups and multicyclic aryl groups.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. Examples of the monocyclic aryl group may include a phenyl group, a biphenyl group, a terphenyl group and the like, but are not limited thereto. Examples of the multicyclic aryl group may include a naphthyl group, an anthracenyl group, a phenanthrenyl group, a pyrenyl group, a perylenyl group, a chrysenyl group, a fluorenyl group and the like, but are not limited thereto.

In the present specification, the fluorenyl group may be substituted, and two of the substituents may bond to each other to form a spiro structure.

When the fluorenyl group is substituted, spirofluorenyl groups such as

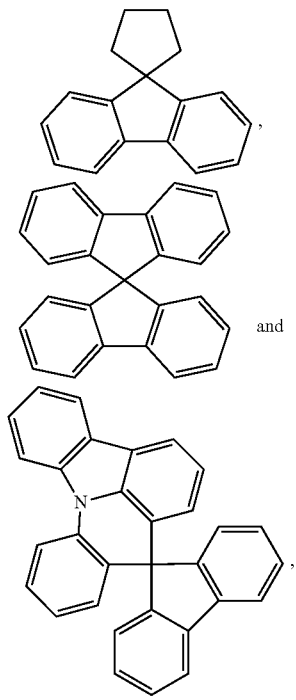

and substituted fluorenyl groups such as

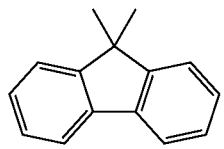

(9,9-dimethylfluorenyl group) and

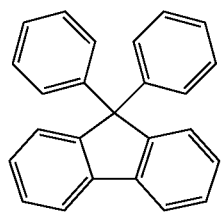 [SMILES: c1ccc(C2(c3ccccc3)c3ccccc3-c3ccccc32)cc1]

(9,9-diphenylfluorenyl group) may be included. However, the compounds are not limited thereto.

In the present specification, the heterocyclic group is a heterocyclic group including one or more of N, O, P, S, Si and Se as a heteroatom, and although not particularly limited thereto, the number of carbon atoms is preferably from 1 to 60. According to one embodiment, the number of carbon atoms of the heterocyclic group is from 1 to 30. Examples of the heterocyclic group may include a pyridine group, a pyrrole group, a pyrimidine group, a pyridazine group, a furan group, a thiophene group, an imidazole group, a pyrazole group, an oxazole group, an isoxazole group, a triazole group, an isothiazole group, a triazole group, an oxadiazole group, a thiadiazole group, a dithiazole group, a tetrazole group, a pyran group, a thiopyran group, a pyrazine group, an oxazine group, a triazine group, a dioxine group, a triazine group, a tetrazine group, a quinoline group, an isoquinoline group, a quinazoline group, a quinoxaline group, a naphthyridine group, an acridine group, a xanthene group, a phenanthridine group, a diazanaphthalene group, a triazaindene group, an indole group, an indoline group, an indolizine group, a phthalazine group, a pyridopyrimidine group, a pyridopyrazine group, a pyrazinopyrazine group, a benzothiazole group, a benzoxazole group, a benzimidazole group, a benzothiophene group, a benzofuran group, a dibenzothiophene group, a dibenzofuran group, a dibenzosilol group, a carbazole group, a benzocarbazole group, a dibenzocarbazole group, an indolocarbazole group, an indenocarbazole group, a phenazine group, an imidazopyridine group, a phenoxazine group, a phenanthridine group, a phenanthroline group, a phenothiazine group, an imidazopyridine group, an imidazophenanthridine group, a benzimidazoquinazoline group, a benzimidazophenanthridine group,

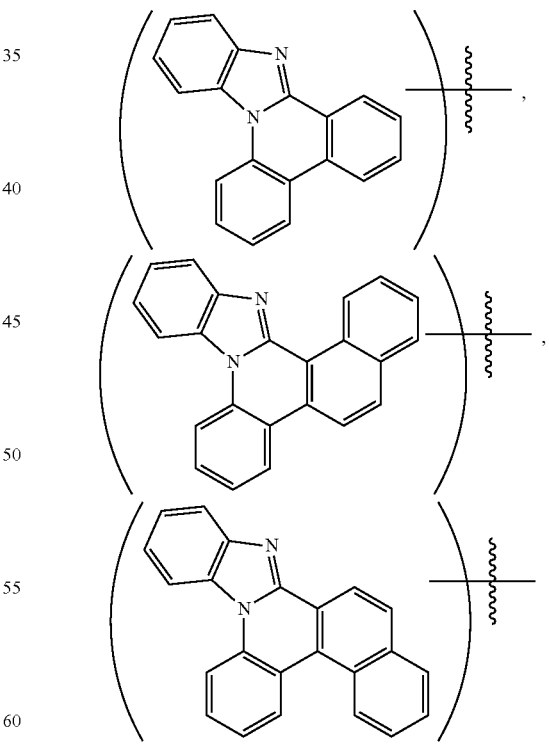

and the like, but are not limited thereto.

In the present specification, the nitrogen-containing heterocyclic group is a heterocyclic group including at least one nitrogen atom as a ring member, and atoms forming the ring may be 5, 6, 7 or higher.

Specifically, examples of the monocyclic nitrogen-containing heterocyclic group may include a pyridine group, a pyrimidine group, a pyrazine group, a pyridazine group, a triazine group, a pyrazole group, an oxazole group, a thiazole group, a trizaole group, an oxadiazole group and a thiadiazole group. Examples of the multicyclic nitrogen-containing heterocyclic group may include a benzimidazole group, a benzoxazole group, a benzothiazole group, a phenazinyl group, a phenoxazine group, a phenanthridine group, a phenanthroline group, a phenothiazine group, an imidazopyridine group, an imidazophenanthridine group, a benzimidazoquinazoline group, a benzimidazophenanthridine group and the like.

In the present specification, the descriptions on the aryl group provided above may be used on the aryl group in the aryloxy group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, the descriptions on the alkyl group provided above may be used on the alkyl group in the alkylthioxy group, the alkylsulfoxy group, the aralkyl group, the aralkylamine group, the alkylaryl group and the alkylamine group.

In the present specification, the descriptions on the heterocyclic group provided above may be used on the heteroaryl group in the heteroaryl group, the heteroarylamine group and the arylheteroarylamine group except that the heteroaryl group is an aromatic group.

In the present specification, the descriptions on the alkenyl group provided above may be used on the alkenyl group in the aralkenyl group.

In the present specification, the descriptions on the aryl group provided above may be used on the arylene group except the arylene group is divalent.

In the present specification, the descriptions on the heterocyclic group provided above may be used on the heteroarylene group except that the heteroarylene group is divalent of an aromatic heterocyclic group.

In one embodiment of the present specification, $Y_1$ is hydrogen; an aryl group unsubstituted or substituted with one or more $A_1$s; or a heterocyclic group unsubstituted or substituted with one or more $A_1$s, $Y_2$ is hydrogen; an aryl group unsubstituted or substituted with one or more $A_2$s; or a heterocyclic group unsubstituted or substituted with one or more $A_2$s, and at least one of $Y_1$ and $Y_2$ is a nitrogen-containing heterocyclic group.

In one embodiment of the present disclosure, $Y_1$ is a nitrogen-containing heterocyclic group unsubstituted or substituted with one or more $A_1$s, and $Y_2$ is an aryl group unsubstituted or substituted with one or more $A_2$s; or a heterocyclic group unsubstituted or substituted with one or more $A_2$s.

In one embodiment, $Y_1$ is a monocyclic nitrogen-containing heterocyclic group unsubstituted or substituted with one or more $A_1$s, and $Y_2$ is an aryl group unsubstituted or substituted with one or more $A_2$s; or a heterocyclic group unsubstituted or substituted with one or more $A_2$s.

In another embodiment, $Y_1$ and $Y_2$ are the same as or different from each other, and $Y_1$ is a nitrogen-containing heterocyclic group unsubstituted or substituted with one or more $A_1$s, and $Y_2$ is a nitrogen-containing heterocyclic group unsubstituted or substituted with one or more $A_2$s.

In one embodiment, $Y_1$ and $Y_2$ are the same as or different from each other, and $Y_1$ is a monocyclic nitrogen-containing heterocyclic group unsubstituted or substituted with one or more $A_1$s, and $Y_2$ is a monocyclic nitrogen-containing heterocyclic group unsubstituted or substituted with one or more $A_2$s.

In one embodiment, $Y_1$ and $Y_2$ are the same as or different from each other, and each independently a monocyclic nitrogen-containing heterocyclic group substituted with an aryl group.

In one embodiment of the present disclosure, $Y_1$ is a nitrogen-containing heterocyclic group unsubstituted or substituted with one or more $A_1$s, and $Y_2$ is hydrogen.

In one embodiment, $Y_1$ is a monocyclic nitrogen-containing heterocyclic group unsubstituted or substituted with one or more $A_1$s, and $Y_2$ is hydrogen.

In another embodiment, $Y_1$ is hydrogen, and $Y_2$ is a nitrogen-containing heterocyclic group unsubstituted or substituted with $A_2$.

In one embodiment, $Y_1$ is hydrogen, and $Y_2$ is a monocyclic nitrogen-containing heterocyclic group unsubstituted or substituted with $A_2$.

Specifically, the monocyclic nitrogen-containing heterocyclic group is any one selected from the group consisting of a pyridine group, a pyrimidine group, a pyrazine group, a pyridazine group and a triazine group.

According to one embodiment of the present specification, the compound represented by Chemical Formula 1 may be represented by any one of the following Chemical Formula 2 to Chemical Formula 4.

[Chemical Formula 2]

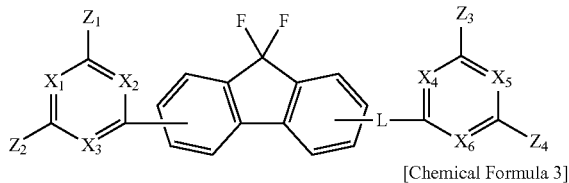

[Chemical Formula 3]

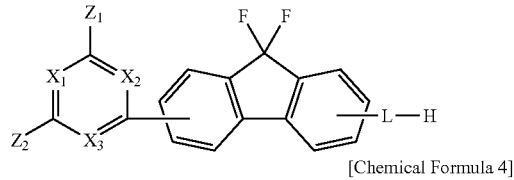

[Chemical Formula 4]

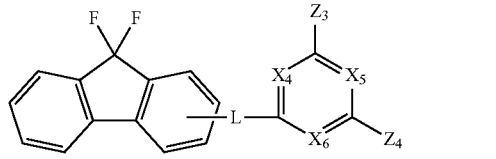

In Chemical Formula 2 to Chemical Formula 4, a definition of L is the same as in Chemical Formula 1, $X_1$ to $X_6$ are N or CH, at least one of $X_1$ to $X_3$ is N, at least one of $X_4$ to $X_6$ is N, and $Z_1$ to $Z_4$ have the same definitions as $A_1$ and $A_2$ in Chemical Formula 1.

According to one embodiment of the present specification, the compound of Chemical Formula 2 may be represented by any one of the following Chemical Formula 5 to Chemical Formula 8.

[Chemical Formula 5]

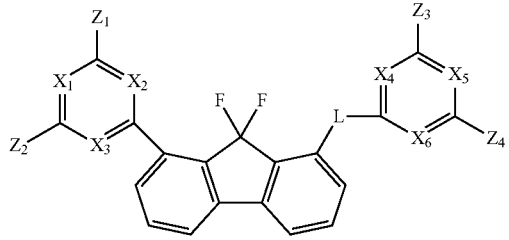

[Chemical Formula 6]

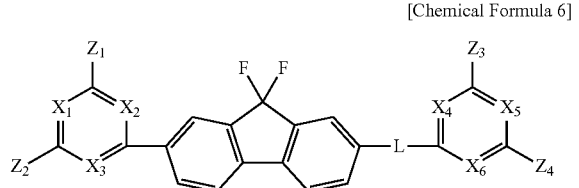

[Chemical Formula 7]

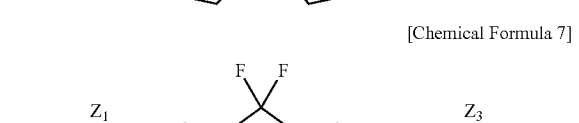

[Chemical Formula 8]

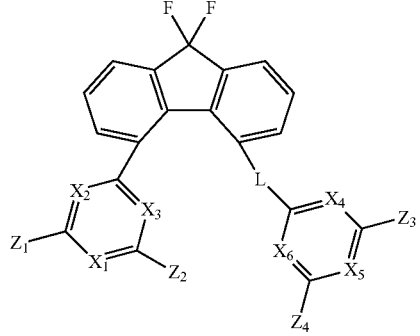

In Chemical Formula 5 to Chemical Formula 8, definitions of L, $X_1$ to $X_6$ and $Z_1$ to $Z_4$ are the same as in Chemical Formula 2.

According to one embodiment of the present specification, the compound of Chemical Formula 3 may be represented by any one of the following Chemical Formula 9 to Chemical Formula 12.

[Chemical Formula 9]

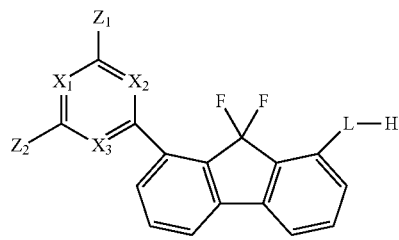

[Chemical Formula 10]

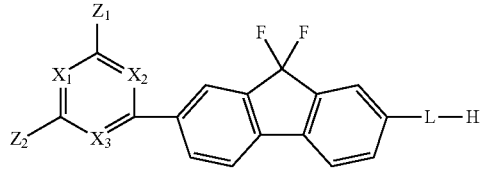

[Chemical Formula 11]

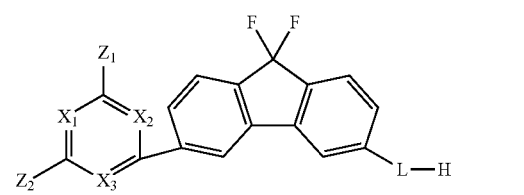

[Chemical Formula 12]

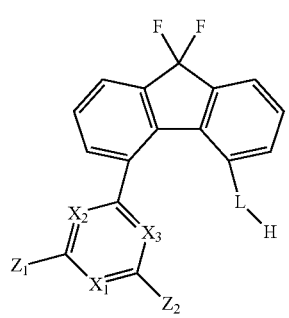

In Chemical Formula 9 to Chemical Formula 12, definitions of L, $X_1$ to $X_3$, $Z_1$ and $Z_2$ are the same as in Chemical Formula 3.

According to one embodiment of the present specification, the compound of Chemical Formula 4 may be represented by any one of the following Chemical Formula 13 to Chemical Formula 16.

[Chemical Formula 13]

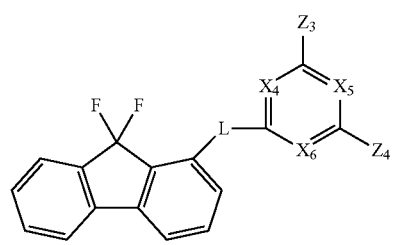

[Chemical Formula 14]

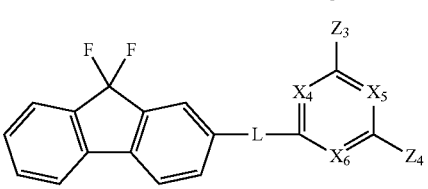

-continued

[Chemical Formula 15]

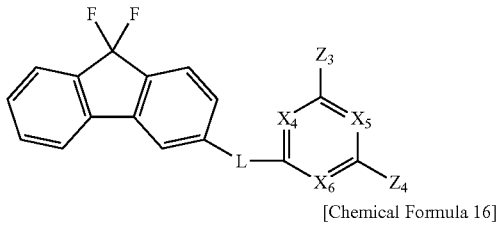

[Chemical Formula 16]

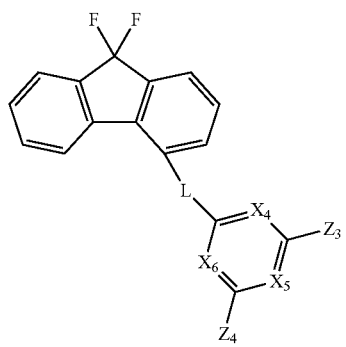

In Chemical Formula 13 to Chemical Formula 16, definitions of L, $X_4$ to $X_6$, $Z_3$ and $Z_4$ are the same as in Chemical Formula 4.

In one embodiment, $Y_1$ and $Y_2$ are the same as or different from each other, and each independently a pyridyl group substituted with an aryl group; a pyrimidyl group substituted with an aryl group; or a triazinyl group substituted with an aryl group, and the aryl group is any one selected from the group consisting of a phenyl group, a biphenyl group, a terphenyl group, a quaterphenyl group, a naphthyl group, an anthracenyl group, a phenanthrenyl group, a triphenylenyl group, a pyrenyl group and a fluorenyl group.

In another embodiment, $Y_1$ is a direct bond, $A_1$ is hydrogen, and $Y_2$ is a pyridyl group substituted with an aryl group; a pyrimidyl group substituted with an aryl group; or a triazinyl group substituted with an aryl group, and the aryl group is any one selected from the group consisting of a phenyl group, a biphenyl group, a terphenyl group, a quaterphenyl group, a naphthyl group, an anthracenyl group, a phenanthrenyl group, a triphenylenyl group, a pyrenyl group and a fluorenyl group.

In one embodiment, $Y_1$ and $Y_2$ are the same as or different from each other, and each independently a pyridyl group substituted with a phenyl group; a pyrimidyl group substituted with a phenyl group; or a triazinyl group substituted with a phenyl group.

In another embodiment, $Y_1$ is a direct bond, $A_1$ is hydrogen, and $Y_2$ is a pyridyl group substituted with a phenyl group; a pyrimidyl group substituted with a phenyl group; or a triazinyl group substituted with a phenyl group.

In one embodiment of the present disclosure, L is a direct bond; a substituted or unsubstituted arylene group having 6 to 60 carbon atoms; or a substituted or unsubstituted heteroarylene group having 1 to 60 carbon atoms.

In one embodiment of the present disclosure, L is a direct bond; a monocyclic or multicyclic substituted or unsubstituted arylene group having 6 to 30 carbon atoms; or a monocyclic or multicyclic substituted or unsubstituted heteroarylene group having 1 to 30 carbon atoms.

In one embodiment of the present disclosure, L is a direct bond; a substituted or unsubstituted phenylene group; a substituted or unsubstituted biphenylylene group; a substituted or unsubstituted terphenylene group; a substituted or unsubstituted quaterphenylene group; a substituted or unsubstituted naphthylene group; a substituted or unsubstituted anthracenylene group; a substituted or unsubstituted phenanthrenylene group; a substituted or unsubstituted triphenylenylene group; a substituted or unsubstituted pyrenylene group; a substituted or unsubstituted fluorenylene group; a substituted or unsubstituted pyridinylene group; a substituted or unsubstituted pyrimidinylene group; a substituted or unsubstituted pyridazinylene group; a substituted or unsubstituted triazinylene group; a substituted or unsubstituted pyrazolylene group; a substituted or unsubstituted oxazolylene group; a substituted or unsubstituted triazolylene group; a substituted or unsubstituted triazolylene group; a substituted or unsubstituted oxadiazolylene group; a substituted or unsubstituted thiadiazolylene group; a substituted or unsubstituted quinolinylene group; a substituted or unsubstituted isoquinolinylene group; a substituted or unsubstituted quinazolinylene group; a substituted or unsubstituted quinoxalinylene group; a substituted or unsubstituted benzimidazolylene group; a substituted or unsubstituted benzoxazolylene group; a substituted or unsubstituted benzothiazolylene group; a substituted or unsubstituted dibenzofuranylene group; a substituted or unsubstituted dibenzothiophenylene group; a substituted or unsubstituted dibenzosilolylene; or a substituted or unsubstituted carbazolylene group.

In one embodiment, L is a direct bond; a substituted or unsubstituted arylene group; or a substituted or unsubstituted heteroarylene group.

In one embodiment, L is a direct bond; a phenylene group unsubstituted or substituted with one or more substituents selected from the group consisting of a nitrile group, a triphenylsilyl group, a triphenylmethyl group, a phenyl group unsubstituted or substituted with a nitrile group, pyridine group, a quinoline group unsubstituted or substituted with a pyridine group, a dibenzofuran group, a dibenzothiophene group, a carbazole group, and a dibenzosilol group unsubstituted or substituted with a methyl group; a substituted or unsubstituted naphthylene group; a substituted or unsubstituted anthracenylene group; a substituted or unsubstituted phenanthrenylene group; a substituted or unsubstituted fluorenylene group; a substituted or unsubstituted triphenylenylene group; a pyridinylene group unsubstituted or substituted with one or more substituents selected from the group consisting of a phenyl group, a biphenyl group and a naphthyl group; a pyrimidinylene group unsubstituted or substituted with one or more substituents selected from the group consisting of a phenyl group, a biphenyl group and a naphthyl group; pyridazinylene group; a triazinylene group unsubstituted or substituted with one or more substituents selected from the group consisting of a phenyl group, a biphenyl group and a naphthyl group; an oxadiazolylene group unsubstituted or substituted with a phenyl group; a thiadiazolylene group unsubstituted or substituted with a phenyl group; a quinolinylene group; a quinoxalinylene group; a dibenzothiophenylene group; a dibenzofuranylene group; a carbazolylene group unsubstituted or substituted with an aryl group;

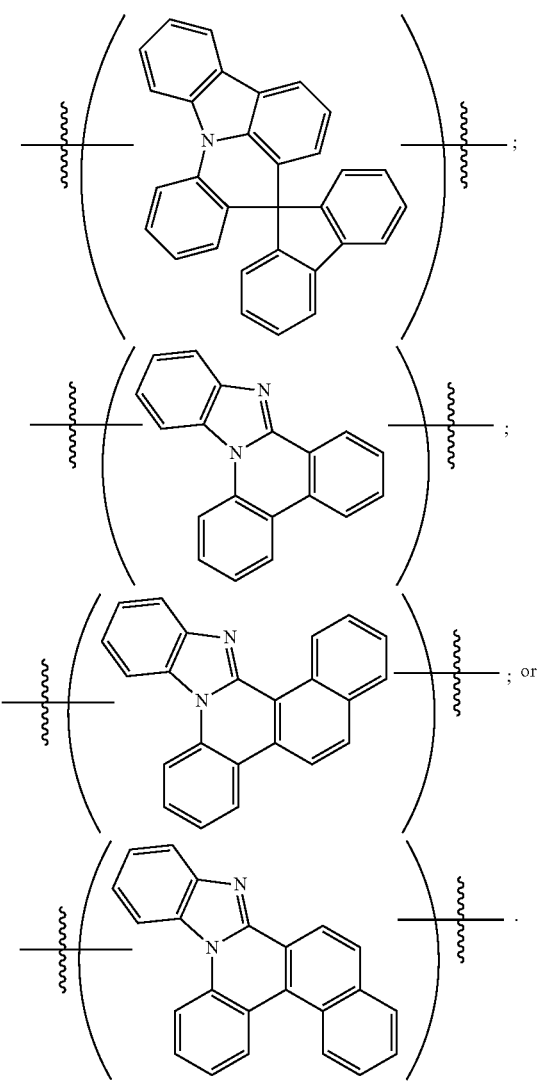

In one embodiment of the present disclosure, $A_1$ and $A_2$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkoxy group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

In another embodiment, $A_1$ is hydrogen, and $A_2$ is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkoxy group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

In one embodiment of the present disclosure, $A_1$ and $A_2$ are the same as or different from each other, and each independently hydrogen; deuterium; a nitrile group; a silyl group unsubstituted or substituted with an aryl group having 1 to 40 carbon atoms or an aryl group having 16 to 60 carbon atoms; a phosphine oxide group unsubstituted or substituted with an alkyl group having 1 to 40 carbon atoms or an aryl group having 6 to 60 carbon atoms; an alkyl group having 1 to 40 carbon atoms; an alkoxy group having 1 to 40 carbon atoms; a substituted or unsubstituted aryl group having 6 to 60 carbon atoms; or a substituted or unsubstituted heterocyclic group having 1 to 60 carbon atoms.

In another embodiment, $A_1$ is hydrogen, and $A_2$ is hydrogen; deuterium; a nitrile group; a silyl group unsubstituted or substituted with an alkyl group having 1 to 40 carbon atoms or an aryl group having 6 to 60 carbon atoms; a phosphine oxide group unsubstituted or substituted with an alkyl group having 1 to 40 carbon atoms or an aryl group having 6 to 60 carbon atoms; an alkyl group having 1 to 40 carbon atoms; an alkoxy group having 1 to 40 carbon atoms; a substituted or unsubstituted aryl group having 6 to 60 carbon atoms; or a substituted or unsubstituted heterocyclic group having 1 to 60 carbon atoms.

In one embodiment of the present disclosure, $A_1$ and $A_2$ are the same as or different from each other, and each independently hydrogen; deuterium; a nitrile group; a silyl group unsubstituted or substituted with an alkyl group having 1 to 20 carbon atoms or an aryl group having 6 to 30 carbon atoms; a phosphine oxide group unsubstituted or substituted with an alkyl group having 1 to 20 carbon atoms or an aryl group having 6 to 30 carbon atoms; an alkyl group having 1 to 20 carbon atoms; an alkoxy group having 1 to 20 carbon atoms; a monocyclic or multicyclic substituted or unsubstituted aryl group having 6 to 30 carbon atoms; or a monocyclic or multicyclic substituted or unsubstituted heterocyclic group having 1 to 30 carbon atoms.

In another embodiment, $A_1$ is hydrogen, and $A_2$ is hydrogen; deuterium; a nitrile group; a silyl group unsubstituted or substituted with an alkyl group having 1 to 20 carbon atoms or an aryl group having 6 to 30 carbon atoms; a phosphine oxide group unsubstituted or substituted with an alkyl group having 1 to 20 carbon atoms or an aryl group having 6 to 30 carbon atoms; an alkyl group having 1 to 20 carbon atoms; an alkoxy group having 1 to 20 carbon atoms; a monocyclic or multicyclic substituted or unsubstituted aryl group having 6 to 30 carbon atoms; or a monocyclic or multicyclic substituted or unsubstituted heterocyclic group having 1 to 30 carbon atoms.

In one embodiment of the present disclosure, $A_1$ and $A_2$ are the same as or different from each other, and each independently hydrogen; deuterium; a nitrile group; a silyl group; a substituted or unsubstituted phosphine oxide group; a substituted or unsubstituted alkyl group; a substituted or unsubstituted alkoxy group; an aryl group such as a substituted or unsubstituted phenyl group; a substituted or unsubstituted biphenyl group; a substituted or unsubstituted terphenyl group; a substituted or unsubstituted quaterphenyl group; a substituted or unsubstituted naphthyl group; a substituted or unsubstituted anthracenyl group; a substituted or unsubstituted chrysenyl group; a substituted or unsubstituted phenanthrenyl group; a substituted or unsubstituted triperylenyl group; a substituted or unsubstituted pyrenyl group; a substituted or unsubstituted tetracenyl group; a substituted or unsubstituted pentacenyl group; or a substituted or unsubstituted fluorenyl group; or a heterocyclic group such as a substituted or unsubstituted pyrimidyl group; a substituted or unsubstituted pyrimidinyl group; a substituted or unsubstituted triazinyl group; a substituted or unsubstituted quinolinyl group; a substituted or unsubstituted isoquinolinyl group; a substituted or unsubstituted quinazolinyl group; a substituted or unsubstituted quinoxalinyl group; a substituted or unsubstituted naphthyridinyl group; a substituted or unsubstituted acridyl group; a substituted or unsubstituted xanthenyl group; a substituted or unsubstituted phenanthridinyl group; a substituted or unsubstituted diazanaphthalenyl group; a substituted or unsubstituted triazaindenyl group; a substituted or unsubstituted indole group; a substituted or unsubstituted indolinyl group; a substituted or unsubstituted indolizinyl group; a substituted or unsubstituted phthalazinyl group; a substituted or unsubstituted benzimidazole group; a substituted or unsubstituted benzoxazole group; a substituted or unsubstituted benzothiazole group; a substituted or unsubstituted pyridopyrimidinyl group; a substituted or unsubstituted pyridopyrazinyl group; a substituted or unsubstituted pyrazinopyrazinyl group; a substituted or unsubstituted carbazolyl group; a substituted or unsubstituted benzothiophene group; a substituted or unsubstituted benzofuranyl group; a substituted or unsubstituted benzocarbazolyl group; a substituted or unsubstituted naphthobenzothiophene group; a substituted or unsubstituted naphthobenzofuranyl group; a substituted or unsubstituted dibenzocarbazolyl group; a substituted or unsubstituted indolocarbazolyl group; a substituted or unsubstituted indenocarbazolyl group; a substituted or unsubstituted phenanthroline group; a substituted or unsubstituted phenazinyl group; a substituted or unsubstituted phenoxazinyl group; a substituted or unsubstituted phenothiazinyl group; a substituted or unsubstituted imidazopyridinyl group; a substituted or unsubstituted imidazophenanthridine group; a substituted or unsubstituted benzimidazoquinazolinyl group; or a substituted or unsubstituted benzimidazophenanthridinyl group.

In one embodiment of the present disclosure, $A_1$ and $A_2$ are the same as or different from each other, and each independently hydrogen; deuterium; a nitrile group; a substituted or unsubstituted silyl group; a substituted or unsubstituted phosphine oxide group; a substituted or unsubstituted alkyl group; a substituted or unsubstituted alkoxy group; an aryl group such as a substituted or unsubstituted phenyl group; a substituted or unsubstituted biphenyl group; a substituted or unsubstituted terphenyl group; a substituted or unsubstituted quaterphenyl group; a substituted or unsubstituted naphthyl group; a substituted or unsubstituted anthracenyl group; a substituted or unsubstituted chrysenyl group; a substituted or unsubstituted phenanthrenyl group; a substituted or unsubstituted triperylenyl group; a substituted or unsubstituted pyrenyl group; a substituted or unsubstituted tetracenyl group; a substituted or unsubstituted pentacenyl group; or a substituted or unsubstituted fluorenyl group; or a heterocyclic group such as a substituted or unsubstituted pyrimidyl group; a substituted or unsubstituted pyrimidinyl group; a substituted or unsubstituted triazinyl group; a substituted or unsubstituted quinolinyl group; a substituted or unsubstituted isoquinolinyl group; a substituted or unsubstituted quinazolinyl group; a substituted or unsubstituted quinoxalinyl group; a substituted or unsubstituted naphthyridinyl group; a substituted or unsubstituted acridyl group; a substituted or unsubstituted xanthenyl group; a substituted or unsubstituted phenanthridinyl group; a substituted or unsubstituted diazanaphthalenyl group; a substituted or unsubstituted triazaindenyl group; a substituted or unsubstituted indole group; a substituted or unsubstituted indolinyl group; a substituted or unsubstituted indolizinyl group; a substituted or unsubstituted phthalazinyl group; a substituted or unsubstituted benzimidazole group; a substituted or unsubstituted benzoxazole group; a substituted or unsubstituted benzothiazole group; a substituted or unsubstituted pyridopyrimidinyl group; a substituted or unsubstituted pyridopyrazinyl group; a substituted or unsubstituted pyrazinopyrazinyl group; a substituted or unsubstituted carbazolyl group; a substituted or unsubstituted benzothiophene group; a substituted or unsubstituted benzofuranyl group; a substituted or unsubstituted benzocarbazolyl group; a substituted or unsubstituted naphthobenzothiophene group; a substituted or unsubstituted naphthobenzofuranyl group; a substituted or unsubstituted dibenzocarbazolyl group; a substituted or unsubstituted indolocarbazolyl group; a substituted or unsubstituted indenocarbazolyl group; a substituted or unsubstituted phenanthroline group; a substituted or unsubstituted phenazinyl group; a substituted or unsubstituted phenoxazinyl group; a substituted or unsubstituted phenothiazinyl group; a substituted or unsubstituted imidazopyridinyl group; a substituted or unsubstituted imidazophenanthridine group; a substituted or unsubstituted benzimidazoquinazolinyl group; a substituted or unsubstituted benzimidazophenanthridinyl group;

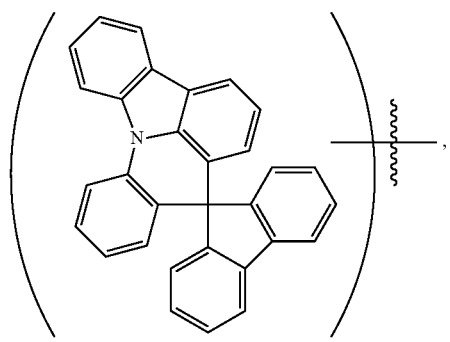

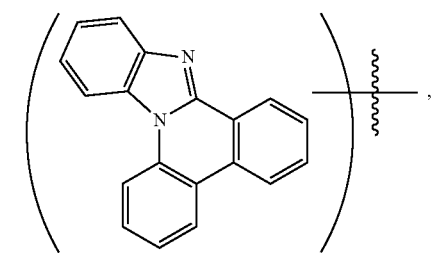

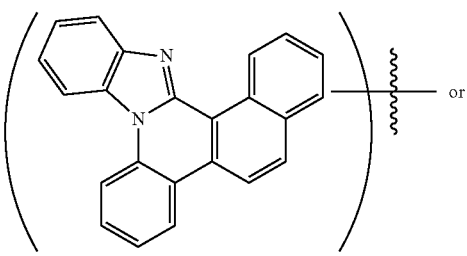

or

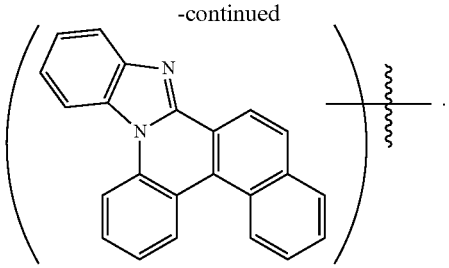

In another embodiment, $A_1$ is hydrogen, $A_2$ is hydrogen; deuterium; a nitrile group; a triphenylsilyl group; a diphenylphosphine oxide group; a phenyl group unsubstituted or substituted with one or more substituents selected from the group consisting of a nitrile group, a phenyl group, a quinoline group and a pyridine group; a biphenyl group; a naphthyl group; a fluorenyl group unsubstituted or substituted with one or more substituents selected from the group consisting of an alkyl group and an aryl group; a pyridine group unsubstituted or substituted with one or more substituents selected from the group consisting of a phenyl group and a pyridine group; a pyrimidine group unsubstituted or substituted with one or more substituents selected from the group consisting of a phenyl group, a biphenyl group, a naphthyl group and a methoxy group; a triazine group unsubstituted or substituted with one or more substituents selected from the group consisting of a phenyl group, a biphenyl group, a naphthyl group and a methoxy group; an oxadiazole group unsubstituted or substituted with a phenyl group; a thiadiazole group unsubstituted or substituted with a phenyl group; a quinoline group unsubstituted or substituted with a pyridine group; or a carbazole group.

In one embodiment, $A_1$ and $A_2$ are the same as or different from each other, and each independently hydrogen; deuterium; or a substituted or unsubstituted aryl group.

In one embodiment, $A_1$ and $A_2$ are the same as or different from each other, and each independently hydrogen; deuterium; or a substituted or unsubstituted phenyl group.

In one embodiment of the present disclosure, $X_1$ to $X_6$ are N or CH, any one of $X_1$ to $X_3$ is N, and any one of $X_4$ to $X_6$ is N.

In one embodiment, $X_1$ to $X_3$ are all N.

In one embodiment, two of $X_1$ to $X_3$ are N, and the remaining one is CH.

In one embodiment, $X_1$ and $X_2$ are N, and $X_3$ is CH.
In one embodiment, $X_1$ and $X_3$ are N, and $X_2$ is CH.
In one embodiment, $X_2$ and $X_3$ are N, and $X_1$ is CH.

In one embodiment, any one of $X_1$ to $X_3$ is N, and the remaining two are CH.

In one embodiment, $X_1$ is N, and $X_2$ and $X_3$ are CH.
In one embodiment, $X_2$ is N, and $X_1$ and $X_3$ are CH.
In one embodiment, $X_3$ is N, and $X_1$ and $X_2$ are CH.
In one embodiment, $X_4$ to $X_6$ are all N.

In one embodiment, any two of $X_4$ to $X_6$ are N, and the remaining one is CH.

In one embodiment, $X_4$ and $X_5$ are N, and $X_6$ is CH.
In one embodiment, $X_4$ and $X_6$ are N, and $X_5$ is CH.
In one embodiment, $X_5$ and $X_6$ are N, and $X_4$ is CH.

In one embodiment, any one of $X_4$ to $X_6$ is N, and the remaining two are CH.

In one embodiment, $X_4$ is N, and $X_5$ and $X_6$ are CH.
In one embodiment, $X_5$ is N, and $X_4$ and $X_6$ are CH.
In one embodiment, $X_6$ is N, and $X_4$ and $X_5$ are CH.

In one embodiment of the present disclosure, the compound of Chemical Formula 1 may be any one selected from among the following compounds.

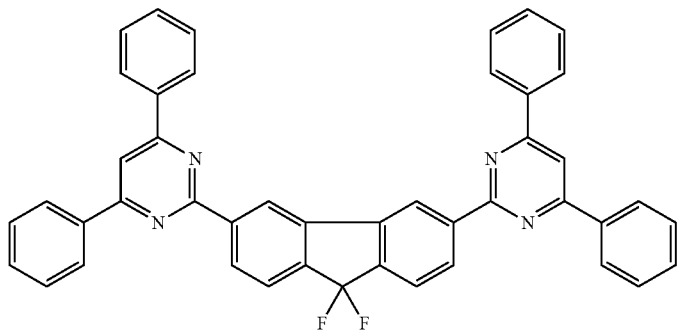

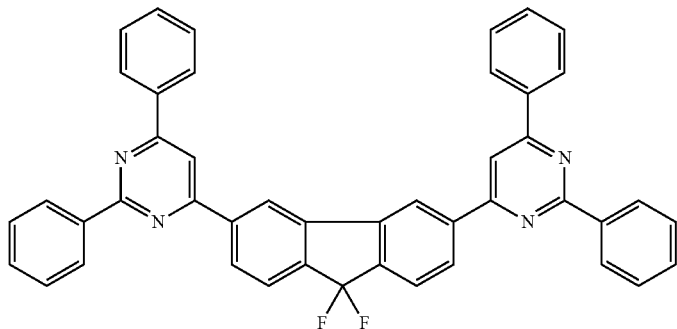

-continued
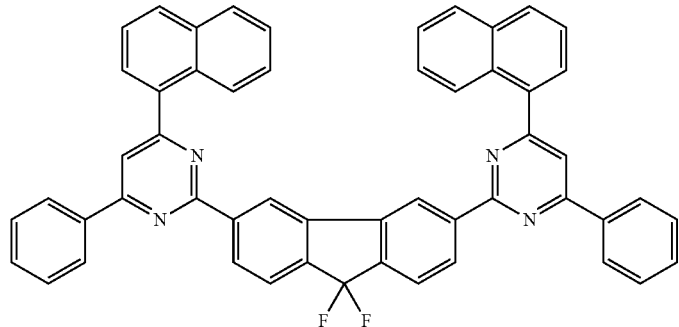
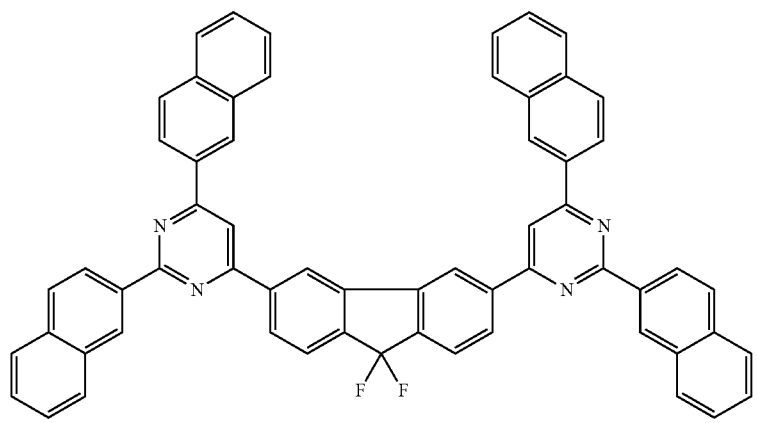
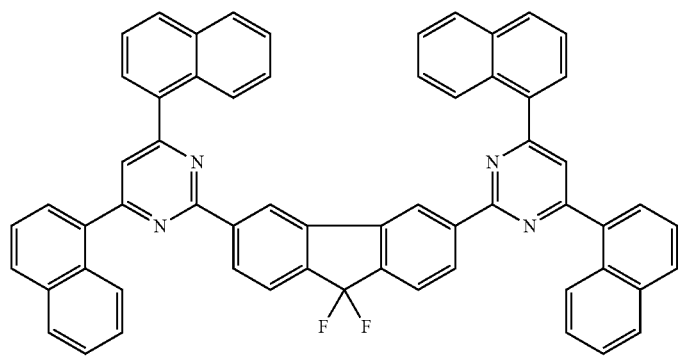
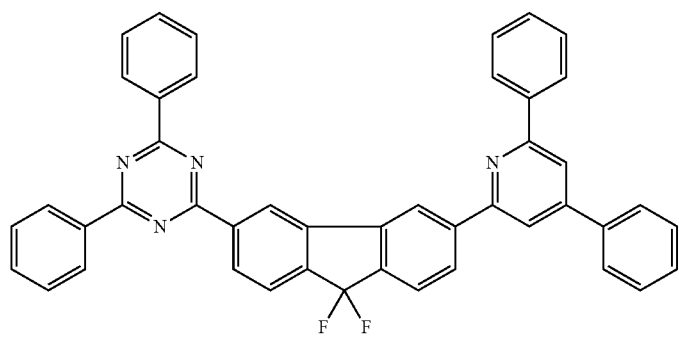

-continued
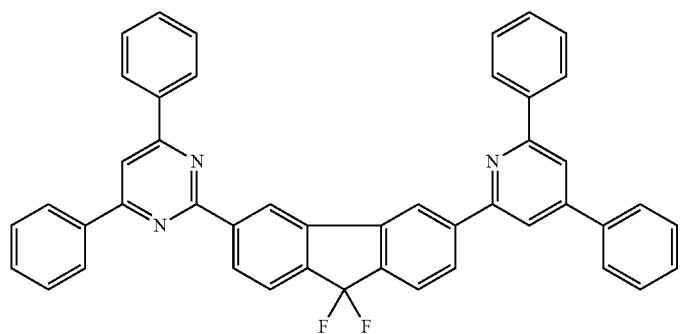
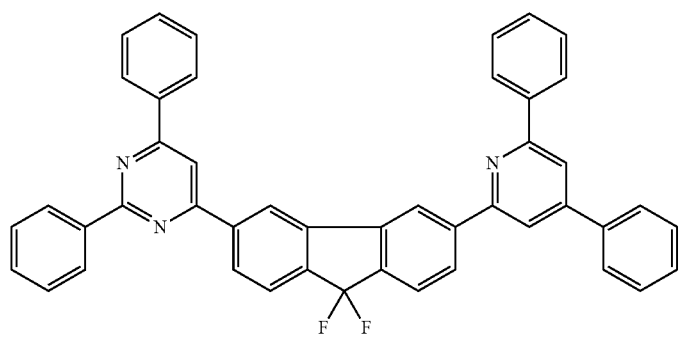
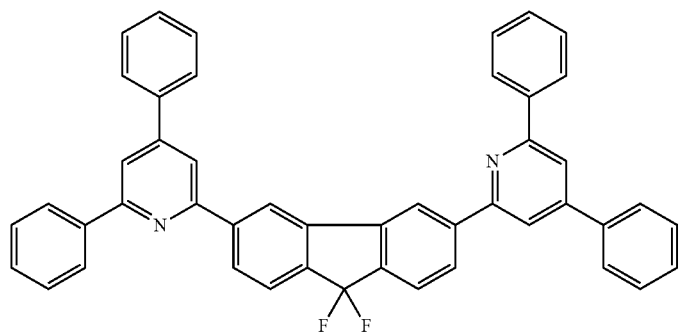
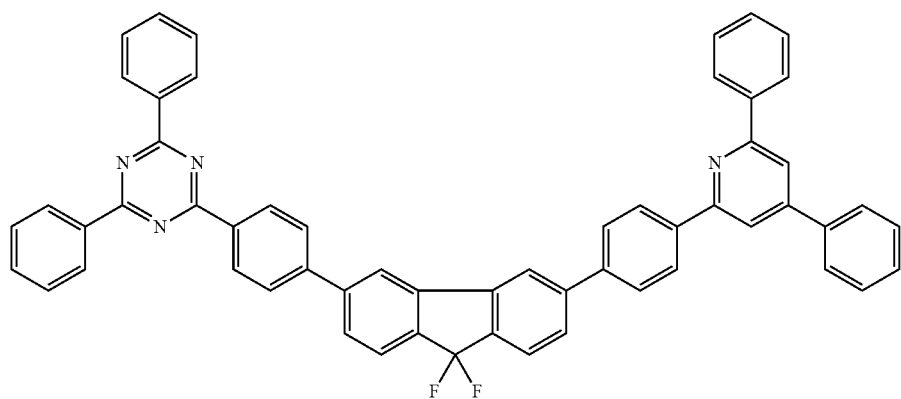

-continued
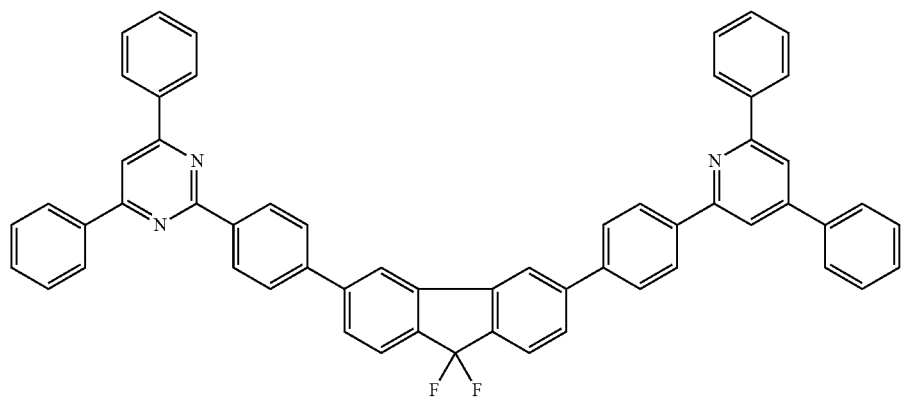
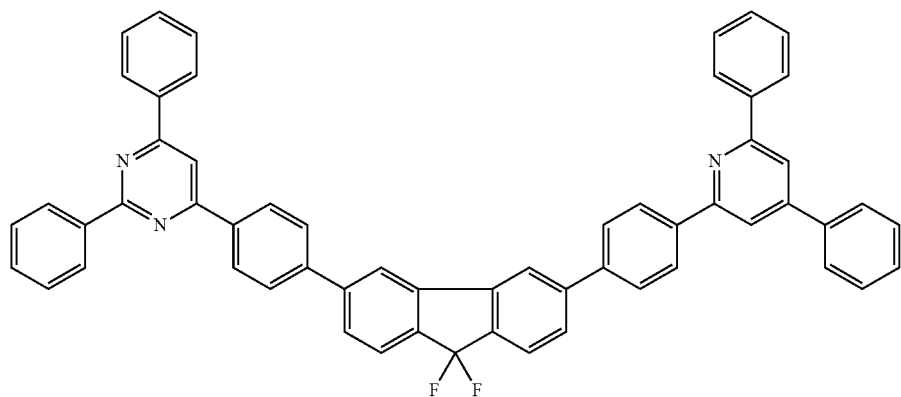
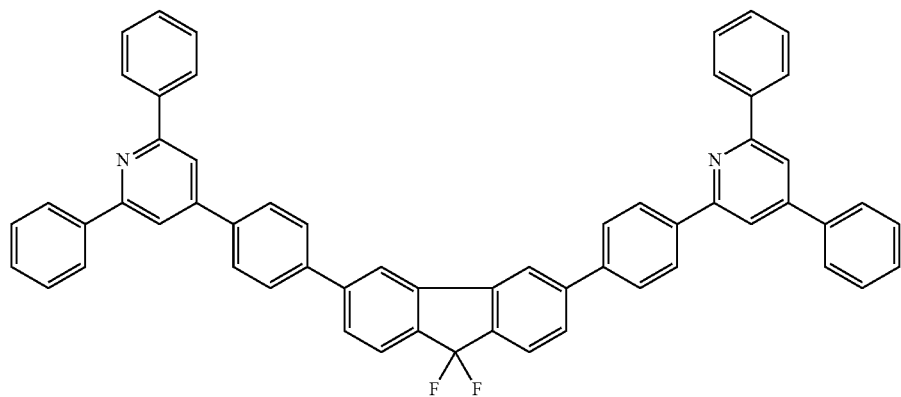
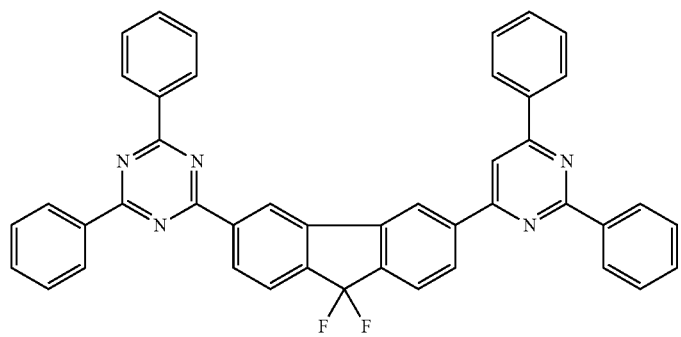

-continued
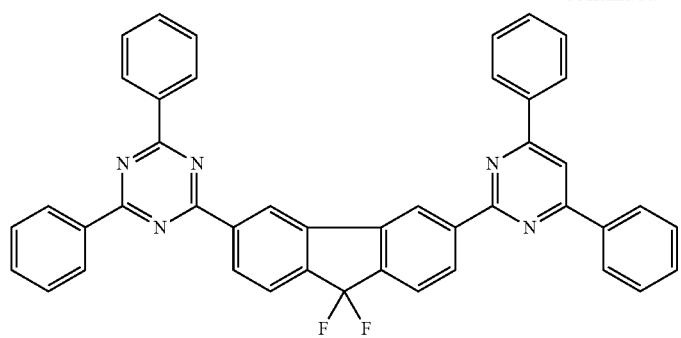
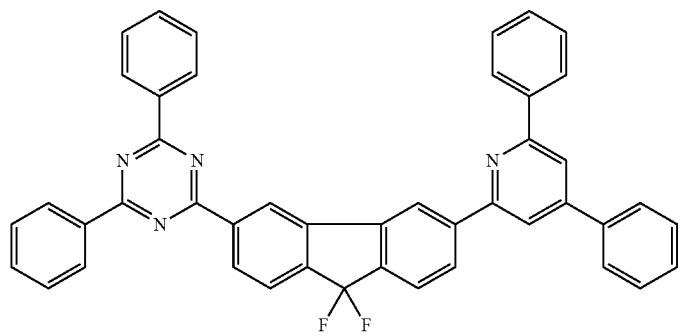
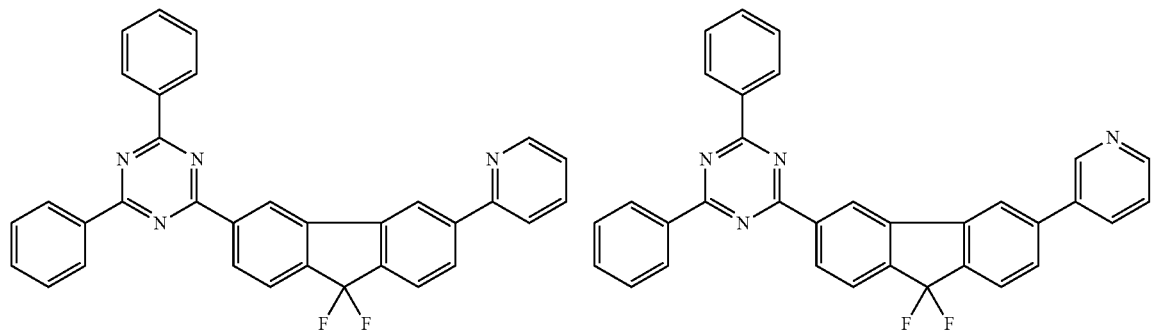
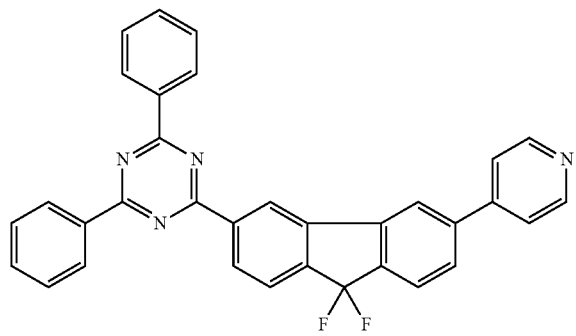
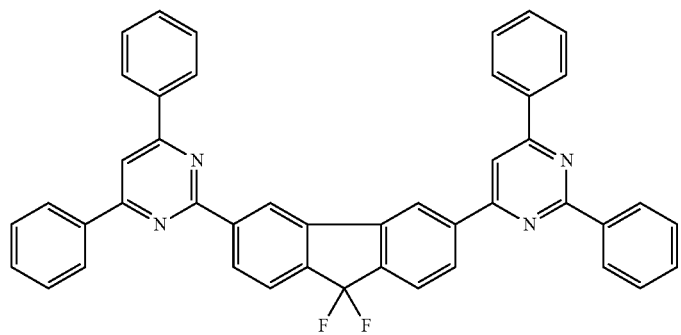

-continued
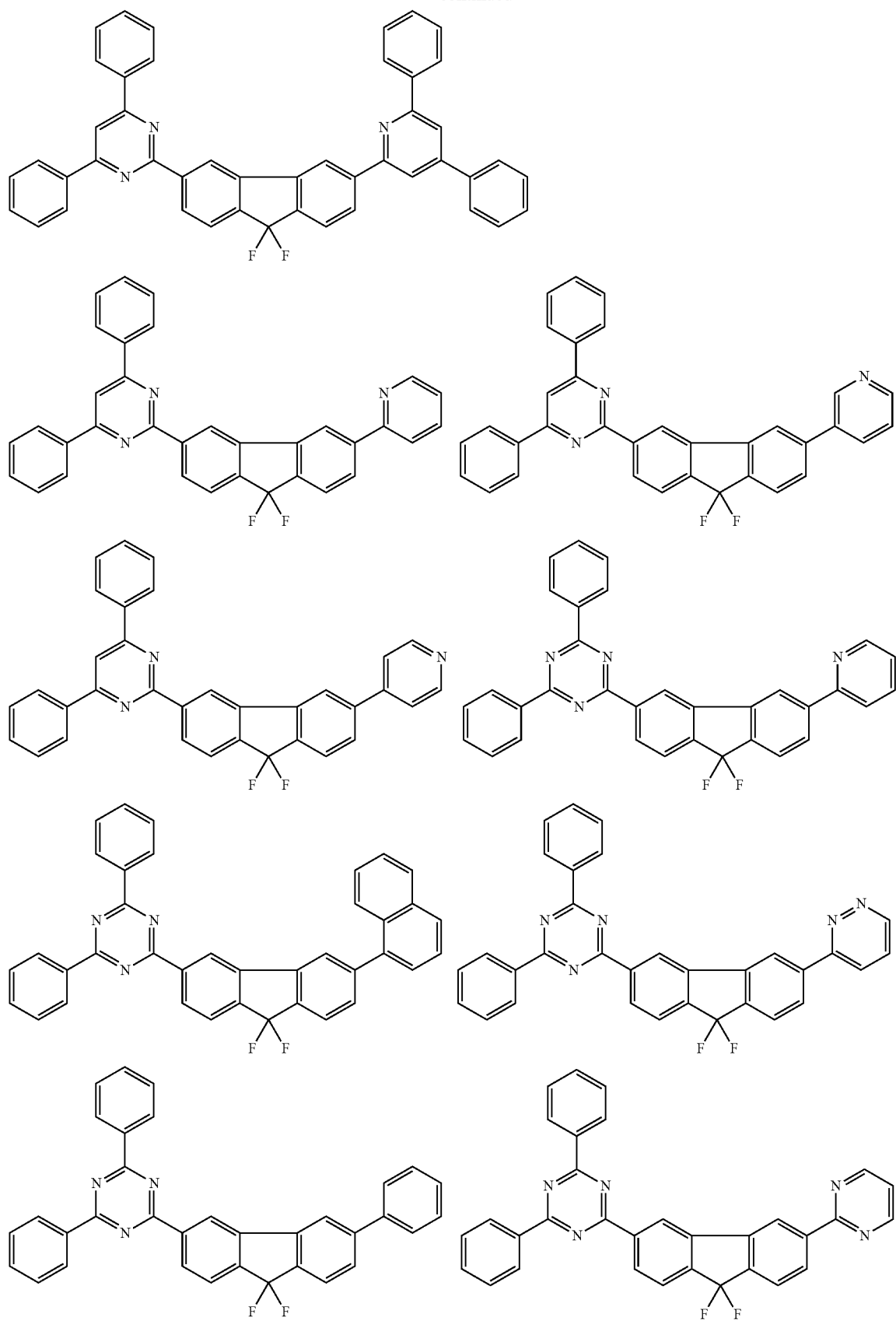

-continued
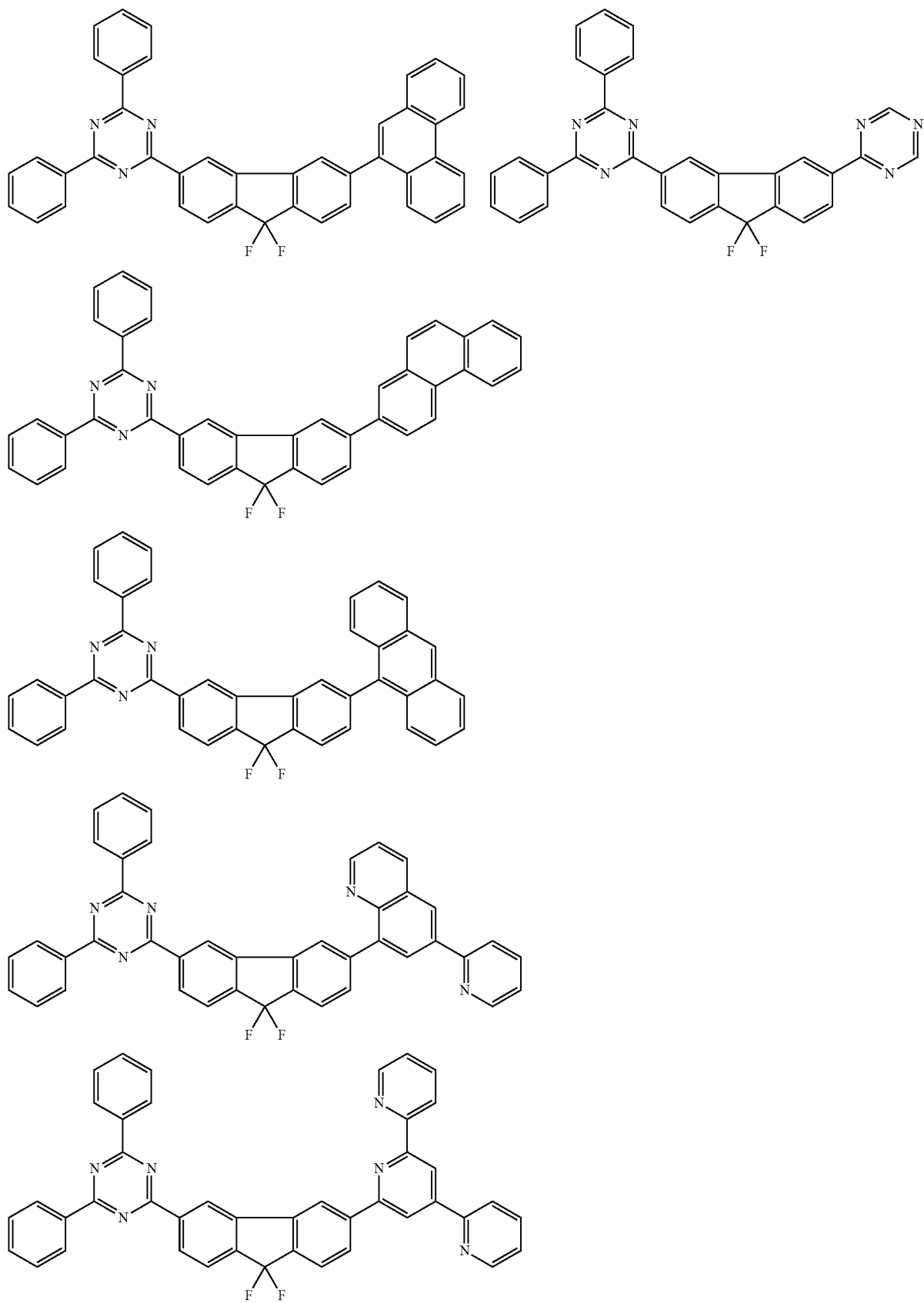

-continued
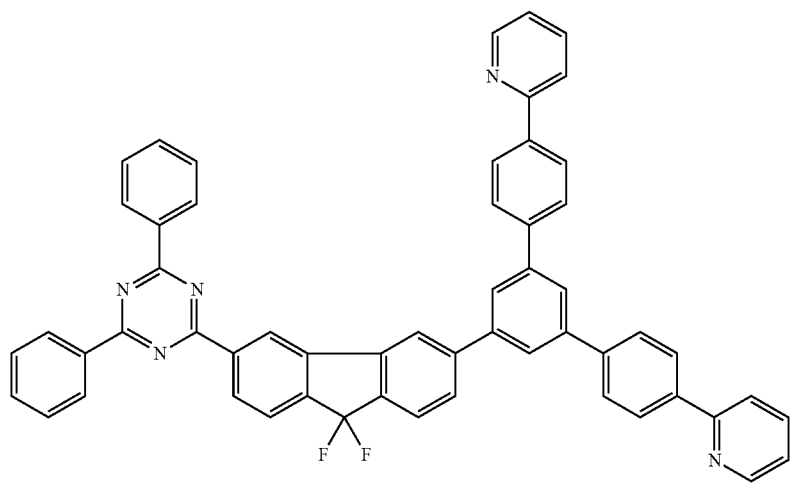
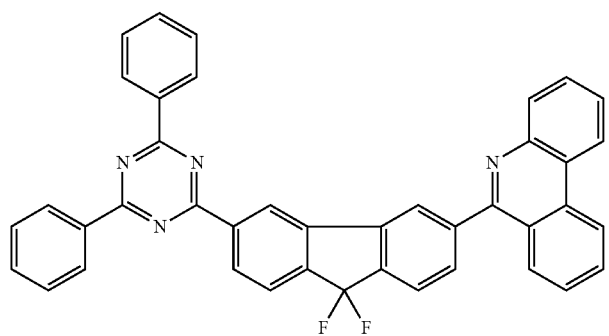
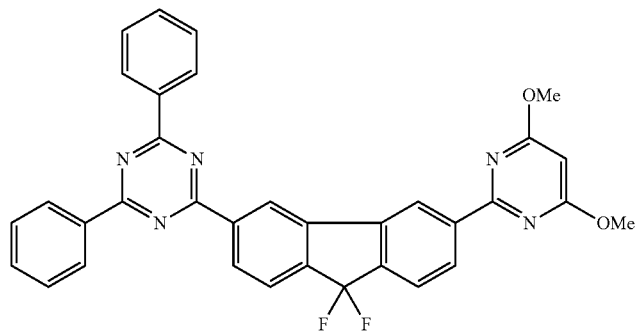
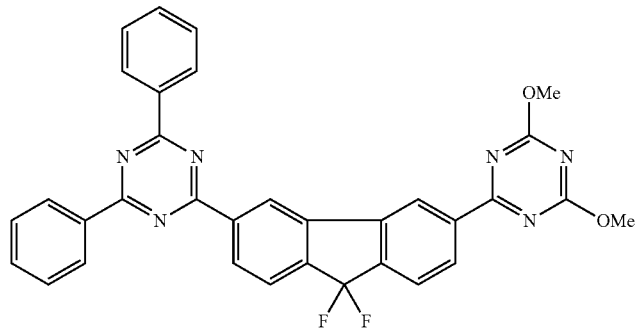

-continued
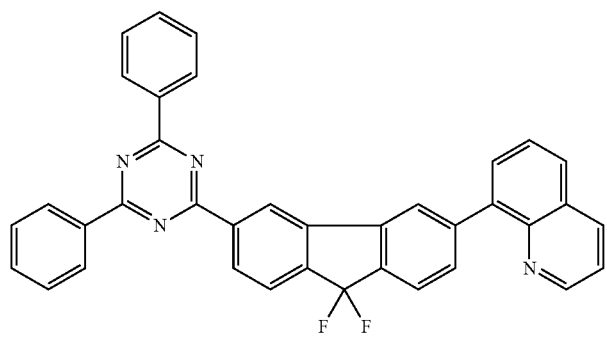
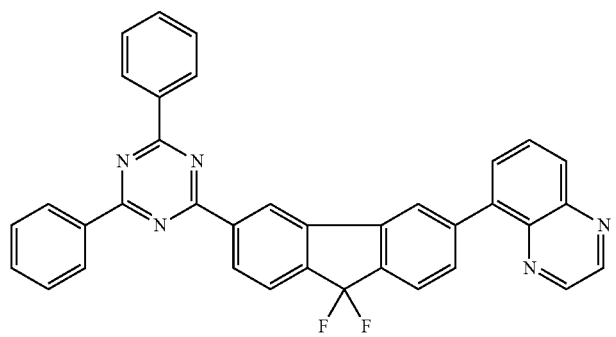
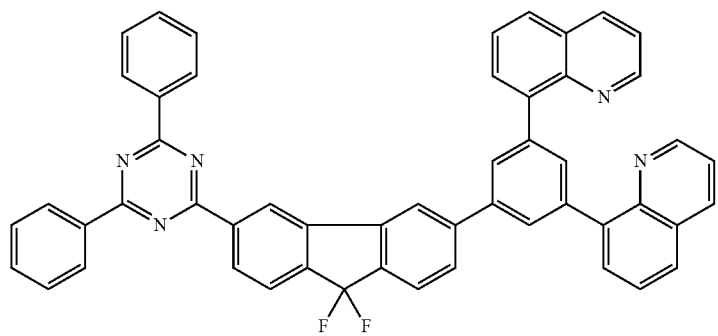
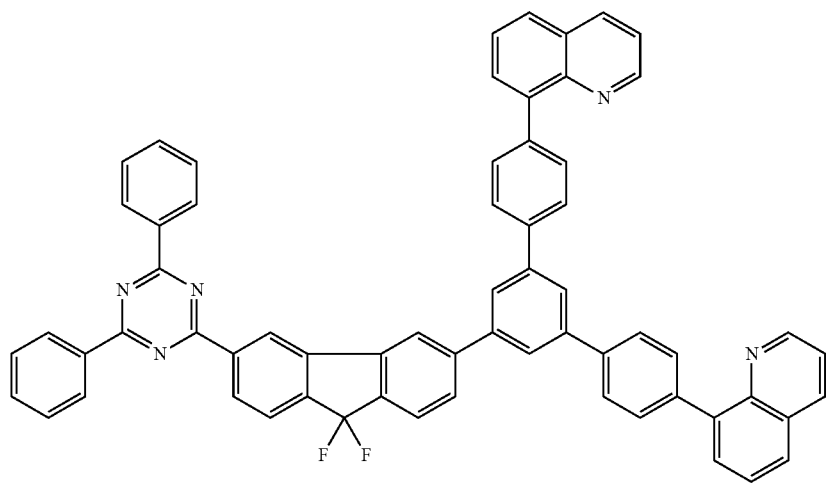

-continued
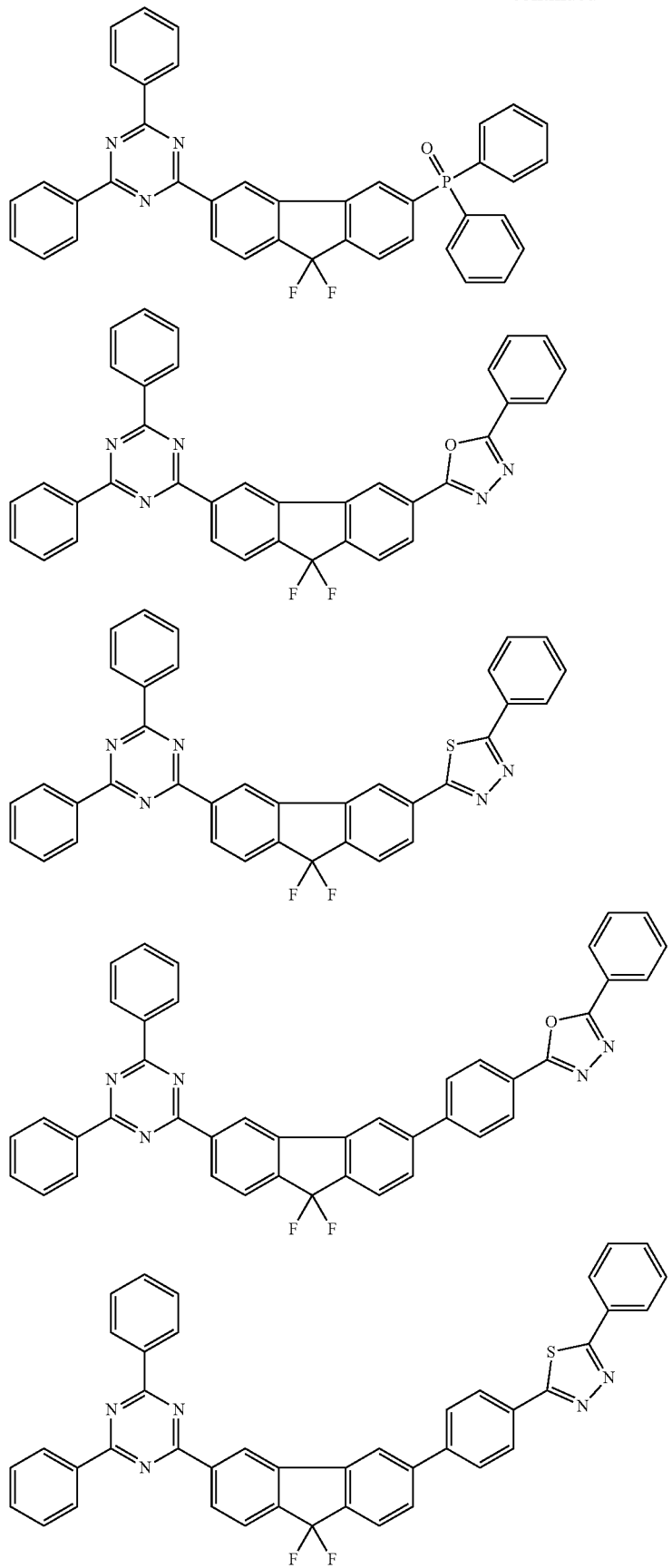

-continued
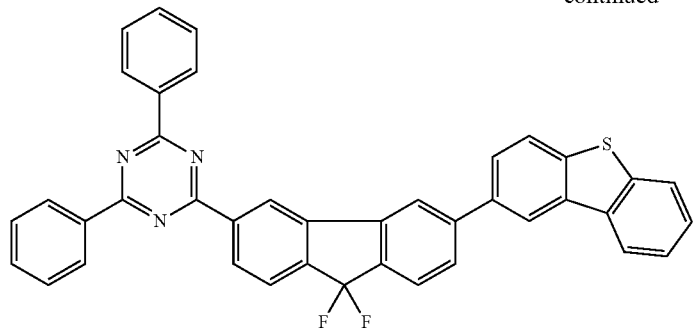
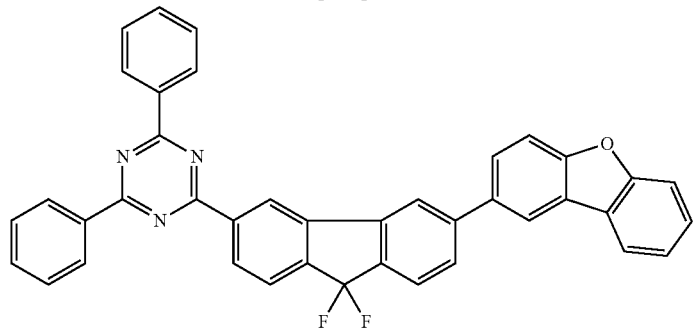
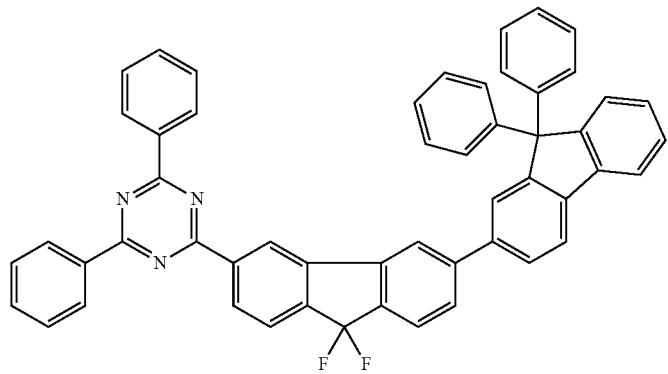
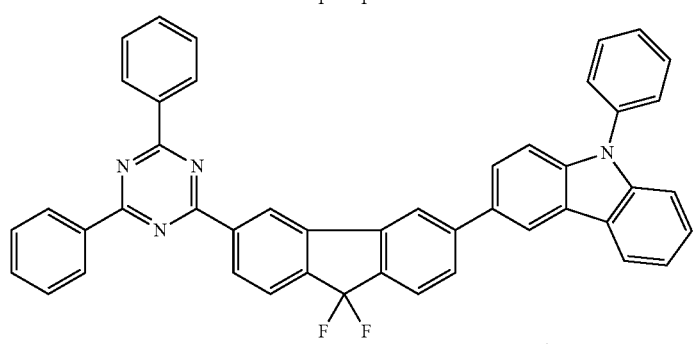
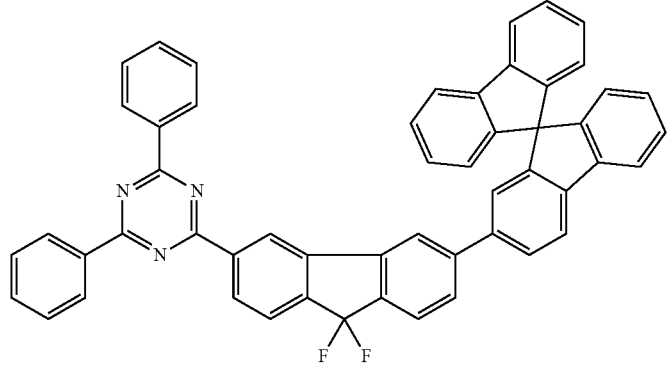

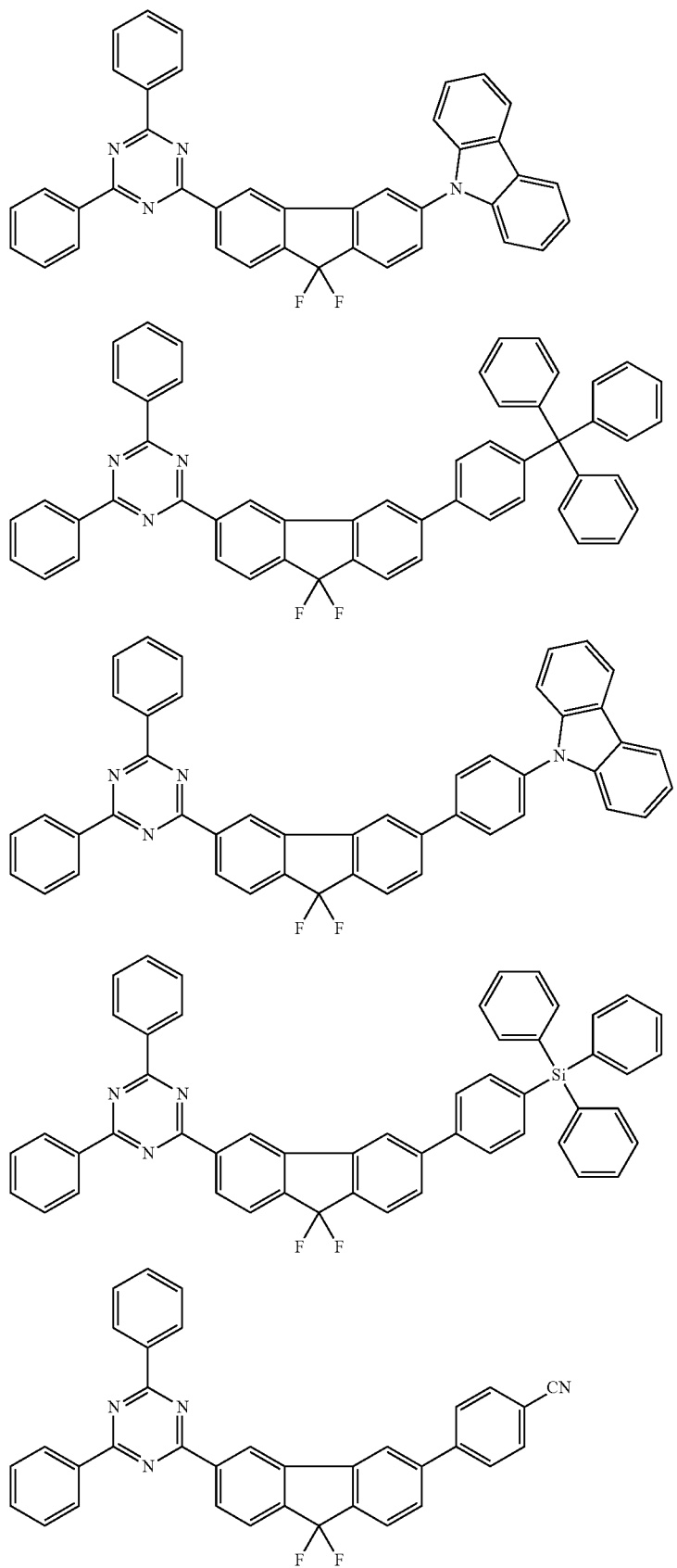

-continued
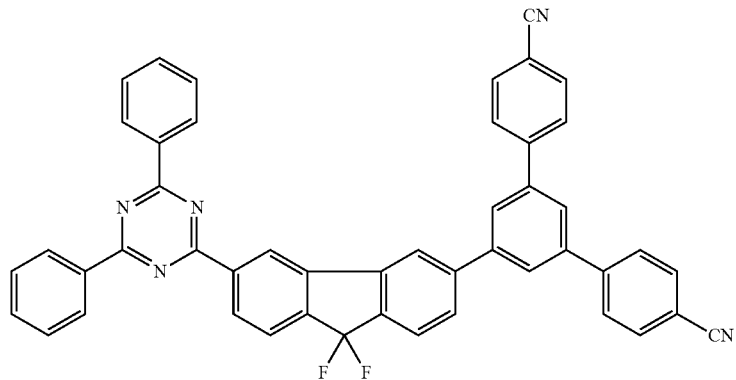
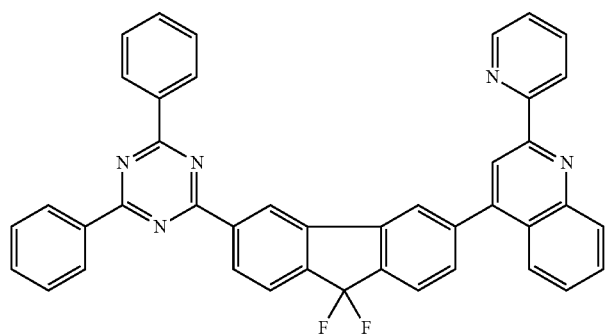
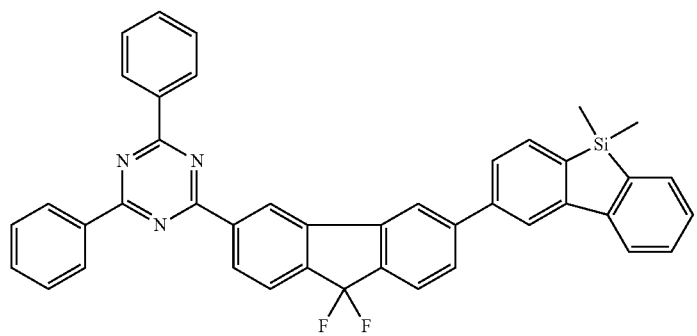
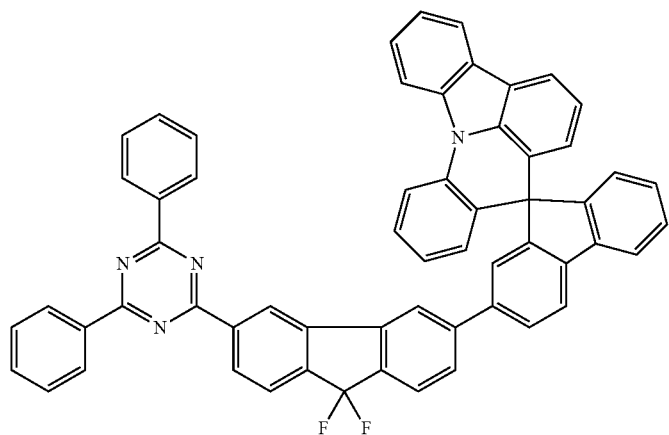

-continued
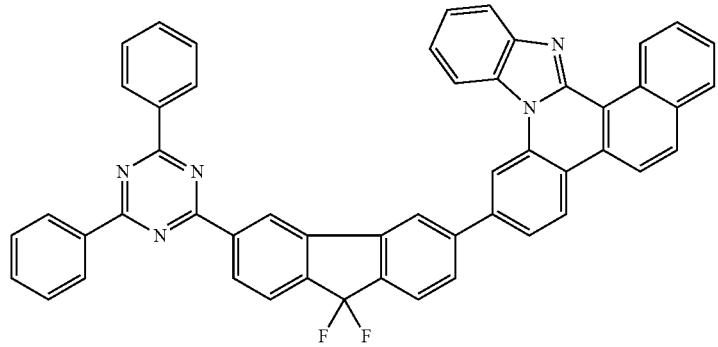
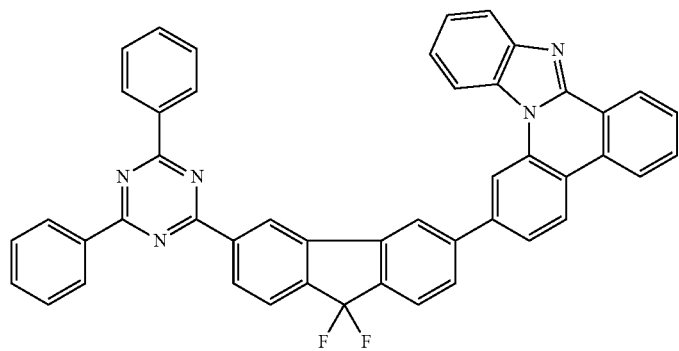
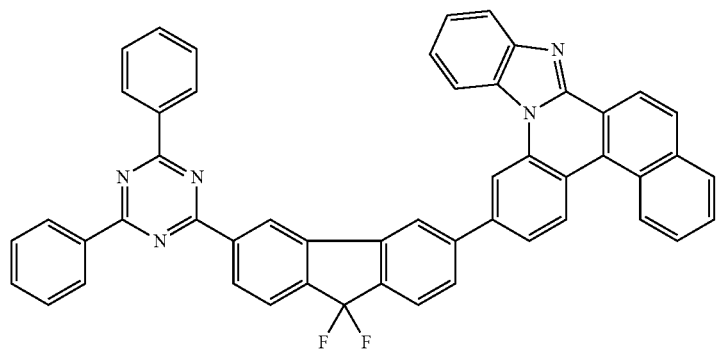
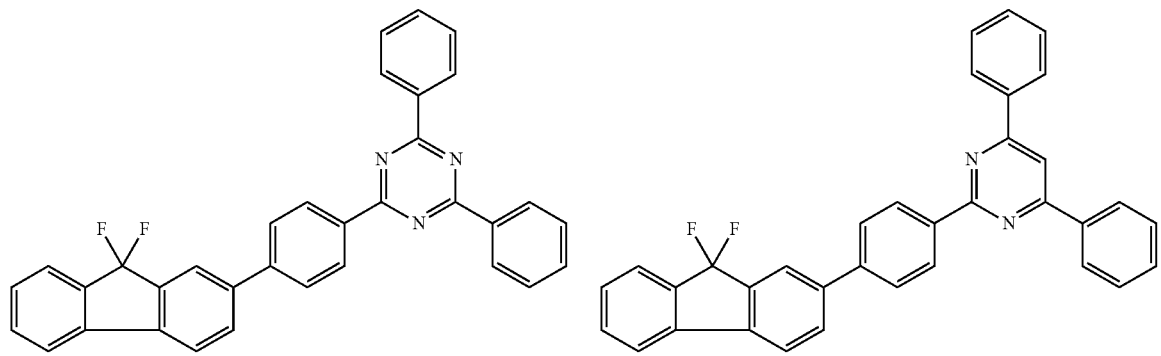

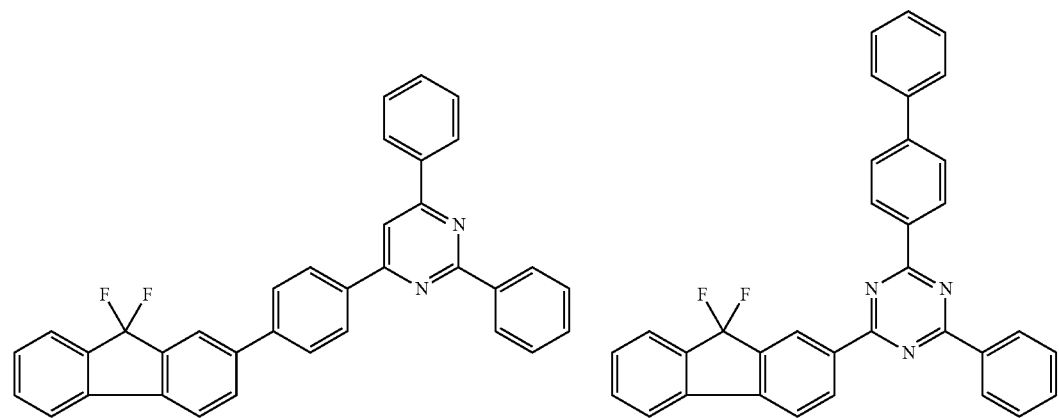
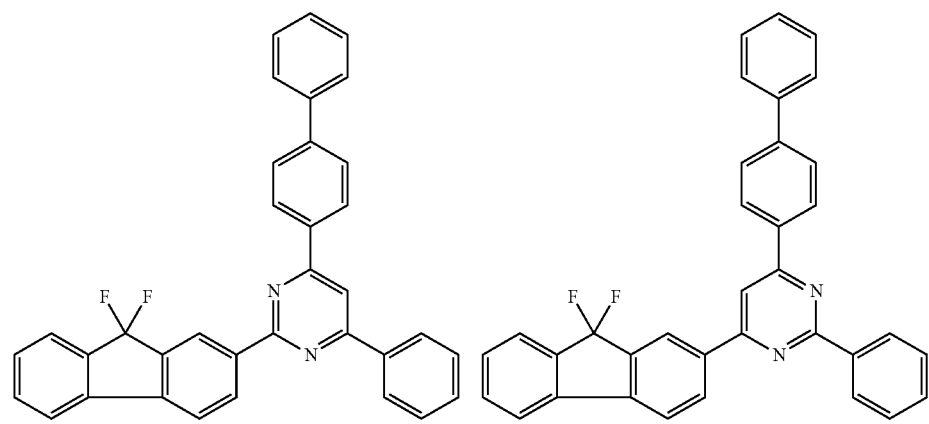
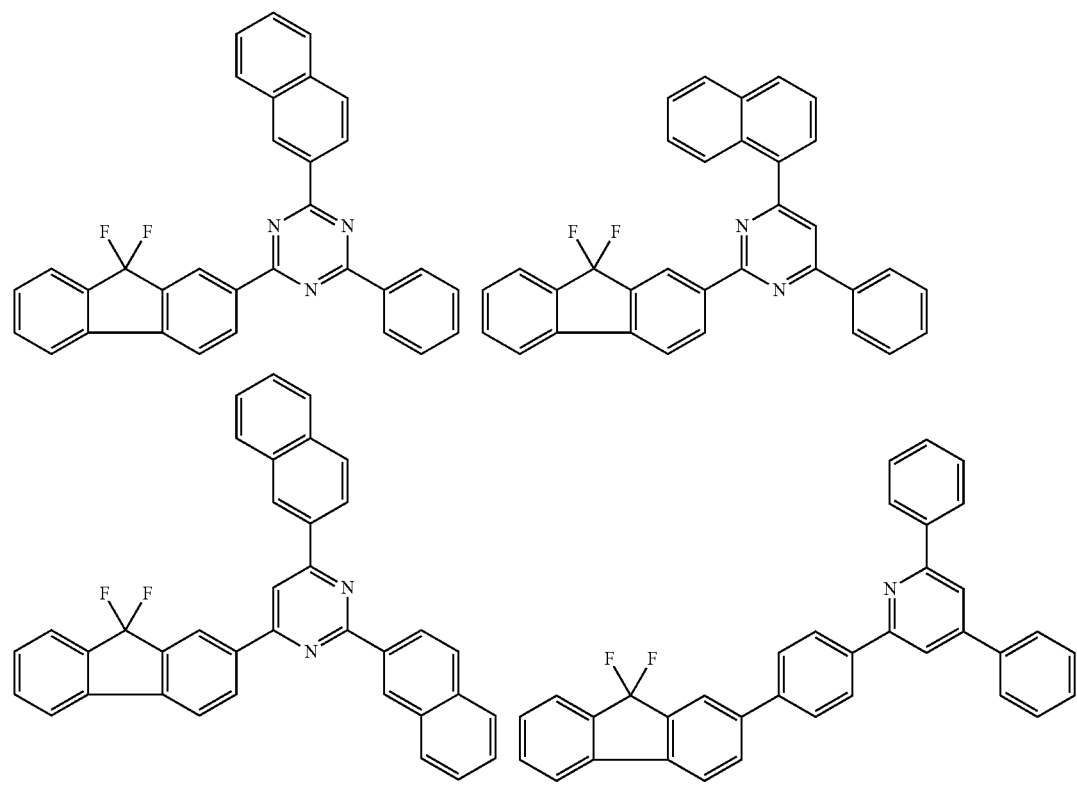

-continued
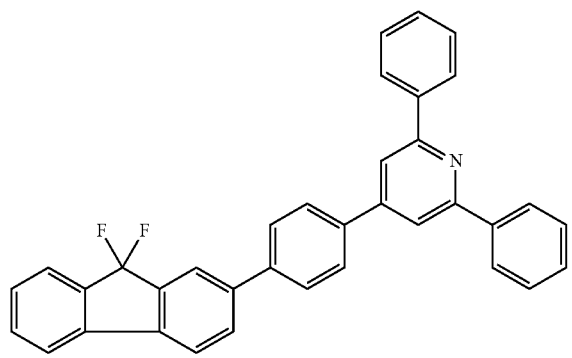 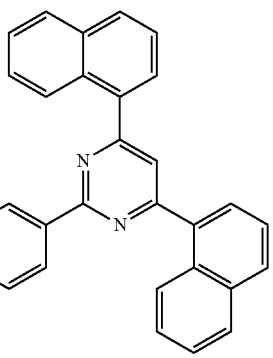
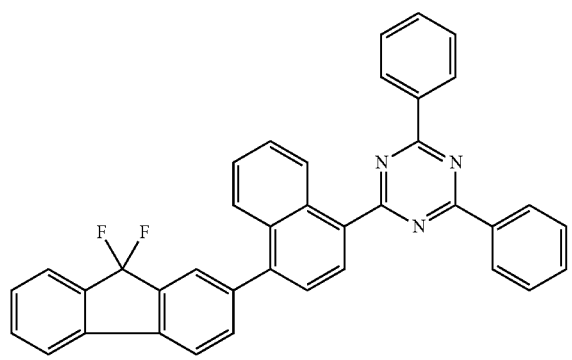 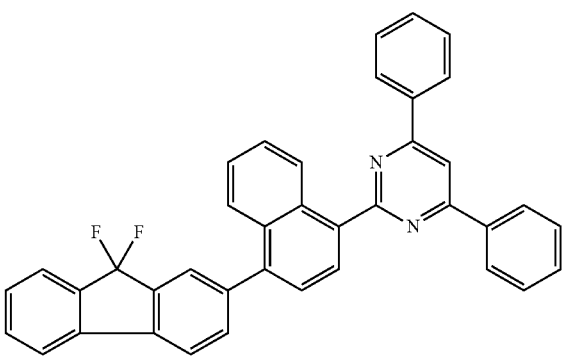
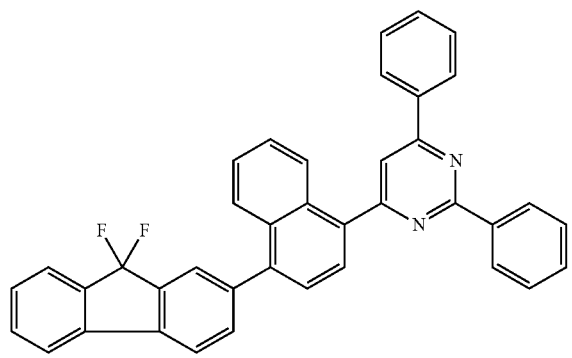 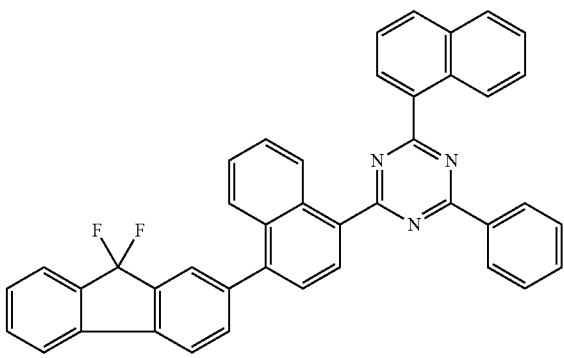
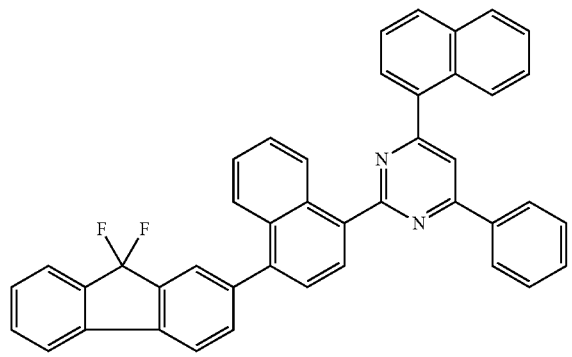 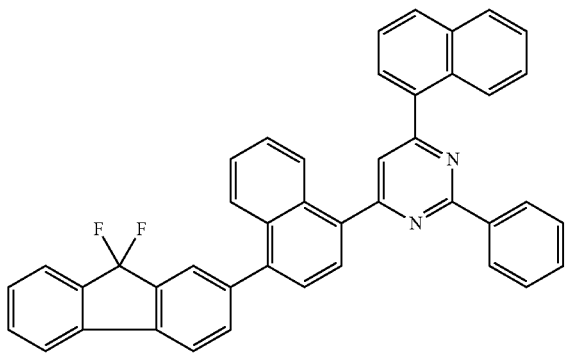

-continued
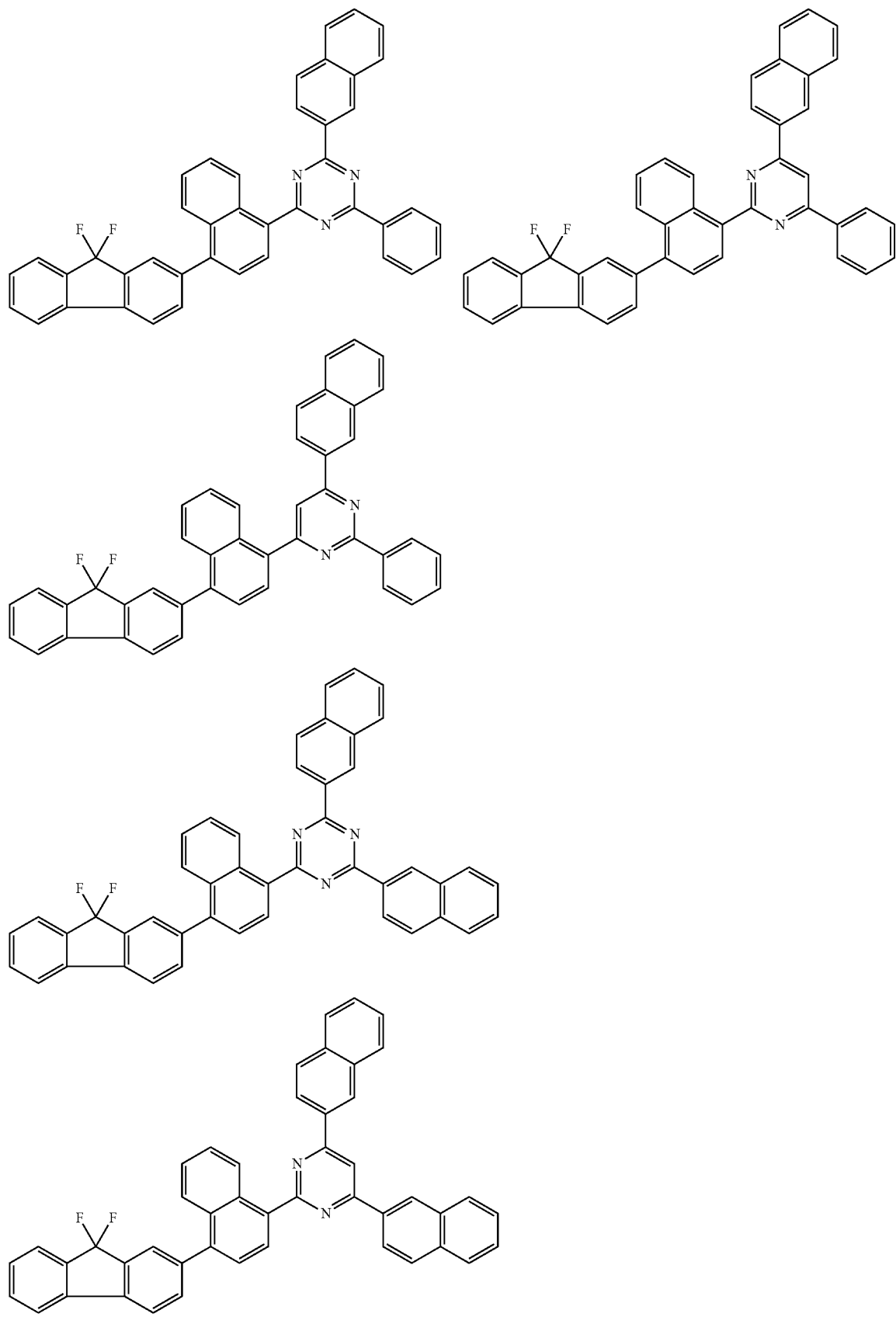

-continued
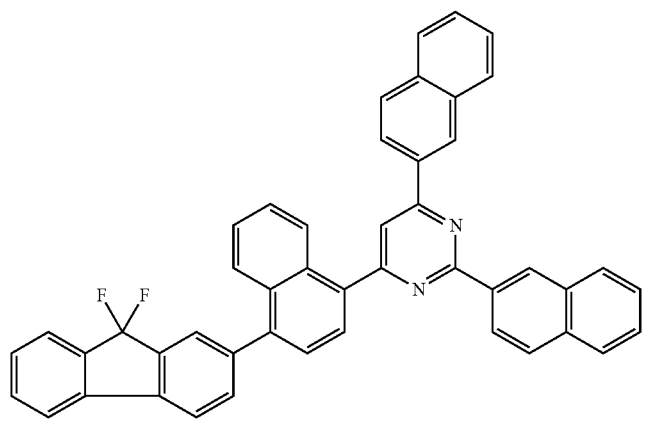
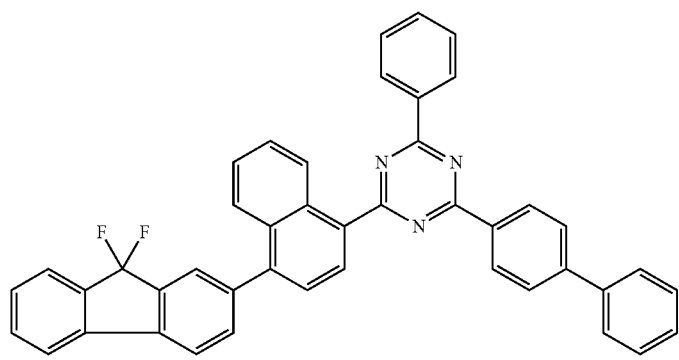
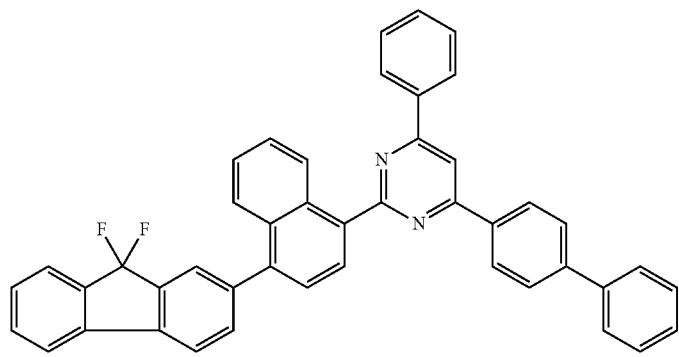
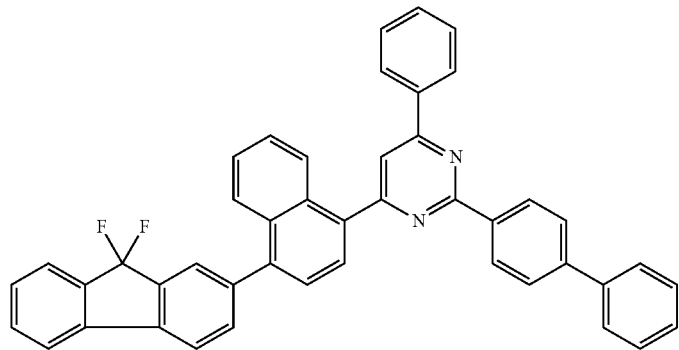

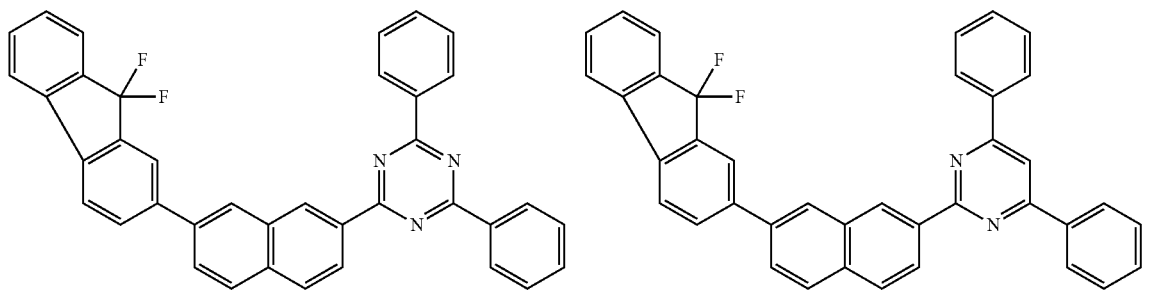
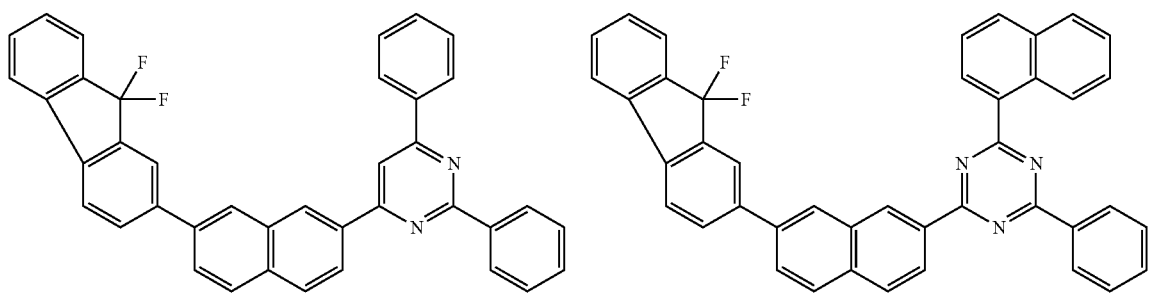
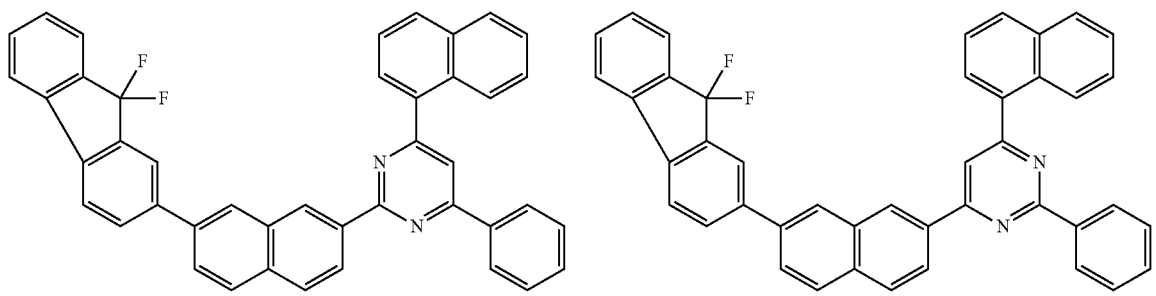
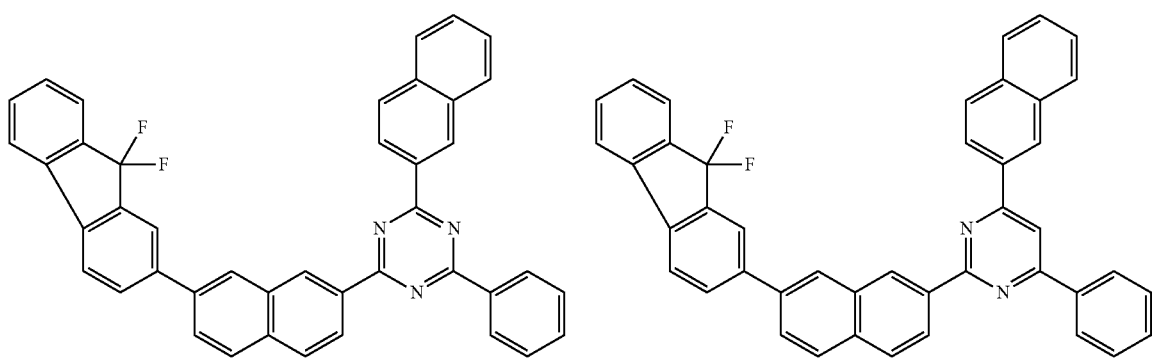
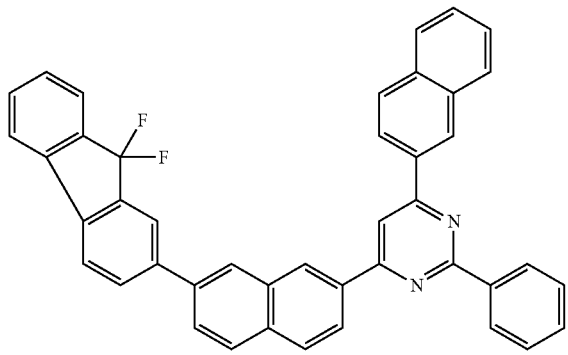

-continued
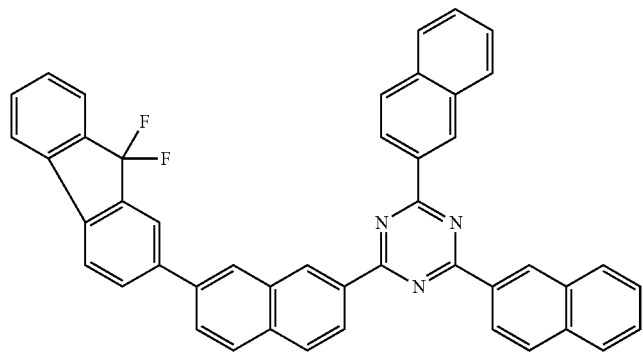
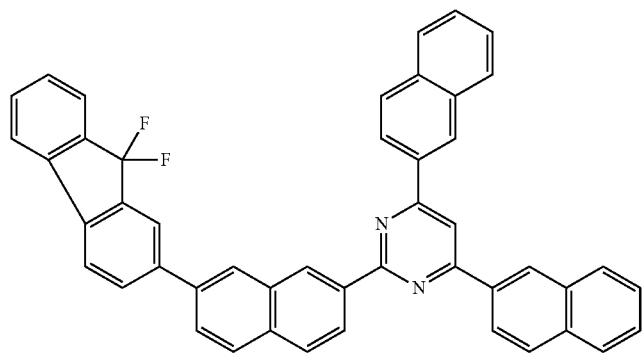
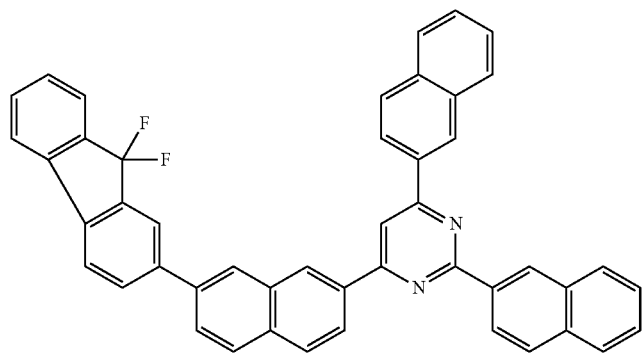
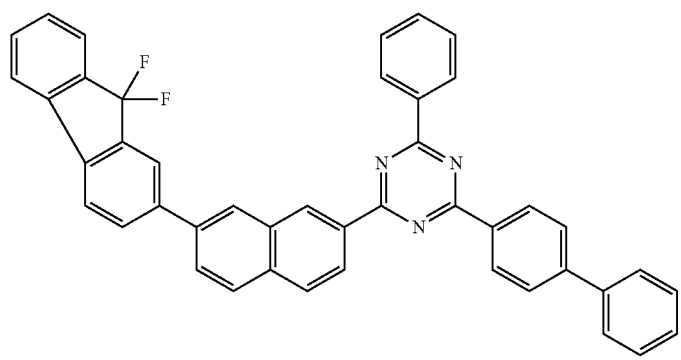

-continued
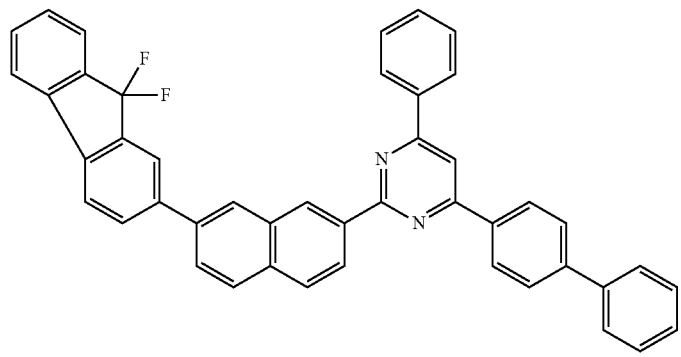
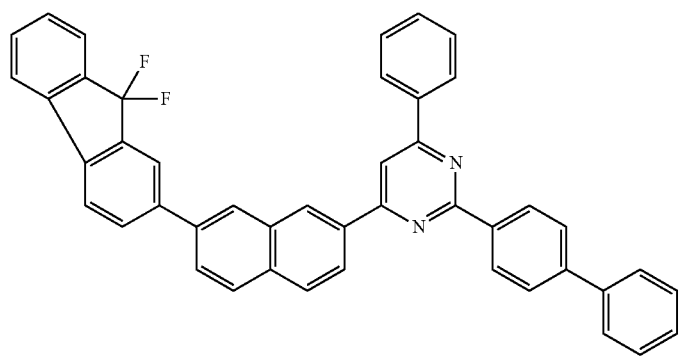
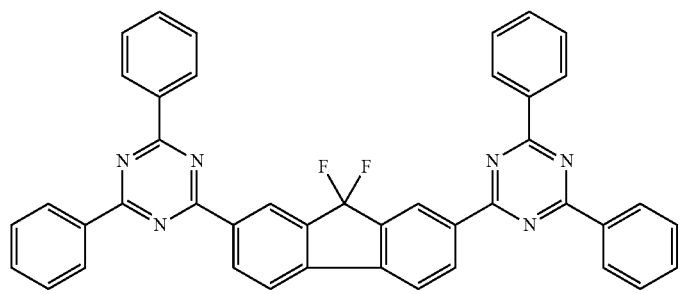
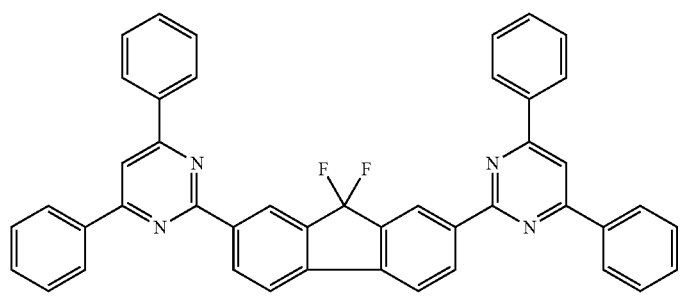
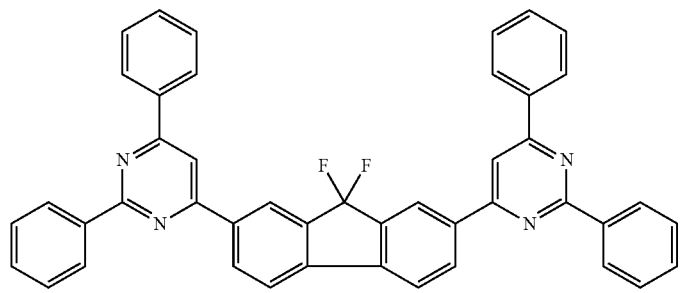

-continued
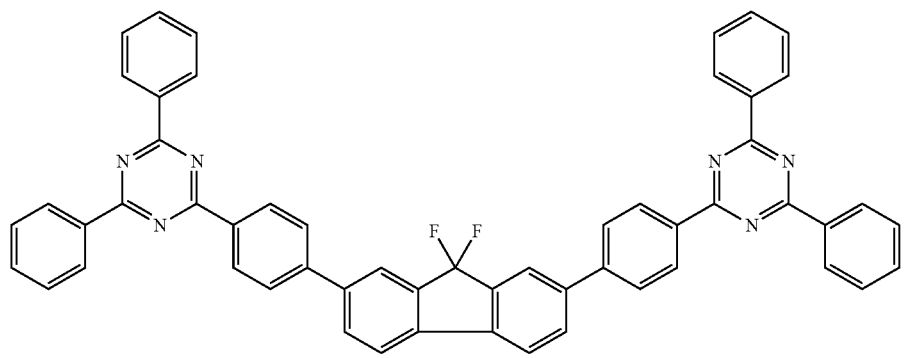
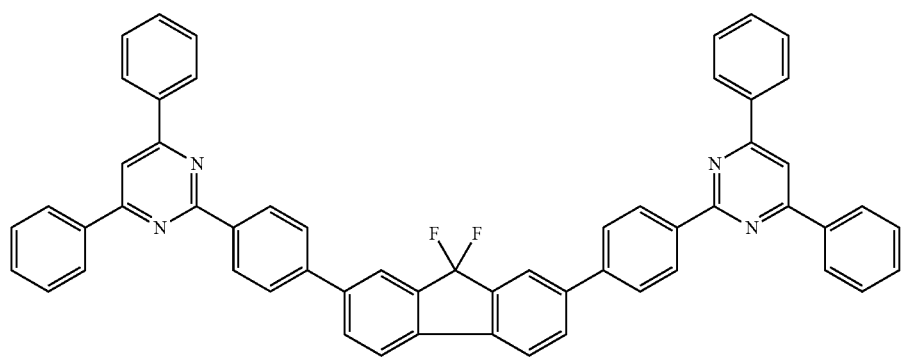
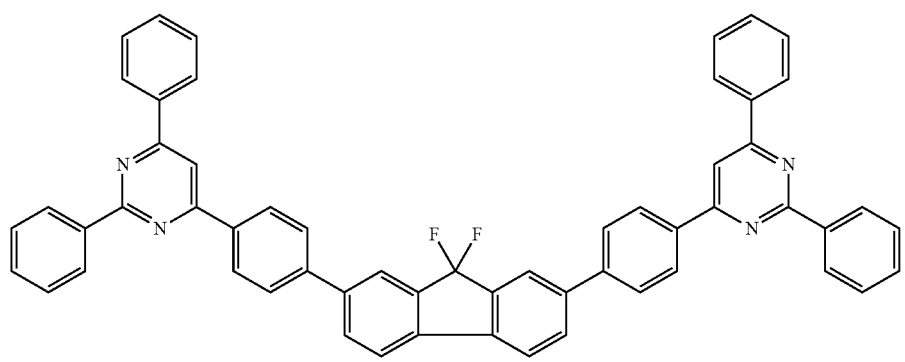
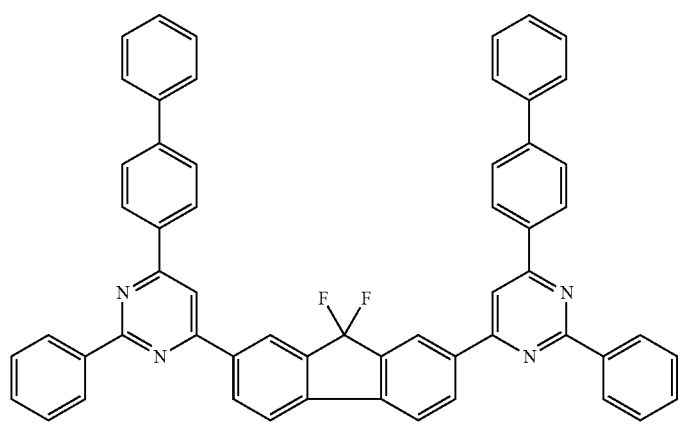

-continued
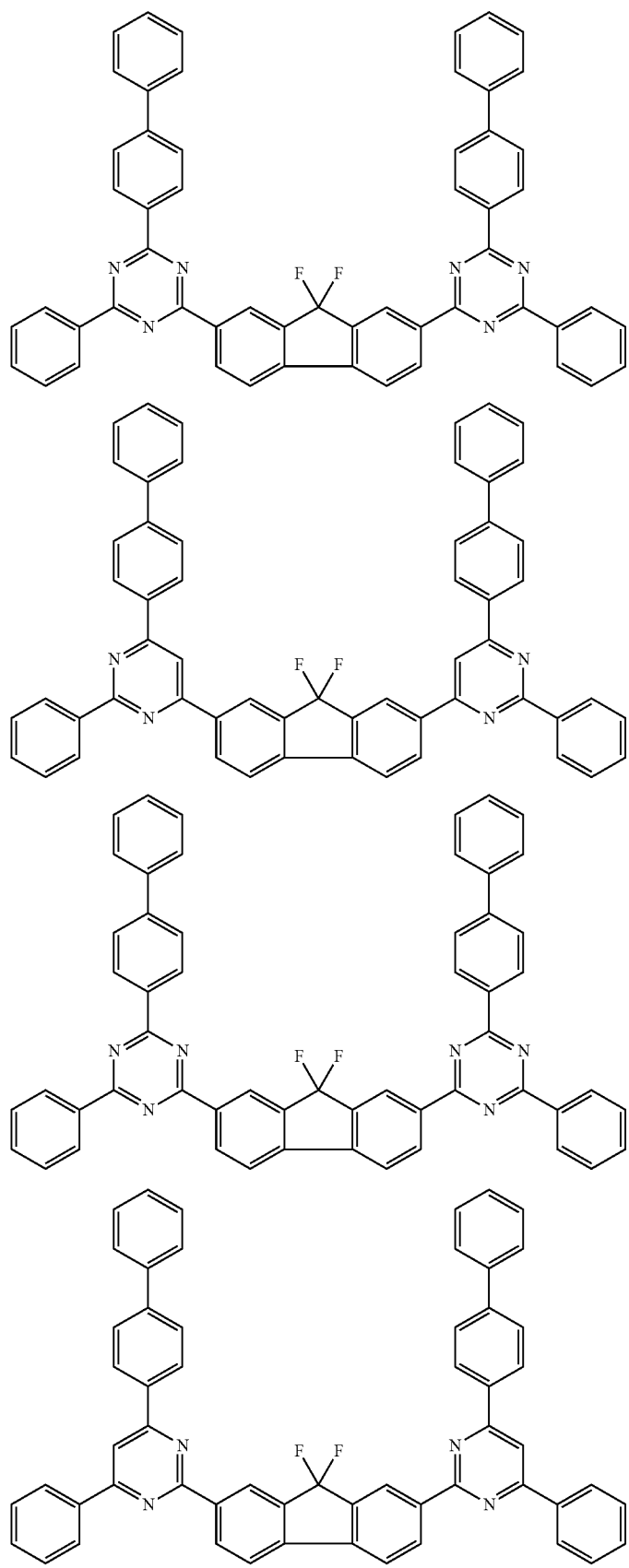

-continued
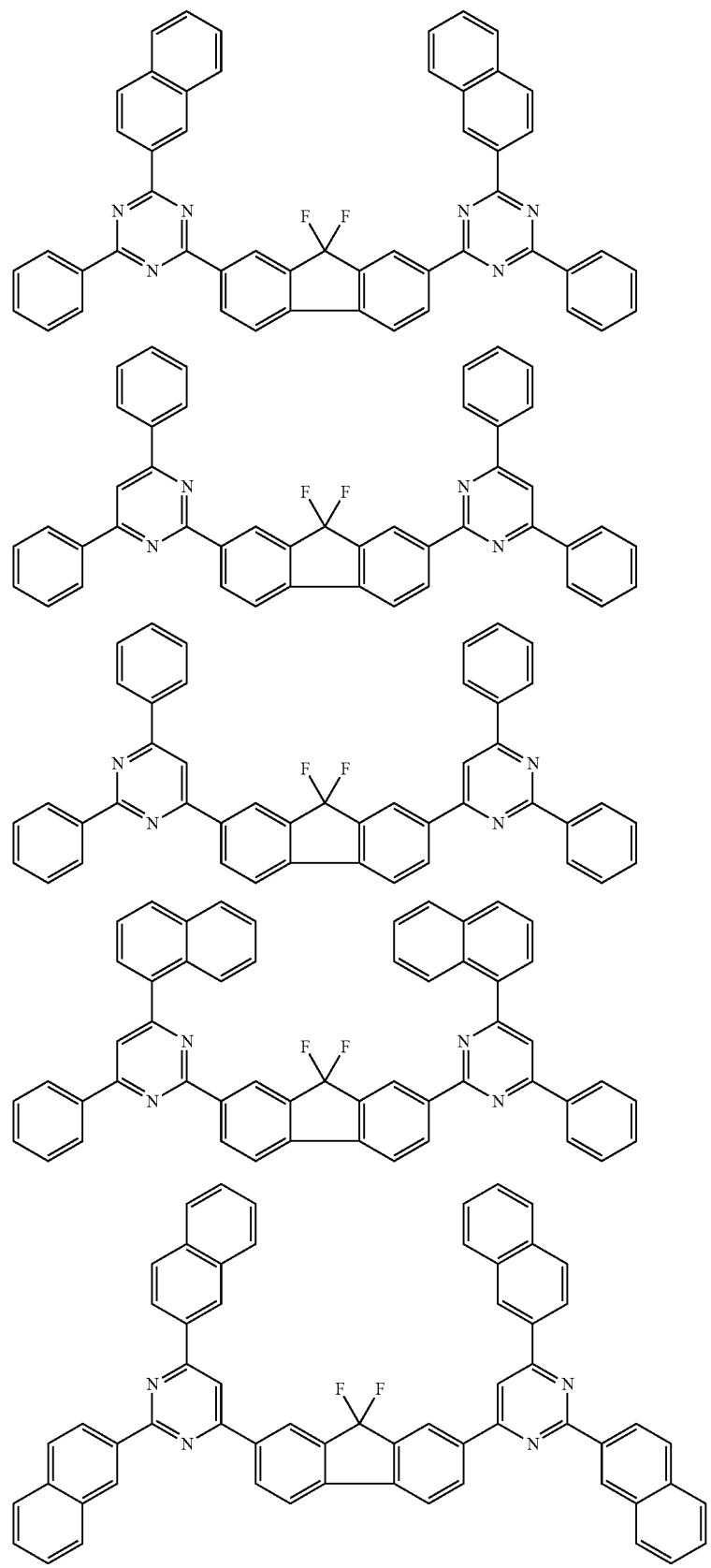

-continued
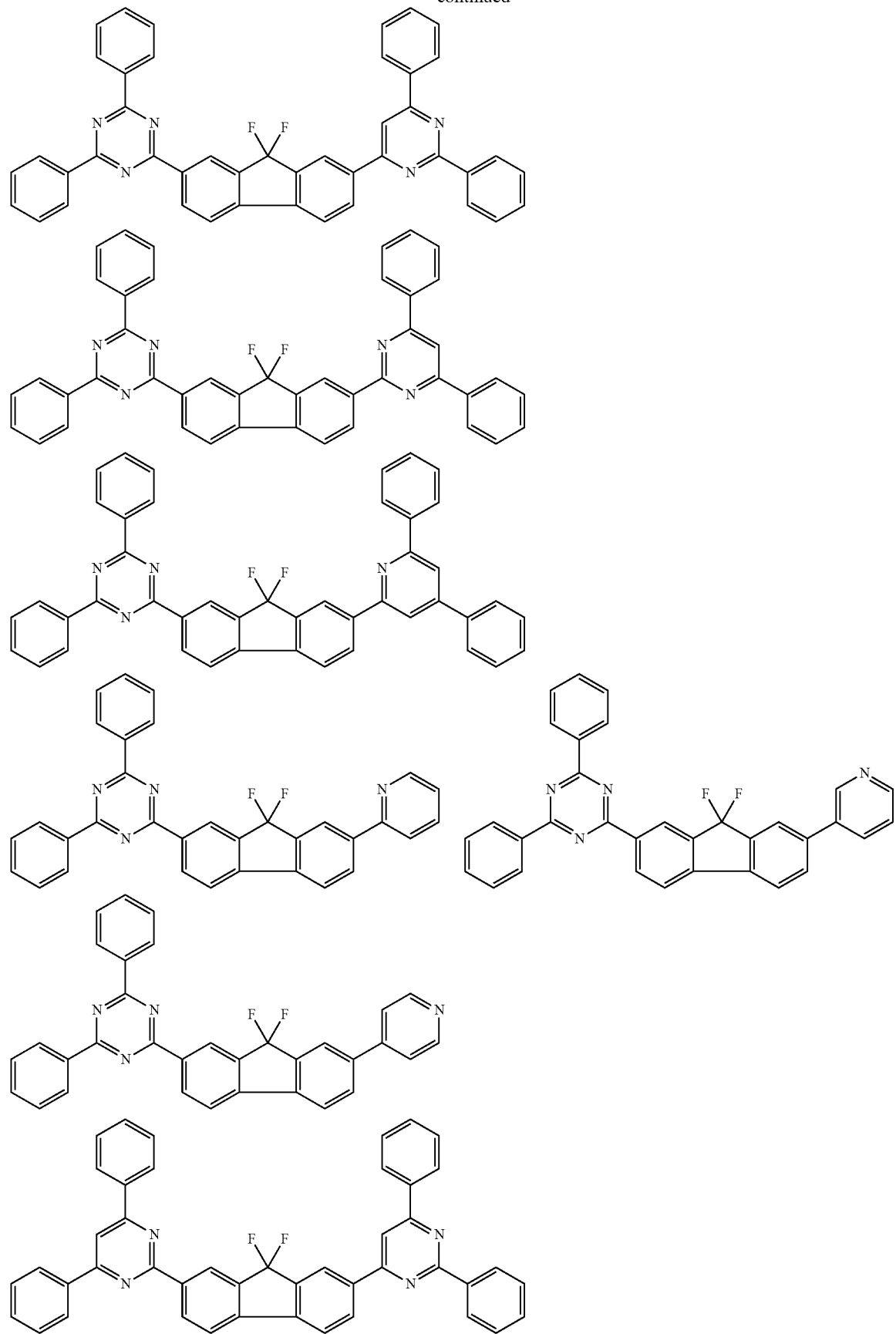

-continued
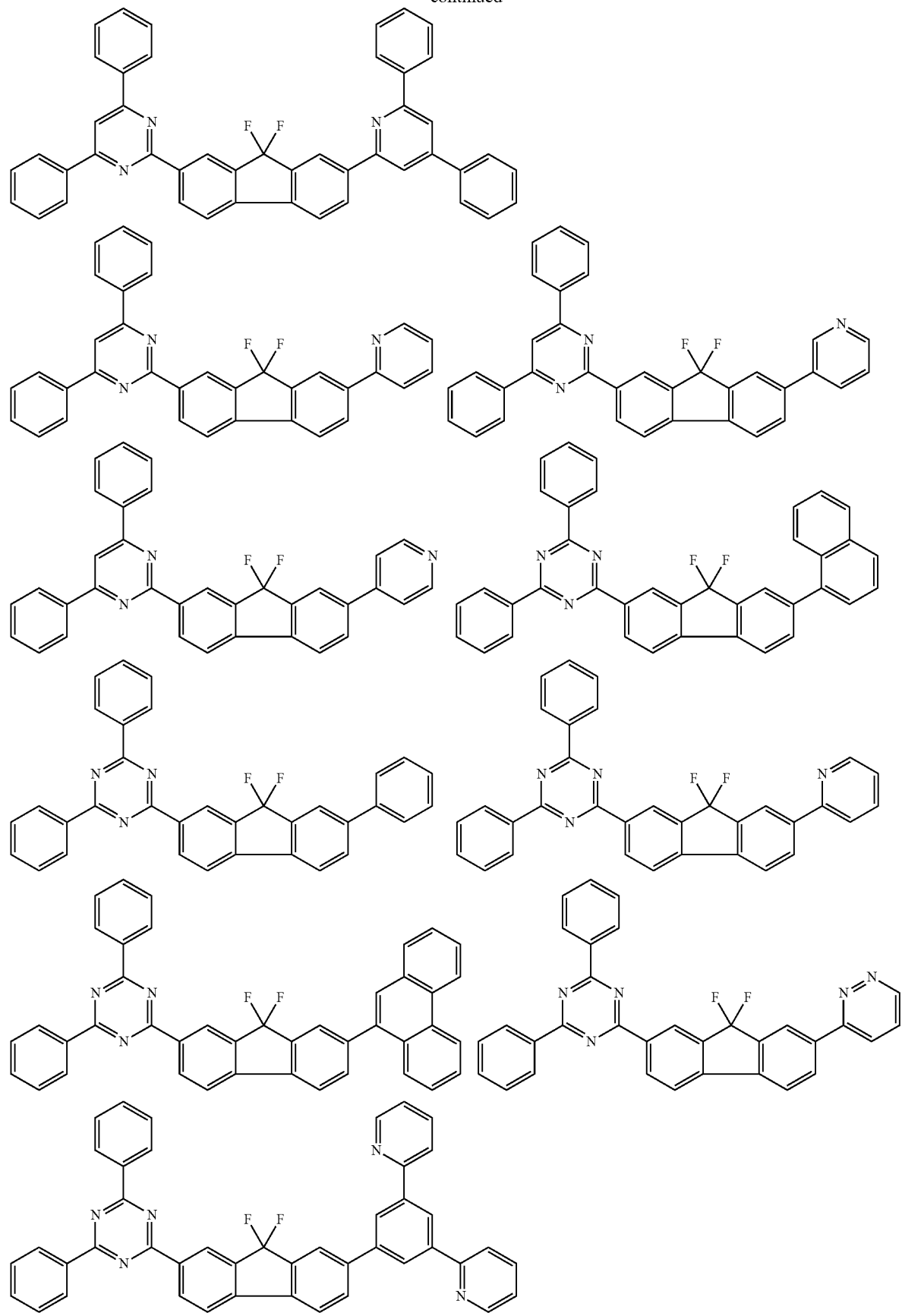

71
72
-continued
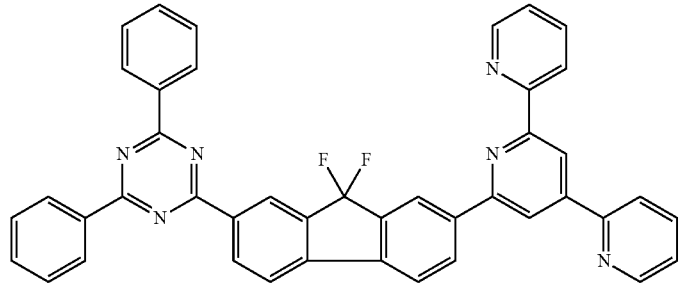
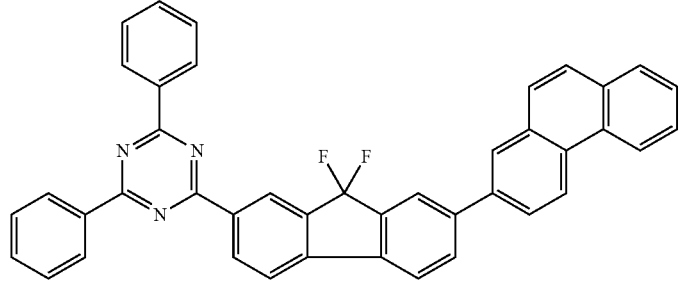
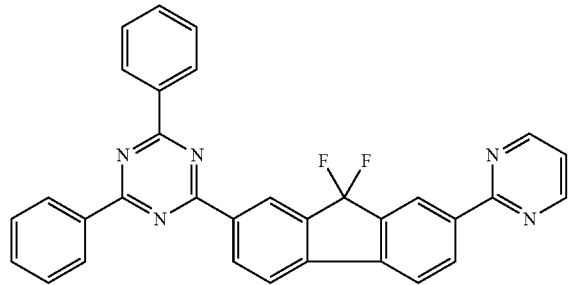
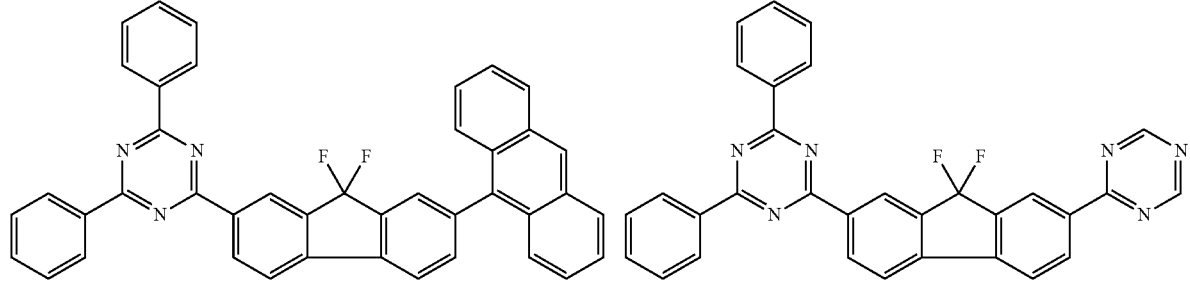
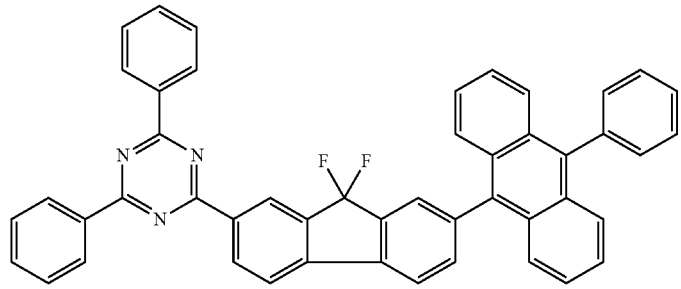
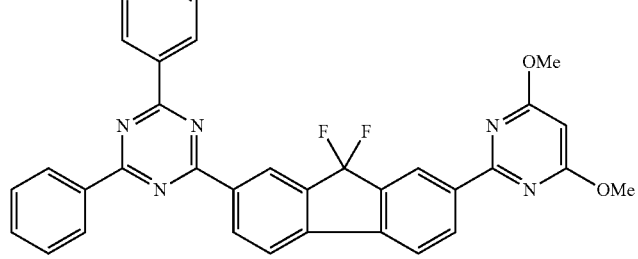

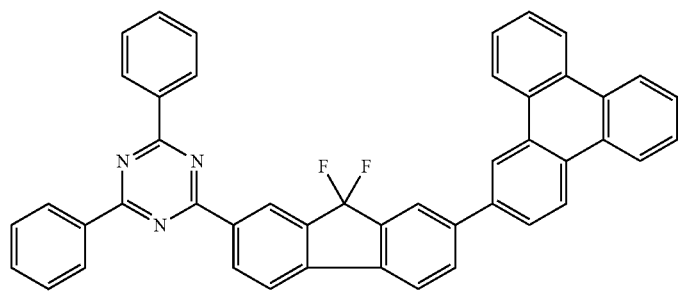
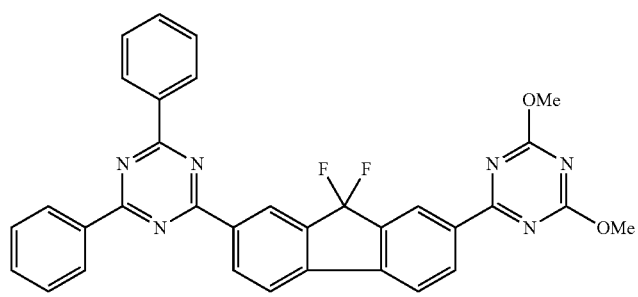
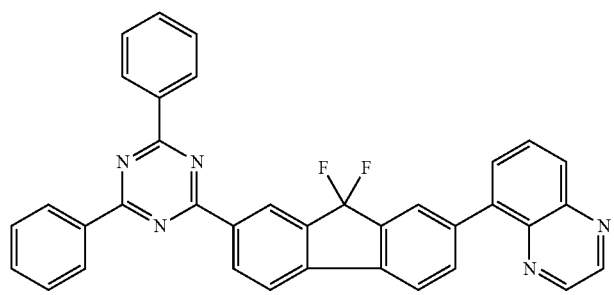
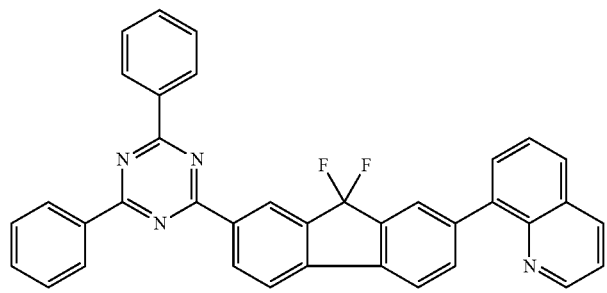
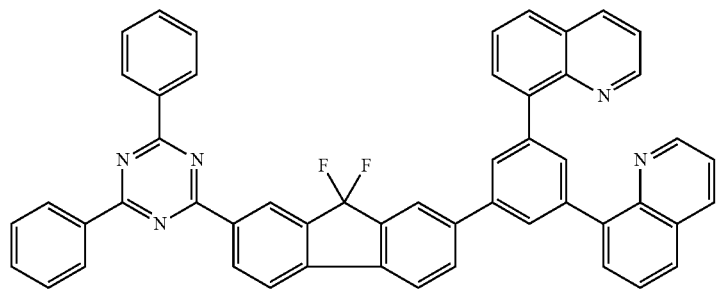

-continued
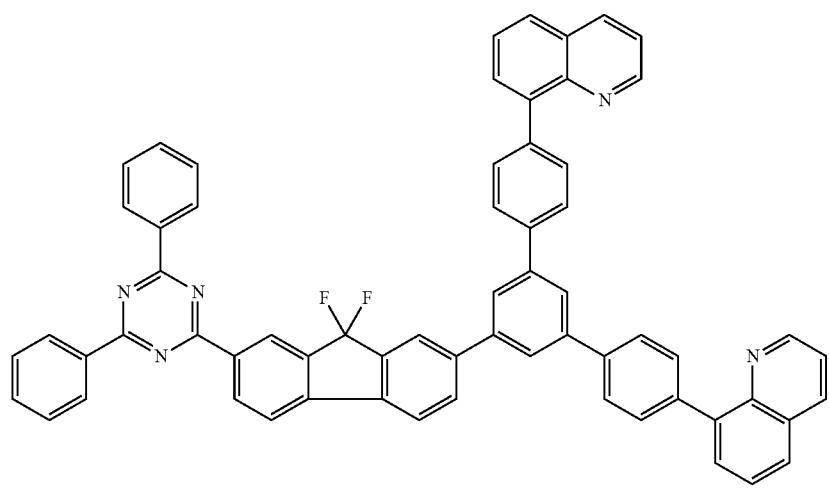
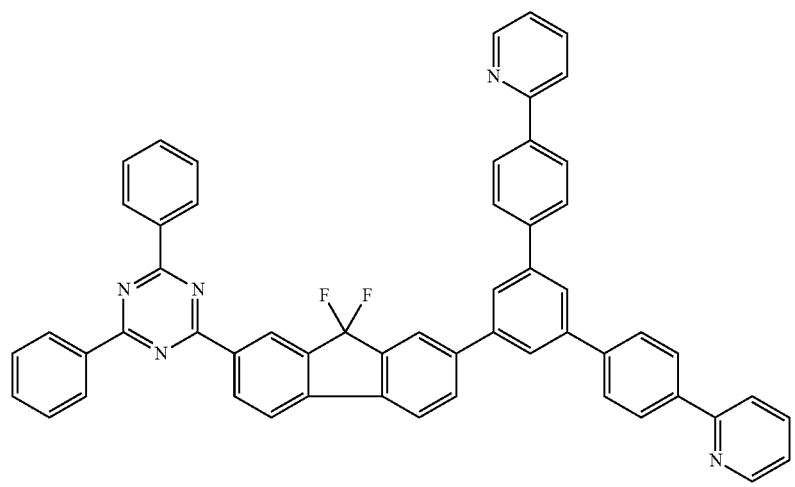
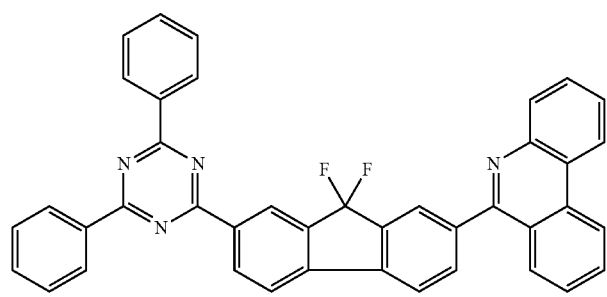
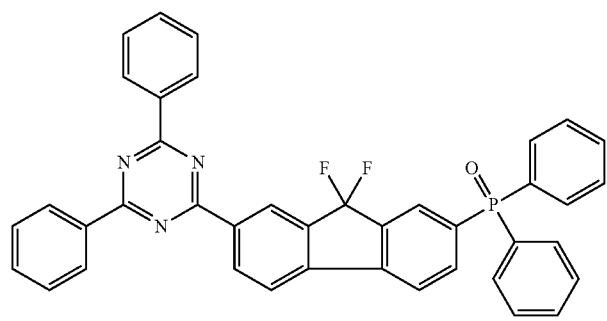

-continued
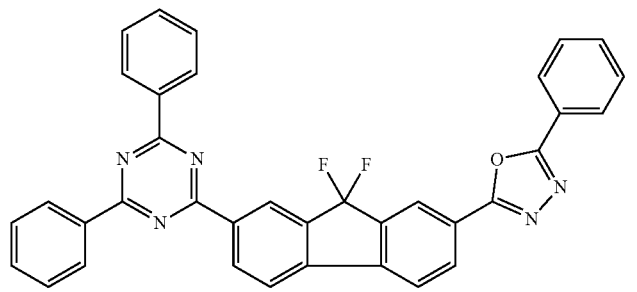
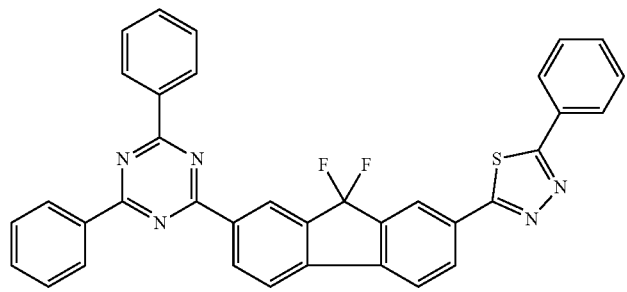
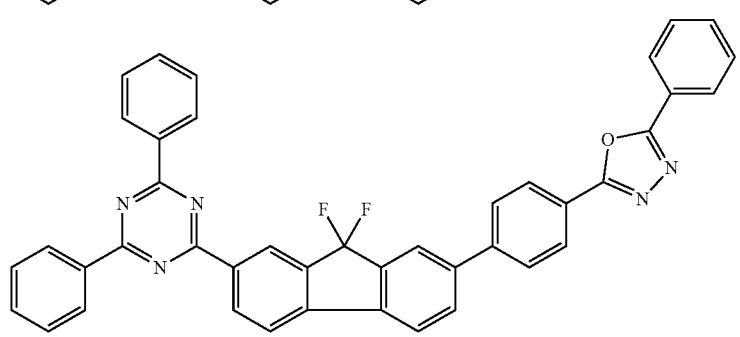
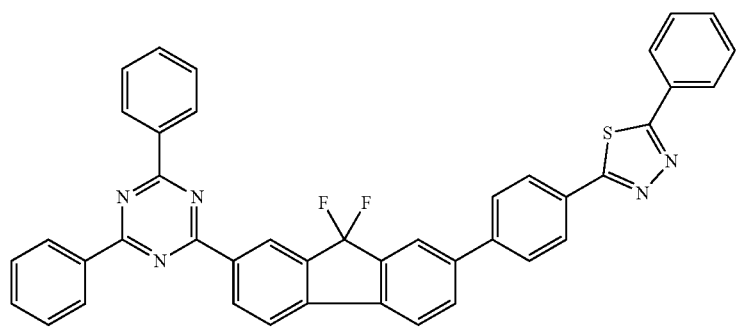
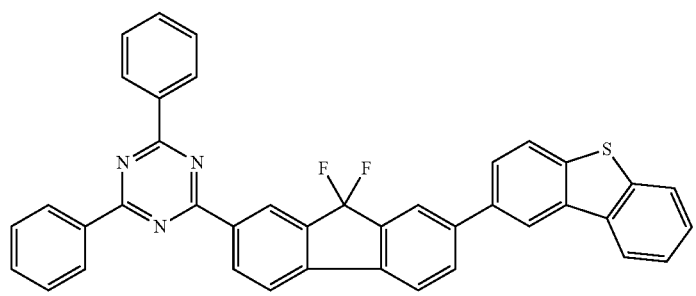

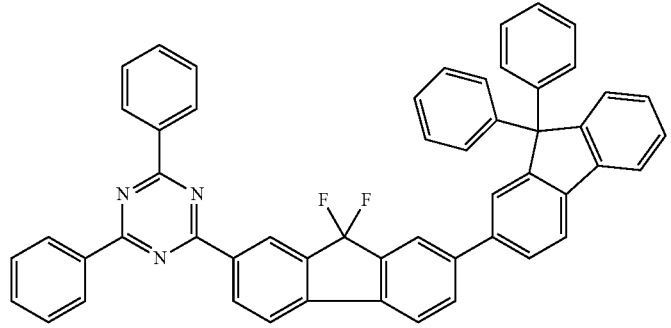
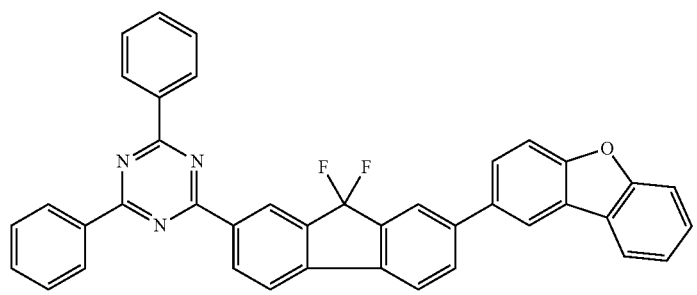
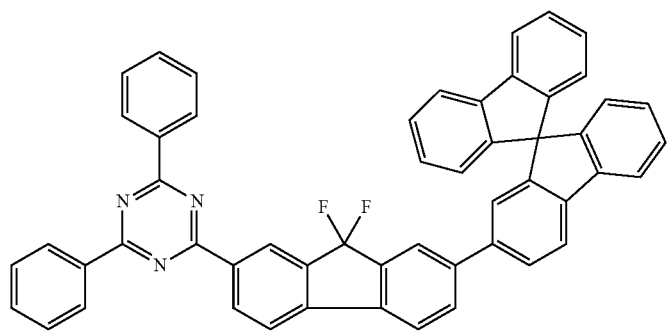
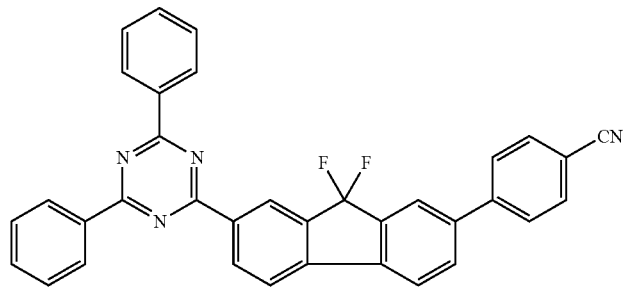
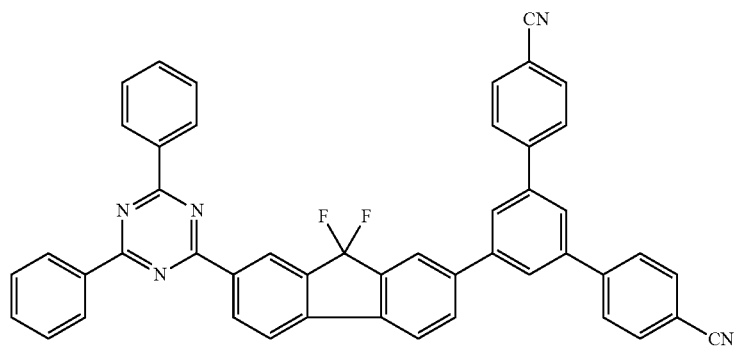

-continued
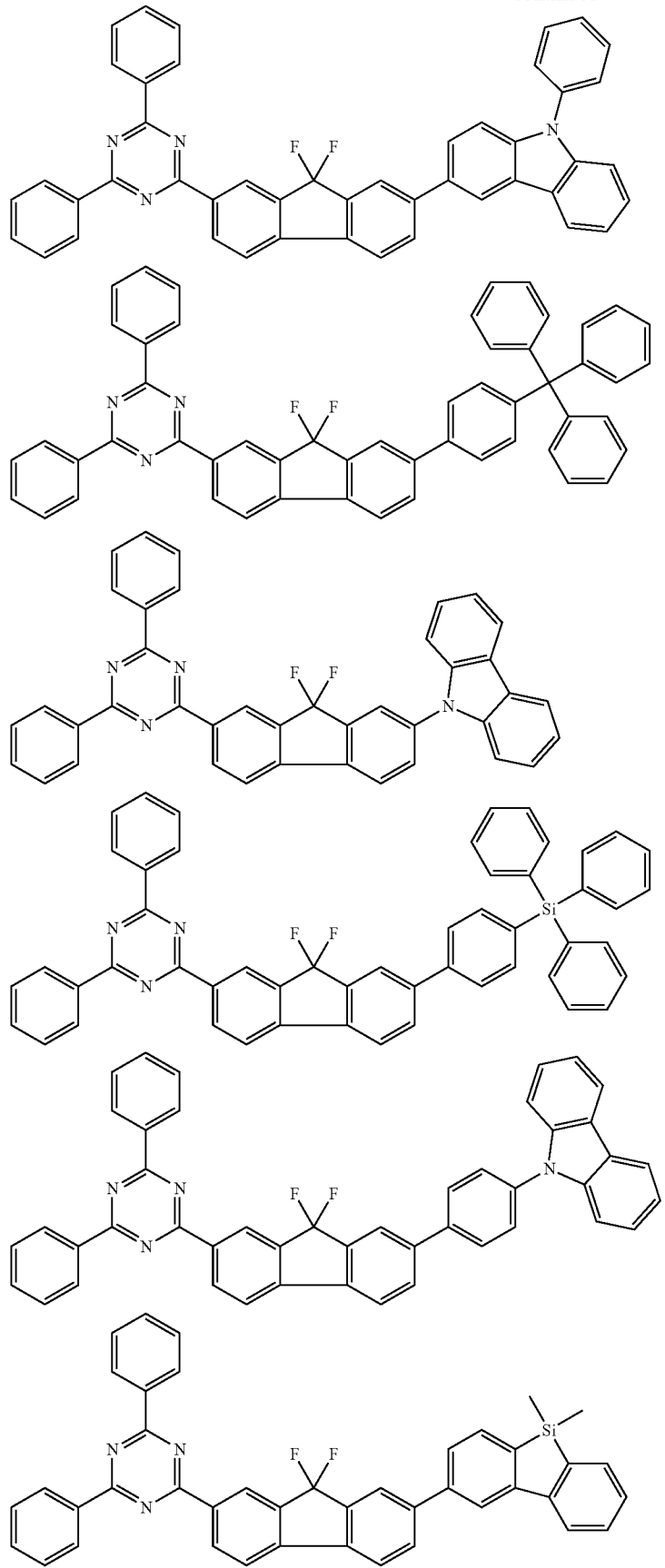

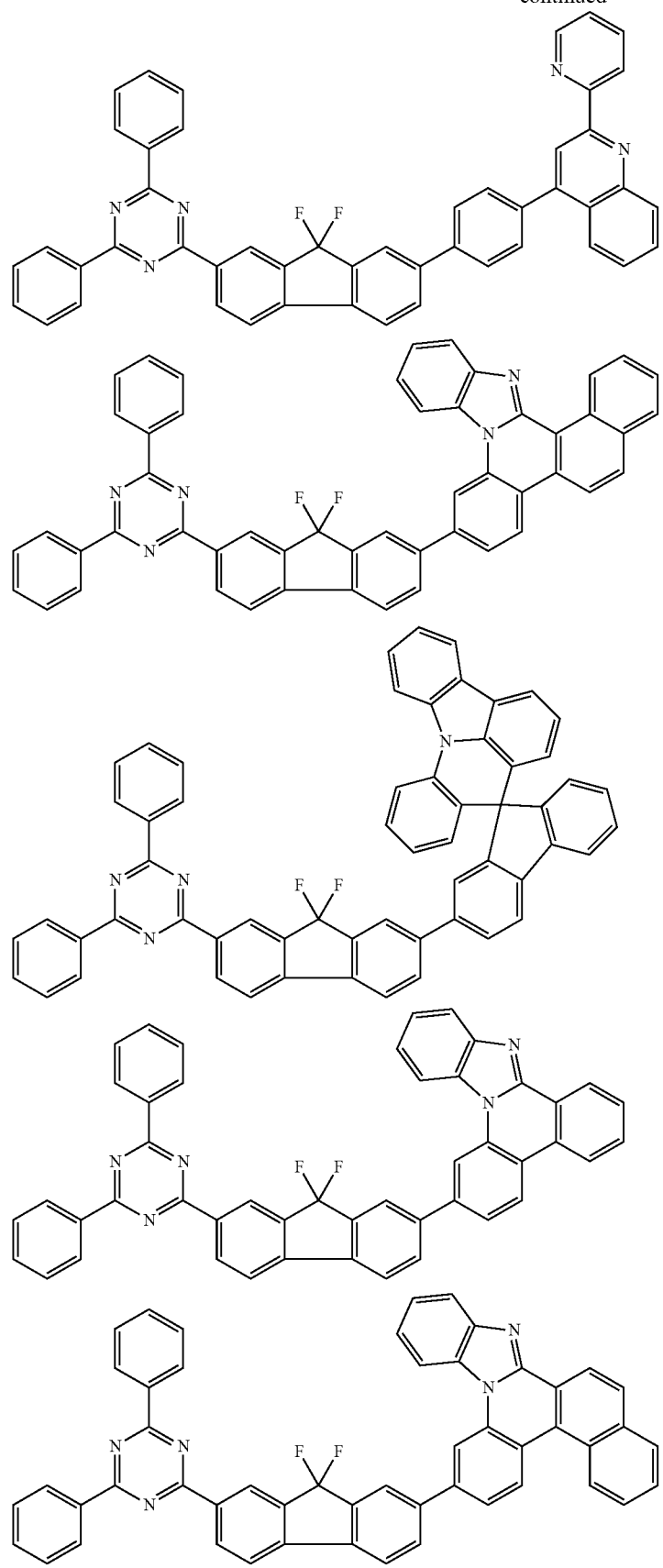

A conjugation length of a compound and an energy band gap thereof are closely related. Specifically, as a conjugation length of a compound increases, an energy band gap thereof decreases. As described above, the cores of the compounds include limited conjugation, and therefore, the energy bad gaps are large.

In the present disclosure, compounds having various energy band gaps may be synthesized by introducing various substituents to a core structure having a large energy band gap as above. Normally, an energy band gap is readily controlled by introducing substituents to a core structure having a large energy band gap, however, when a core structure has a small energy band gap, controlling the energy band gap to become large is difficult. In addition, in the present disclosure, HOMO and LUMO energy levels may be controlled as well by introducing various substituents to a core structure having structures as above.

Furthermore, by introducing various substituents to a core structure having structures as above, compounds having unique properties of the introduced substituents may be synthesized. For example, by introducing substituents normally used as hole injection layer materials, hole transfer layer materials, light emitting layer materials and electron transfer layer materials used for manufacturing an organic light emitting device to the core structure, materials satisfying needs required for each organic material layer may be synthesized.

The compounds according to the present specification may be prepared according to the following general reaction formulae.

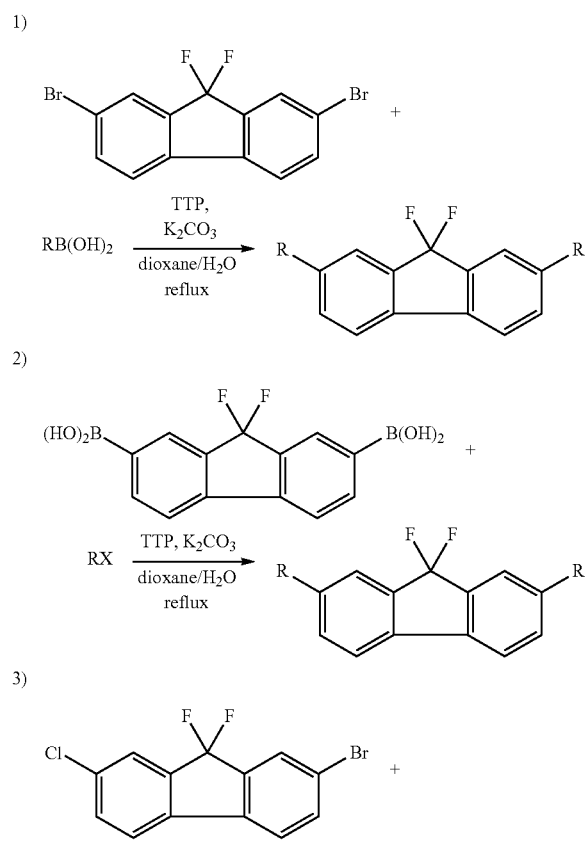

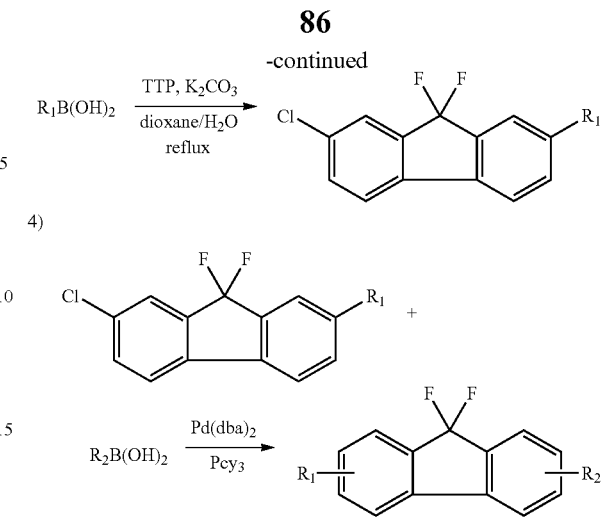

In the reaction formulae, R, $R_1$ and $R_2$ have the same definitions as $Y_1$ or -L-$Y_2$ in Chemical Formula 1.

In addition, an organic light emitting device according to the present disclosure comprises a first electrode, a second electrode, and one or more organic material layers disposed between the first electrode and the second electrode, wherein one or more layers of the organic material layers comprise the above-mentioned compound.

The organic light emitting device of the present disclosure may be manufactured using common methods and materials for manufacturing organic light emitting devices, except that one or more layers of the organic material layers are formed using the compounds described above.

The compound may be formed into the organic material layer using a solution coating method as well as a vacuum deposition method when manufacturing an organic light emitting device. Herein, the solution coating method means spin coating, dip coating, ink jet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

Accordingly, in the organic light emitting device of the present disclosure, the organic material layer may comprise one or more layers of a hole injection layer, a hole transfer layer, and a layer carrying out hole injection and hole transfer at the same time, and one or more layers of the layers may comprise the compound represented by Chemical Formula 1.

In another embodiment, the organic material layer comprises a light emitting layer, and the light emitting layer comprises the compound represented by Chemical Formula 1. As one example, the compound represented by Chemical Formula 1 may be included as a host of the light emitting layer. As another example, the compound represented by Chemical Formula 1 may be included as a phosphorescent host material of the light emitting layer.

As another example, the organic material layer including the compound represented by Chemical Formula 1 comprises the compound represented by Chemical Formula 1 as a host, and includes other organic compounds, metals or metal compounds as a dopant.

As another example, the organic material layer including the compound represented by Chemical Formula 1 comprises the compound represented by Chemical Formula 1 as a host, and the compound may be used together with an iridium (Ir)-based dopant.

In addition, the organic material layer may comprise one or more layers of an electron injection layer and an electron transfer layer, and one or more layers of the layers may comprise the compound.

In another embodiment, the organic material layer of the organic light emitting device comprises a hole transfer layer, and the hole transfer layer includes the compound represented by Chemical Formula 1.

In such an organic material layer having a multilayer structure, the compound may be included in a light emitting layer, a layer carrying out hole injection/hole transfer and light emission at the same time, a layer carrying out hole transfer and light emission at the same time, or a layer carrying out electron transfer and light emission at the same time, and the like.

In one embodiment, the organic material layer includes a light emitting layer, and the light emitting layer may include a compound represented by the following Chemical Formula 17.

[Chemical Formula 17]

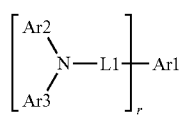

In Chemical Formula 17, r is an integer of 1 or greater,

Ar1 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group, L1 is a direct bond; a substituted or unsubstituted arylene group; or a substituted or unsubstituted heteroarylene group, Ar2 and Ar3 are the same as or different from each other, and each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or may bond to each other to form a substituted or unsubstituted ring, and when r is 2 or greater, the structures in the parentheses are the same as or different from each other.

According to one embodiment, L1 is a direct bond.

According to one embodiment, r is 2.

In one embodiment, Ar1 is a divalent pyrene group unsubstituted or substituted with hydrogen, deuterium, a methyl group, an ethyl group, an isopropyl group or a tert-butyl group; or a chrysene group unsubstituted or substituted with hydrogen, deuterium, a methyl group, an ethyl group, an isopropyl group or a tert-butyl group.

According to one embodiment, Ar1 is a divalent pyrene group.

According to one embodiment, Ar2 and Ar3 are the same as or different from each other, and each independently a substituted or unsubstituted aryl group having 6 to 30 carbon atoms.

According to one embodiment, Ar2 and Ar3 are the same as or different from each other, and each independently an aryl group unsubstituted or substituted with an alkyl group.

In one embodiment, Ar2 and Ar3 are the same as or different from each other, and each independently an aryl group unsubstituted or substituted with a methyl group, an ethyl group or an isopropyl group.

According to one embodiment, Ar2 and Ar3 are the same as or different from each other, and each independently a phenyl group unsubstituted or substituted with a methyl group.

According to one embodiment, Ar2 and Ar3 are a phenyl group.

For example, the structure of the organic light emitting device of the present disclosure may have structures as shown in FIG. 1 and FIG. 2, however, the structure is not limited thereto.

FIG. 1 illustrates a structure of an organic light emitting device in which an anode (2), a light emitting layer (3) and a cathode (4) are consecutively laminated on a substrate (1). In such a structure, the compound may be included in the light emitting layer (3).

FIG. 2 illustrates a structure of an organic light emitting device in which an anode (2), a hole injection layer (5), a hole transfer layer (6), a light emitting layer (3), an electron transfer layer (7) and a cathode (4) are consecutively laminated on a substrate (1). In such a structure, the compound may be included in the hole injection layer (5), the hole transfer layer (6), the light emitting layer (3) or the electron transfer layer (7).

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer, and an anode material on a substrate.

The organic material layer may have a multilayer structure including a hole injection layer, a hole transfer layer, a light emitting layer, an electron transfer layer and the like, but is not limited thereto, and may have a single layer structure. In addition, the organic material layer may be prepared into less numbers of layers using various polymer materials through a solvent process such as spin coating, dip coating, doctor blading, screen printing, ink jet printing or a thermal transfer method instead of a deposition method.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3- methyl compound), poly[3,4-(ethylene-1,2-dioxy)compound] (PEDT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, materials having a highest occupied molecular orbital (HOMO) between the work function of an anode material and the HOMO of surrounding organic material layers are preferable as materials favorably receiving holes from an anode at a low voltage. Specific examples of the hole injection material include metal porphyrins, oligothiophene, arylamine-based organic materials, hexanitrile hexazatriphenylene-based organic materials, quinacridone-based organic materials, perylene-based organic materials, anthraquinone, and polyaniline- and polythiophene-based conductive polymers, and the like, but are not limited thereto.

As the hole transfer material, materials having high mobility for holes are suitable as materials receiving holes from an anode or a hole injection layer and transfers the holes to a light emitting layer. Specific examples thereof include arylamine-based organic materials, conductive polymers, block copolymers having conjugated parts and non-conjugated parts together, and the like, but are not limited thereto.

As the light emitting material, materials having favorable quantum efficiency for fluorescence or phosphorescence are preferable as materials capable of emitting light in a visible light region by receiving holes and electrons from a hole transfer layer and an electron transfer layer, respectively, and binding the holes and the electrons. Specific examples thereof include 8-hydroxy-quinoline aluminum complexes (Alq$_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The organic material layer including the compound represented by Chemical Formula 1 includes the compound represented by Chemical Formula 1 as a host, and the compound may be used together with an iridium (Ir)-based dopant.

The iridium-based complexes used as the dopant are as follows.

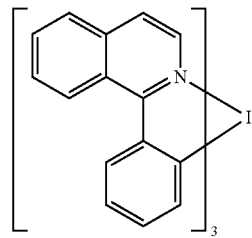

[Ir(piq)$_3$]

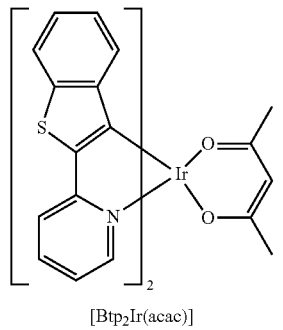

[Btp$_2$Ir(acac)]

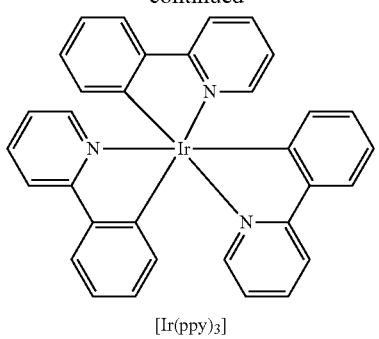

[Ir(ppy)$_3$]

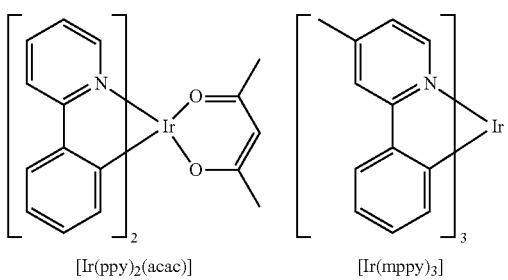

[Ir(ppy)$_2$(acac)]                [Ir(mppy)$_3$]

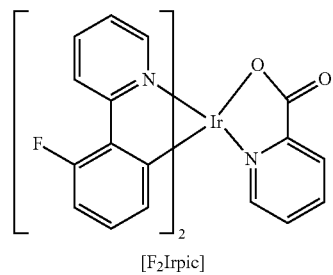

[F$_2$Irpic]

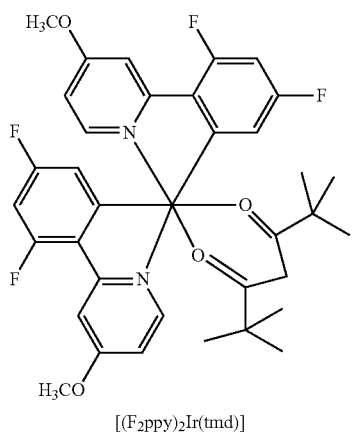

[(F$_2$ppy)$_2$Ir(tmd)]

-continued

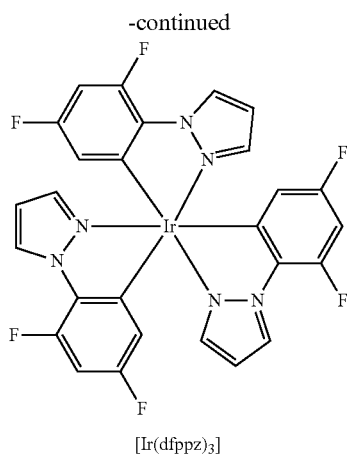

[Ir(dfppz)₃]

As the electron transfer material, materials having high mobility for electrons are suitable as materials favorably receiving electrons from a cathode and transferring the electrons to a light emitting layer. Specific examples thereof include Al complexes of 8-hydroxyquinoline; complexes including $Alq_3$; organic radical compounds; hydroxyflavon-metal complexes and the like, but are not limited thereto.

The organic light emitting device according to the present specification may be a top-emission type, a bottom-emission type or a dual-emission type depending on the materials used.

The following examples are for illustrative purposes only, and the scope of the present disclosure is not limited thereto.

Preparation Example

The following Compounds 1 to 23 were prepared through Preparation Examples 1 to 23.

1

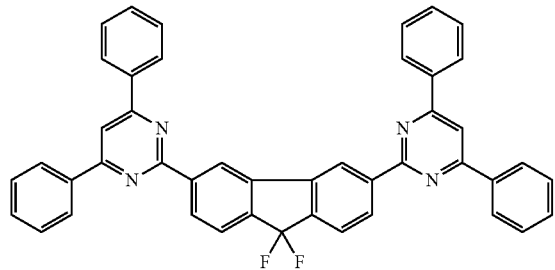

2

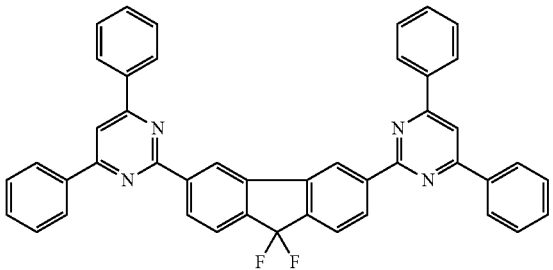

3

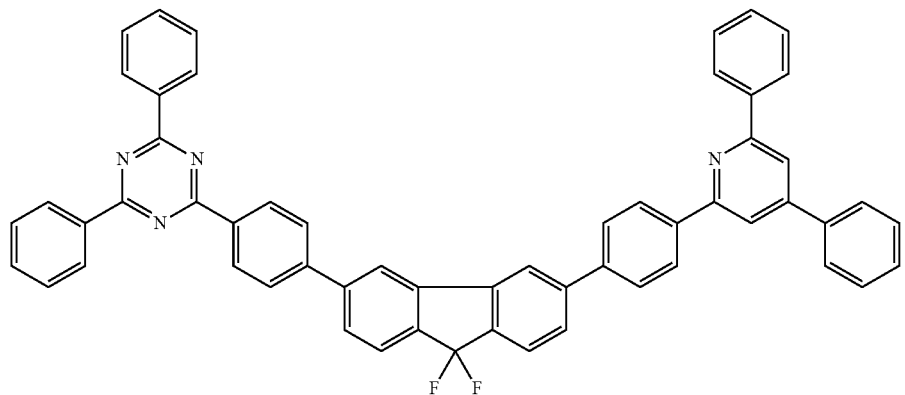

4

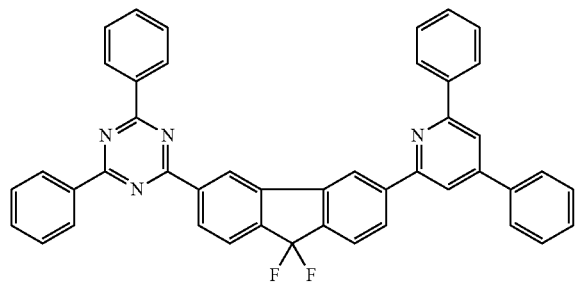

5

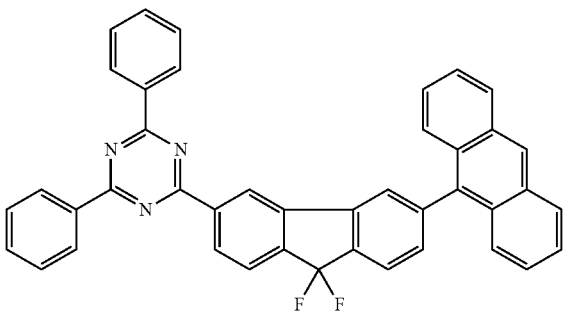

-continued
6
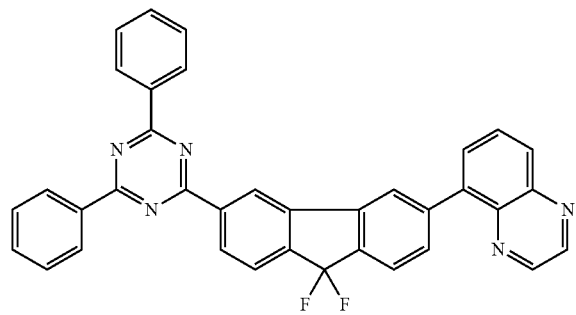
7
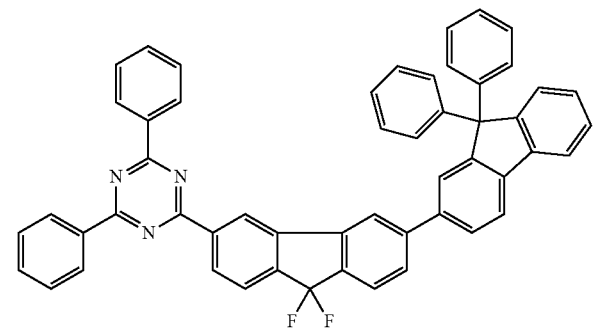
8
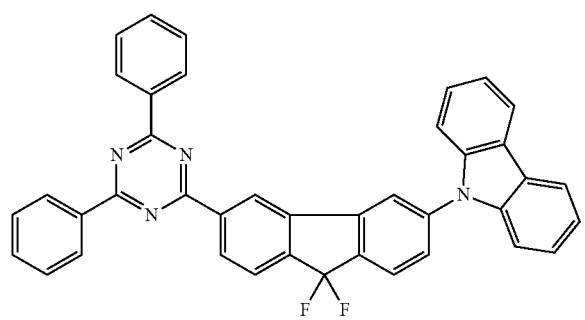
9
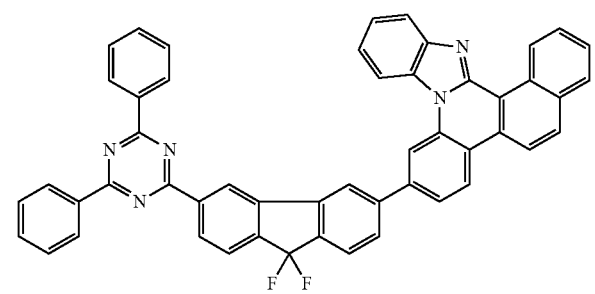
10
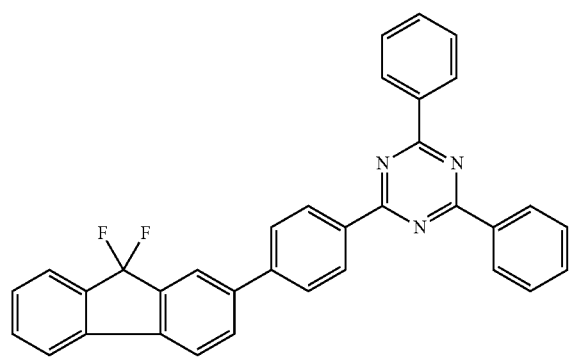
11
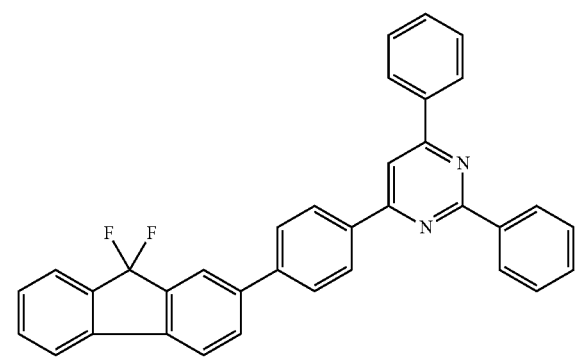
12
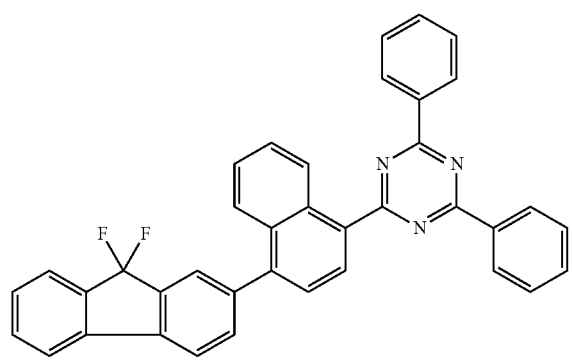
13
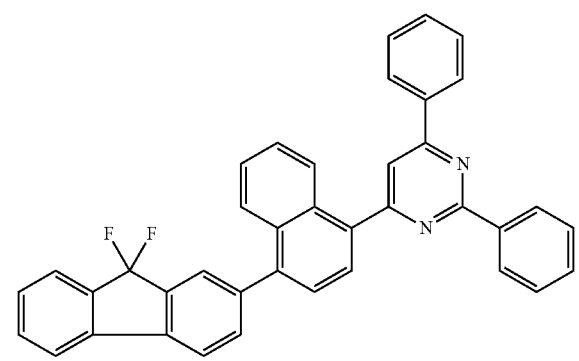

-continued
14
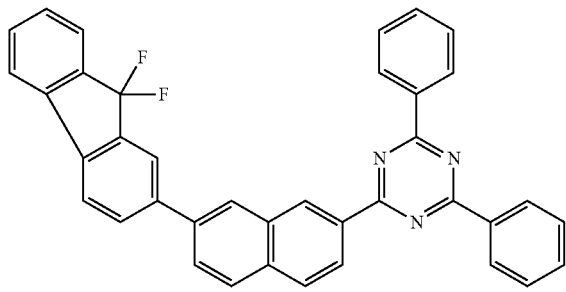
15
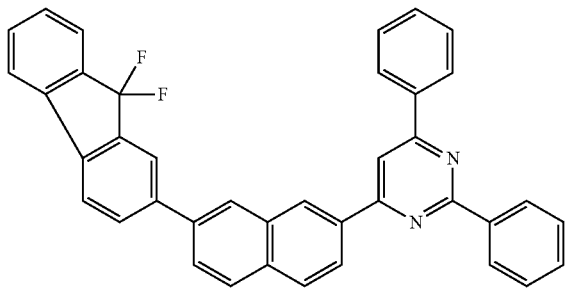
16
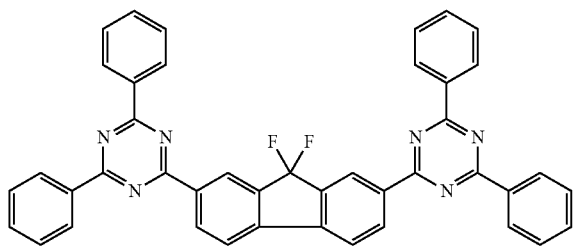
17
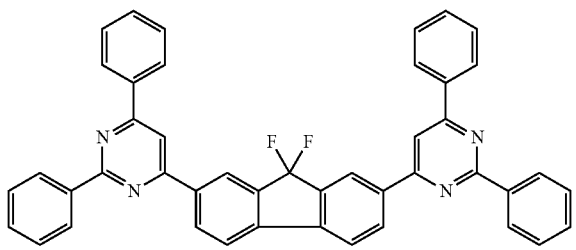
18
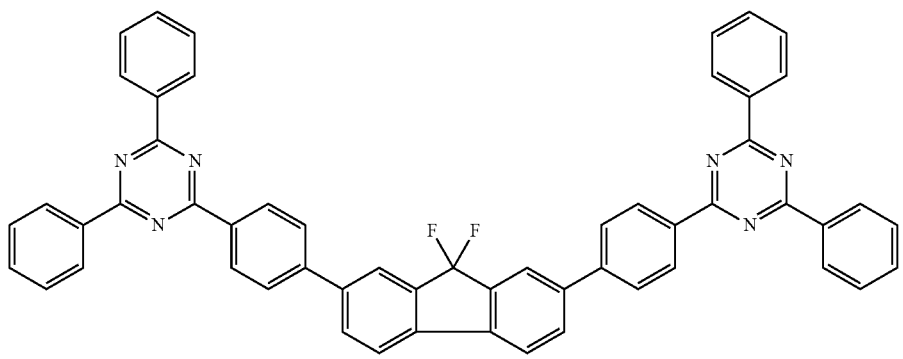
19
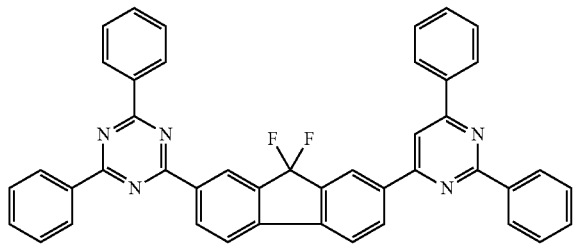
20
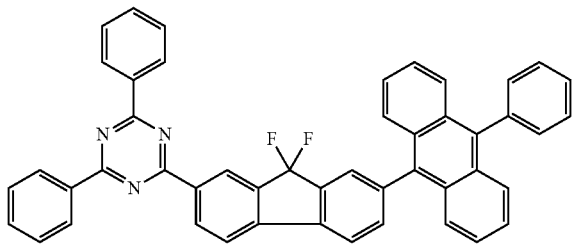
21
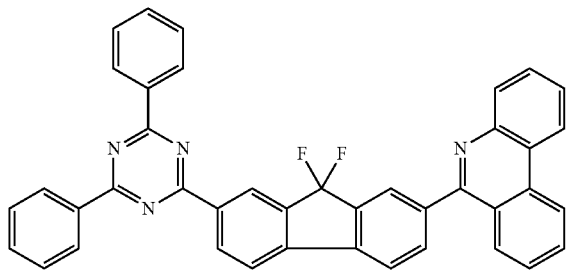
22
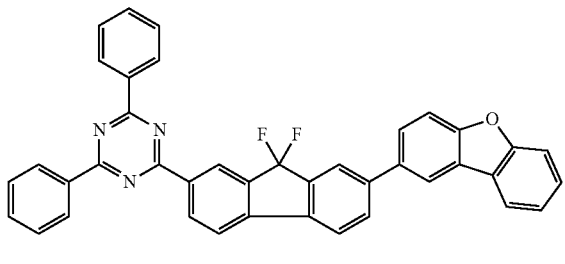

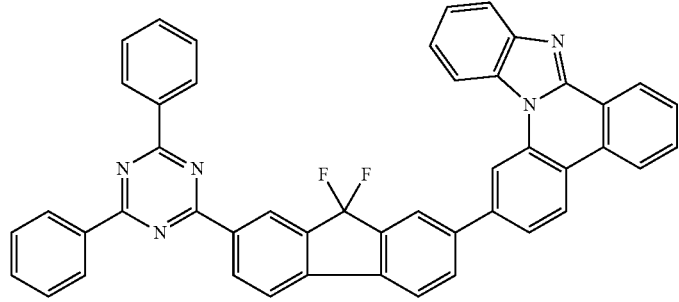

Preparation Example

Preparation Example 1: Preparation of the Following Compound 1

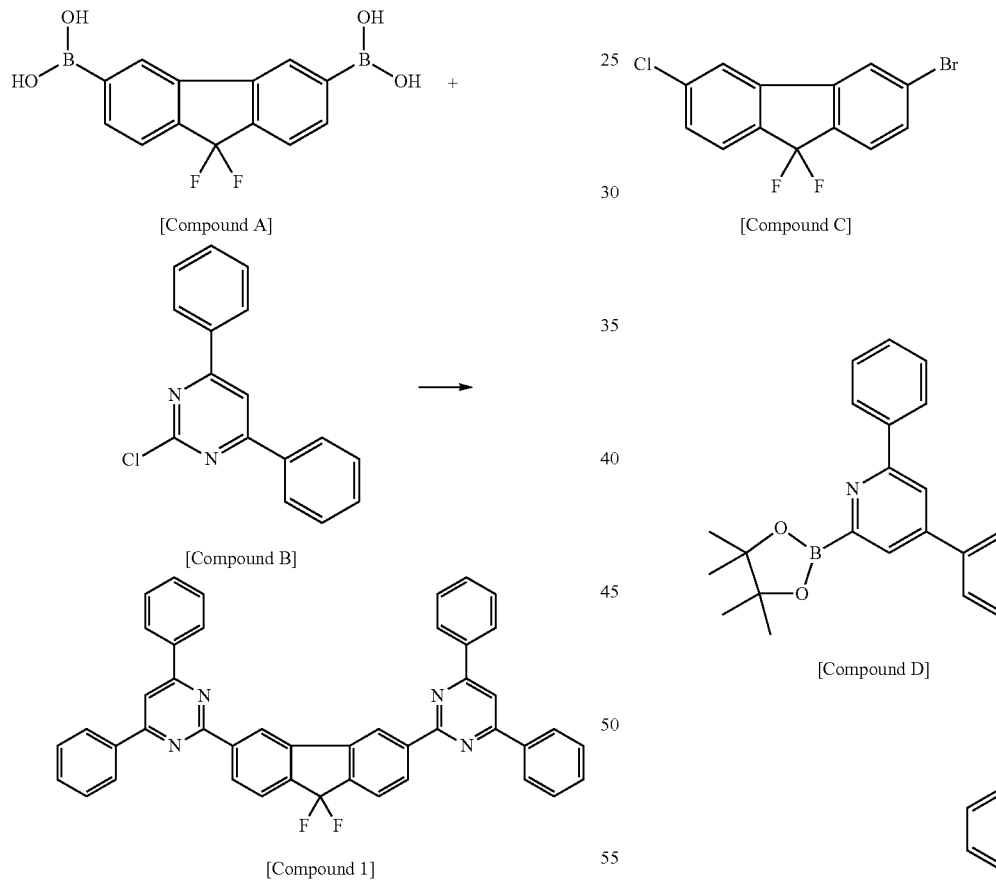

Under nitrogen atmosphere, Compound A (10 g, 34.6 mmol) and Compound B (9.2 g, 34.6 mmol) were dissolved in dioxane (100 mL), potassium carbonate (9.5 g, 69.2 mmol) dissolved in water (50 mL) was added thereto, and the result was heated while stirring. Under reflux, bis(dibenzylideneacetone)palladium (398 mg, 0.69 mmol) and tricyclohexylphosphine (386 mg, 1.4 mmol) were added thereto, and the result was stirred under reflux for 12 hours. After the reaction was complete, the temperature was lowered to room temperature, and the result was filtered. The obtained solids were washed with water and ethanol to prepare Compound 1 (19.9 g, yield: 87%).

Preparation Example 2: Synthesis of the Following Compound 2

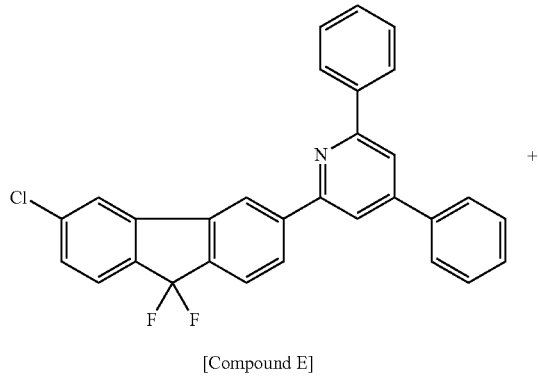

-continued

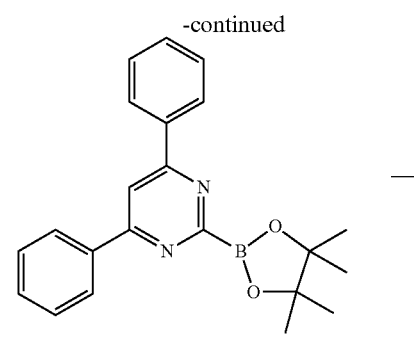

[Compound F]

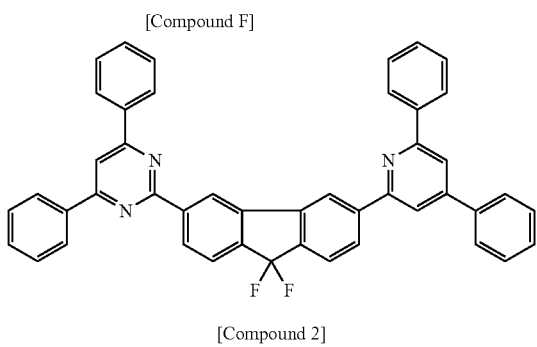

[Compound 2]

Under nitrogen atmosphere, Compound C (12 g, 38.1 mmol) and Compound D (13.6 g, 38.1 mmol) were dissolved in tetrahydrofuran (120 mL), potassium carbonate (9.5 g, 69.2 mmol) dissolved in water (50 mL) was added thereto, and the result was heated while stirring. Under reflux, palladium tetratriphenylphosphine (440 mg, 0.38 mmol) was added thereto, and the result was stirred under reflux for 5 hours. After the reaction was compete, the temperature was lowered to room temperature, and ethanol was added thereto to obtain solids. Solids obtained after filtering were washed with water and ethanol to prepare Compound E in an 85% yield.

Under nitrogen atmosphere, Compound E (15 g, 32.3 mmol) and Compound F (11.2 g, 32.3 mmol) were dissolved in dioxane (120 mL), potassium carbonate (8.9 g, 64.6 mmol) dissolved in water (60 mL) was added thereto, and the result was heated while stirring. Under reflux, bis(dibenzylideneacetone)palladium (371 mg, 0.65 mmol) and tricyclohexylphosphine (364 mg, 1.3 mmol) were added thereto, and the result was stirred under reflux for 12 hours. After the reaction was complete, the temperature was lowered to room temperature, and the result was filtered. The obtained solids were washed with water and ethanol to prepare Compound 2 (17.0 g, yield: 85%).

Preparation Example 3: Synthesis of the Following Compound 3

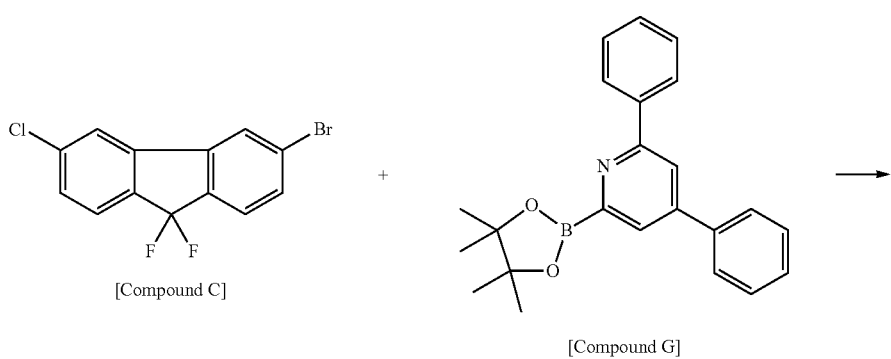

[Compound C]  [Compound G]

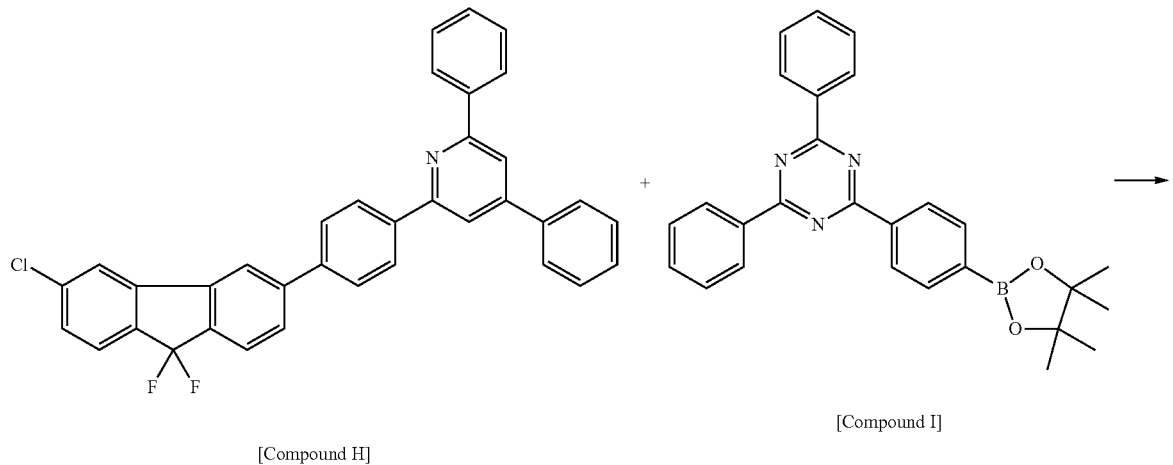

[Compound H]  [Compound I]

-continued

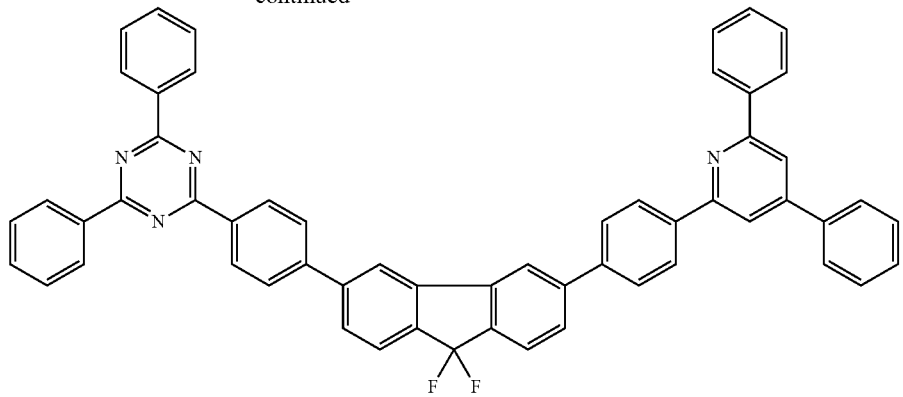

[Compound 3]

Compound H was prepared in the same manner as Compound E except that Compound G was used instead of Compound D. Next, Compound 3 was prepared in the same manner as Compound 2 except that Compound H was used instead of Compound E, and Compound I was used instead of Compound F.

Preparation Example 4: Synthesis of the Following Compound 4

-continued

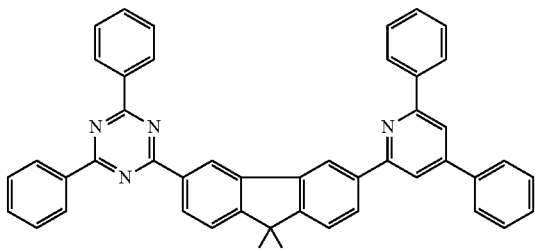

[Compound 4]

Compound 4 was prepared in the same manner as Compound 2 except that Compound J was used instead of Compound F.

Preparation Example 5: Synthesis of the Following Compound 5

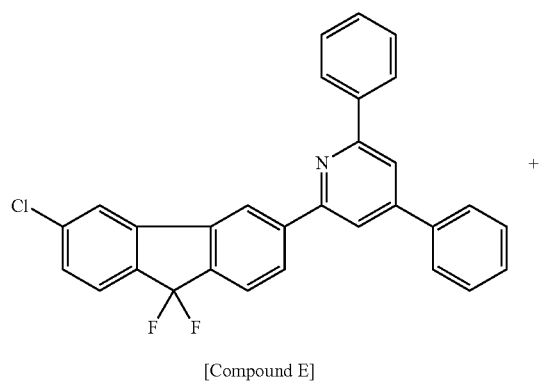

[Compound E]

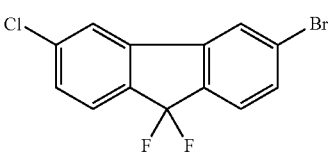

[Compound C]

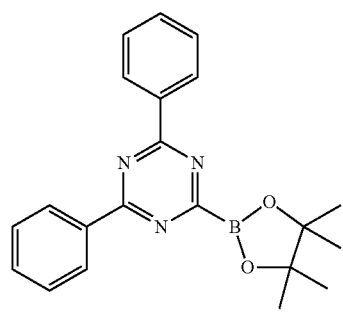

[Compound J]

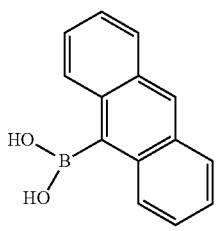

[Compound K]

-continued

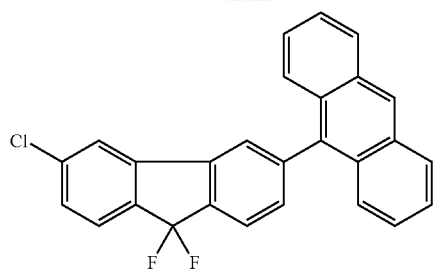

[Compound L]

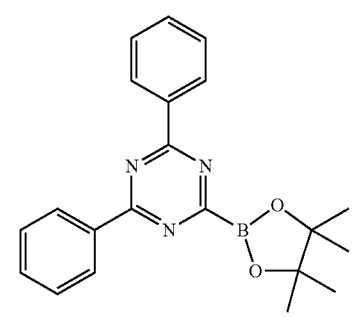

[Compound J]

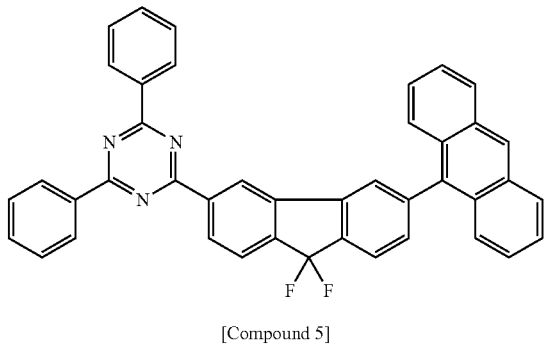

[Compound 5]

Compound L was prepared in the same manner as Compound E except that Compound K was used instead of Compound D. Next, Compound 5 was prepared in the same manner as Compound 2 except that Compound L was used instead of Compound E, and Compound J was used instead of Compound F.

Preparation Example 6: Synthesis of the Following Compound 6

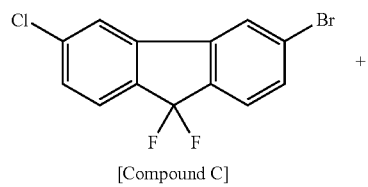

[Compound C]

-continued

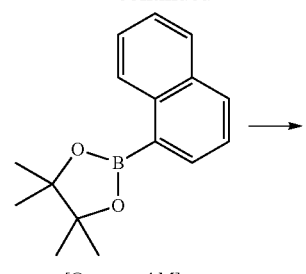

[Compound M]

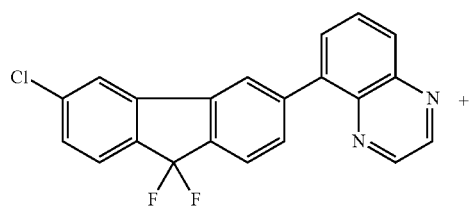

[Compound N]

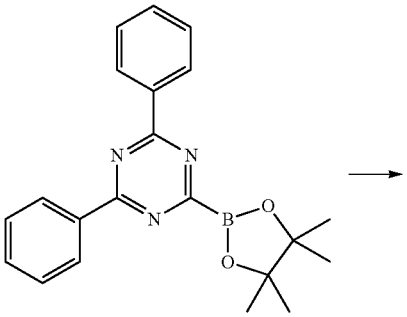

[Compound J]

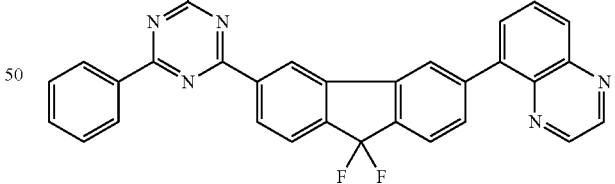

[Compound 6]

Compound N was prepared in the same manner as Compound E except that Compound M was used instead of Compound D. Next, Compound 6 was prepared in the same manner as Compound 2 except that Compound N was used instead of Compound E, and Compound J was used instead of Compound F.

Preparation Example 7: Synthesis of the Following Compound 7

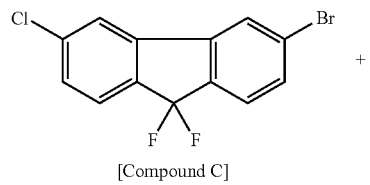

[Compound C]

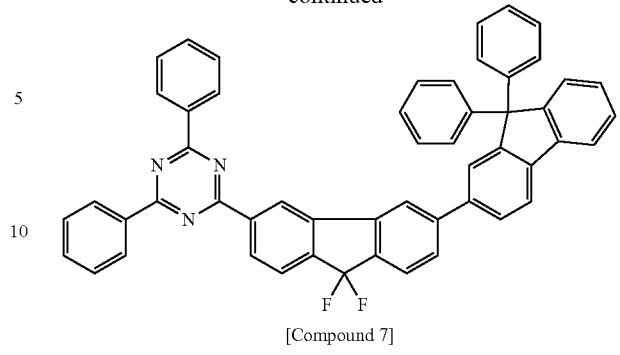

[Compound 7]

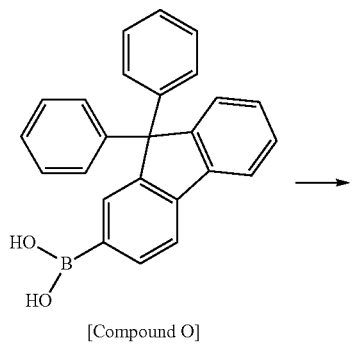

[Compound O]

Compound P was prepared in the same manner as Compound E except that Compound O was used instead of Compound D. Next, Compound 7 was prepared in the same manner as Compound 2 except that Compound P was used instead of Compound E, and Compound J was used instead of Compound F.

Preparation Example 8: Synthesis of the Following Compound 8

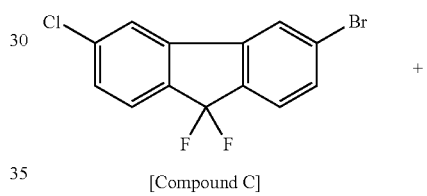

[Compound C]

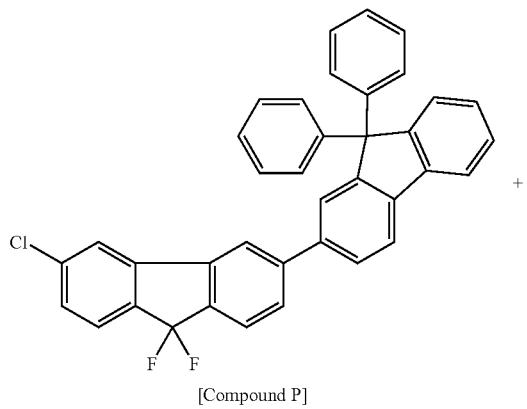

[Compound P]

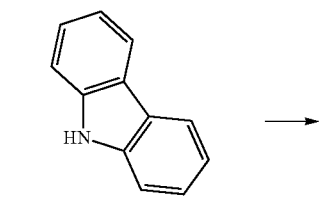

[Compound Q]

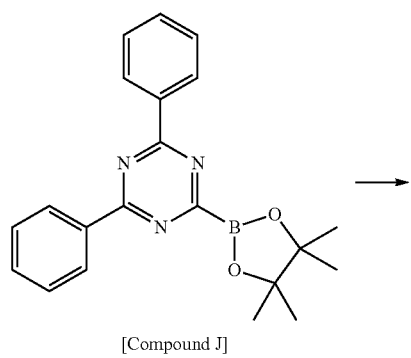

[Compound J]

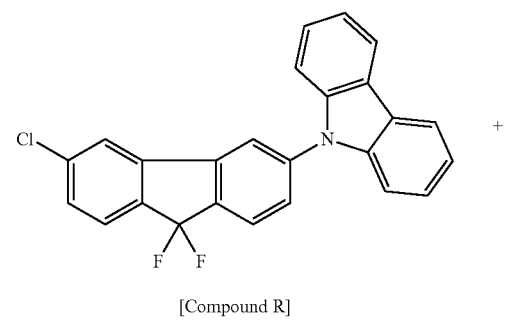

[Compound R]

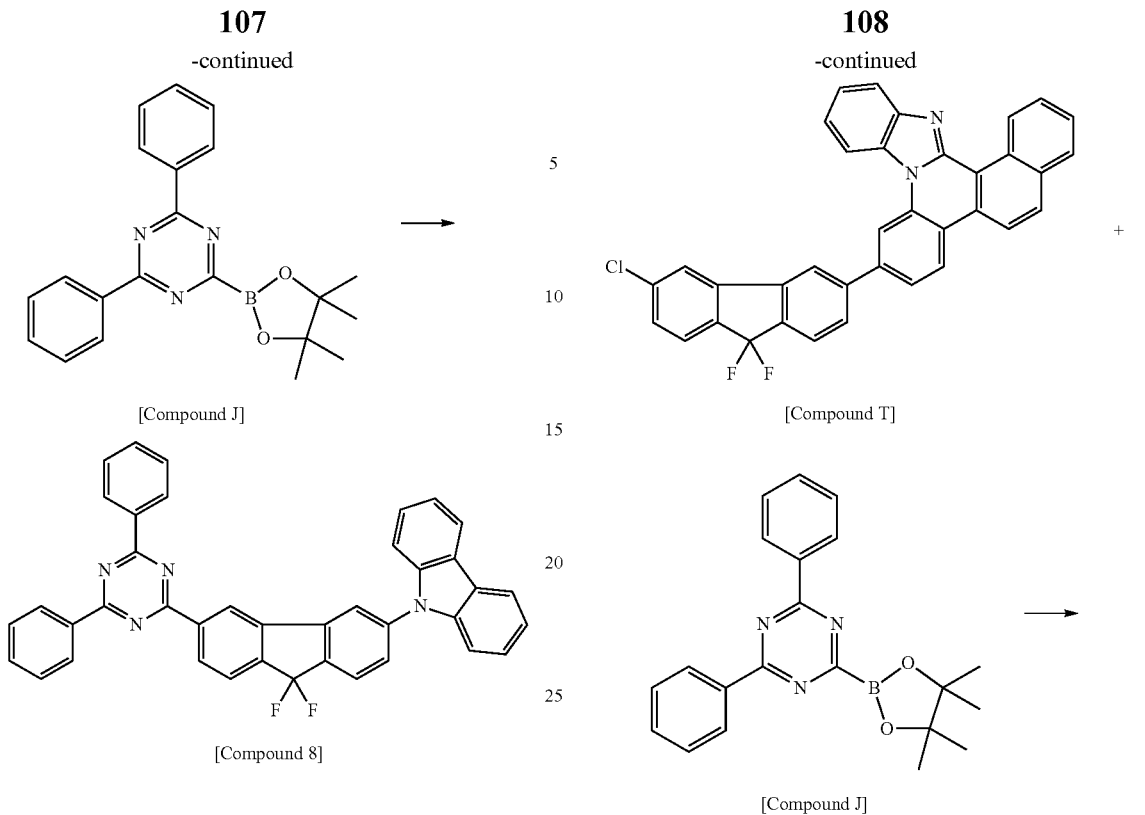

[Compound J]

[Compound 8]

Compound R was prepared in the same manner as Compound E except that Compound Q was used instead of Compound D. Next, Compound 8 was prepared in the same manner as Compound 2 except that Compound R was used instead of Compound E, and Compound J was used instead of Compound F.

Preparation Example 9: Synthesis of the Following Compound 9

[Compound C]

[Compound S]

[Compound T]

[Compound J]

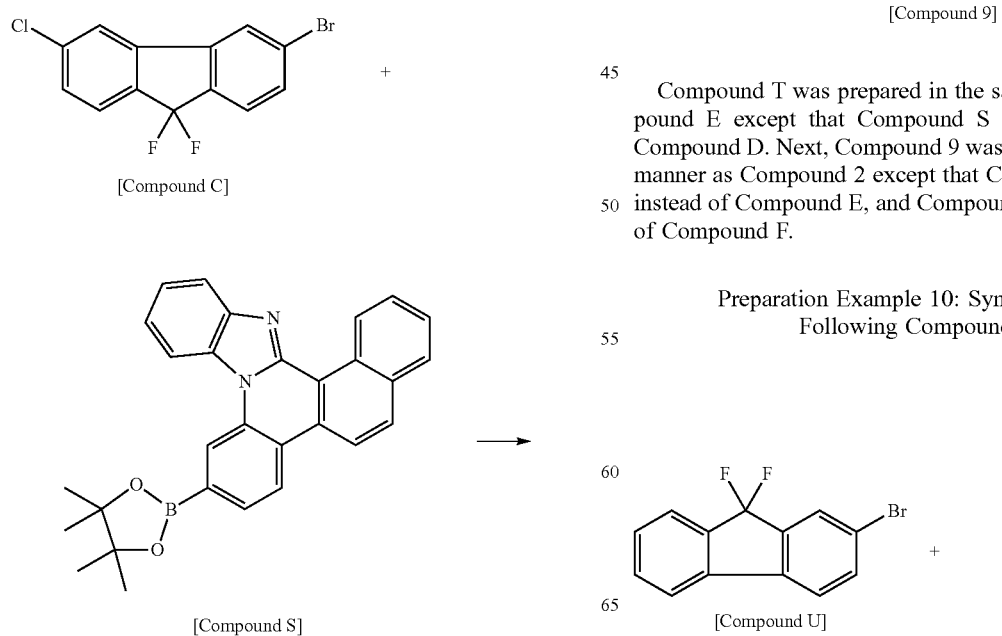

[Compound 9]

Compound T was prepared in the same manner as Compound E except that Compound S was used instead of Compound D. Next, Compound 9 was prepared in the same manner as Compound 2 except that Compound T was used instead of Compound E, and Compound J was used instead of Compound F.

Preparation Example 10: Synthesis of the Following Compound 10

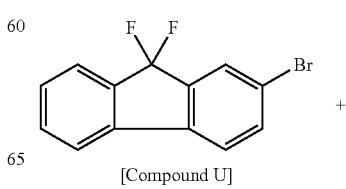

[Compound U]

-continued

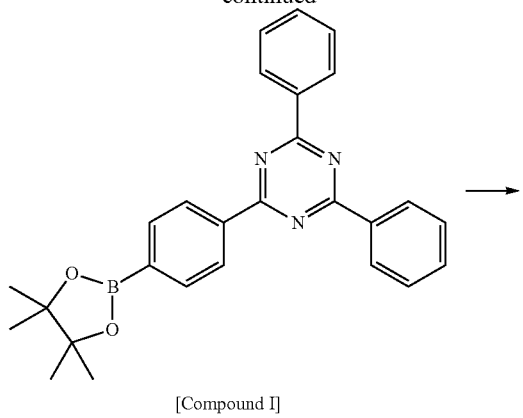

[Compound I]

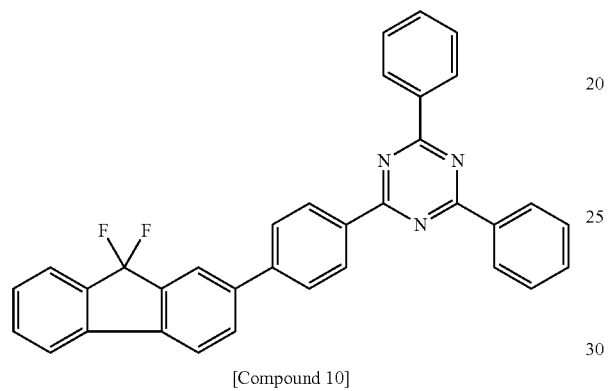

[Compound 10]

Compound 10 was prepared in the same manner as Compound E except that Compound U was used instead of Compound C, and Compound I was used instead of Compound D.

Preparation Example 11: Synthesis of the Following Compound 11

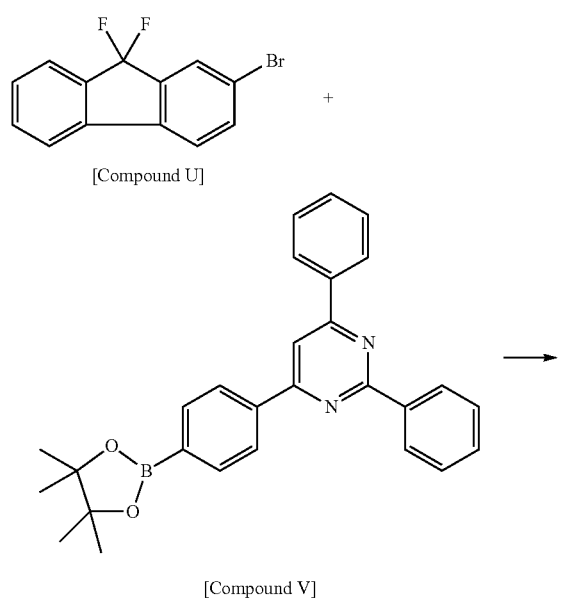

[Compound U]

[Compound V]

-continued

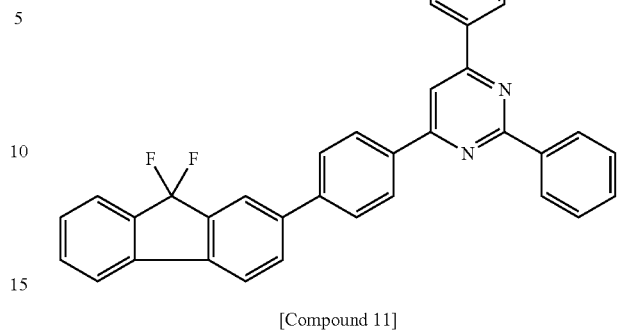

[Compound 11]

Compound 11 was prepared in the same manner as Compound E except that Compound U was used instead of Compound C, and Compound V was used instead of Compound D.

Preparation Example 12: Synthesis of the Following Compound 12

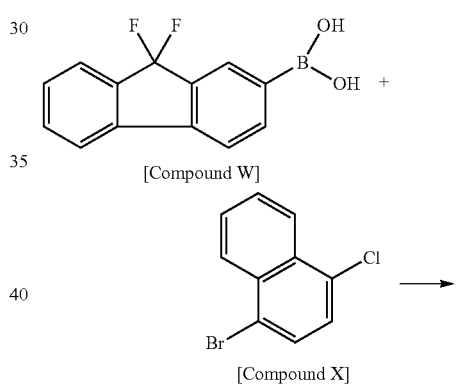

[Compound W]

[Compound X]

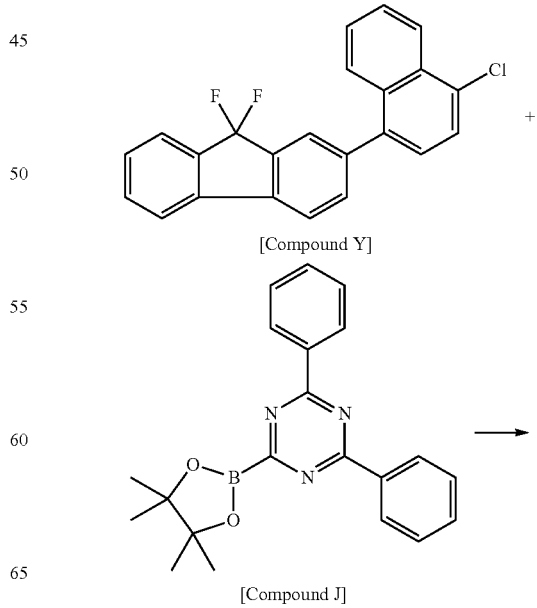

[Compound Y]

[Compound J]

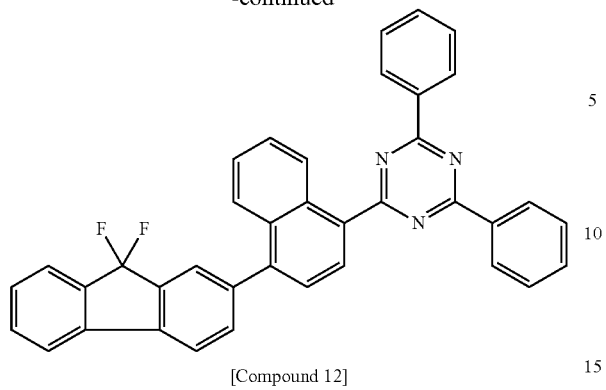

[Compound 12]

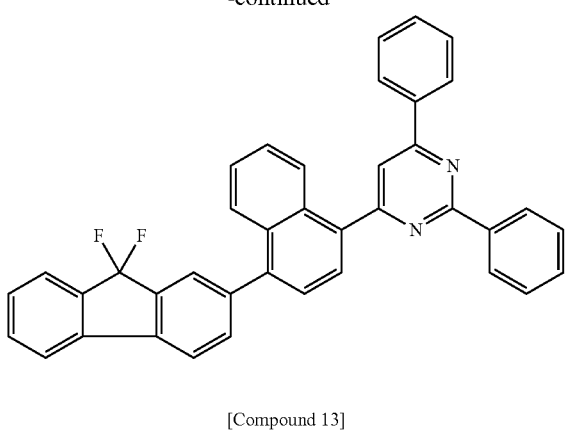

[Compound 13]

Compound Y was prepared in the same manner as Compound E except that Compound X was used instead of Compound C, and Compound W was used instead of Compound D. Next, Compound 12 was prepared in the same manner as Compound 2 except that Compound Y was used instead of Compound E, and Compound J was used instead of Compound F.

Compound 13 was prepared in the same manner as Compound 12 except that Compound Z was used instead of Compound X.

Preparation Example 13: Synthesis of the Following Compound 13

Preparation Example 14: Synthesis of the Following Compound 14

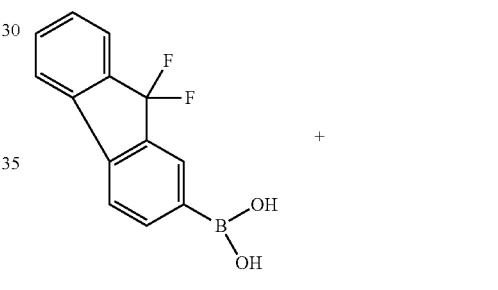

[Compound W]

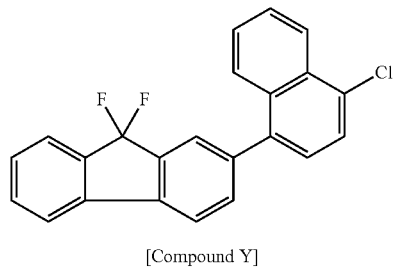

[Compound Y]

Br—[naphthalene]—Cl

[Compound AA]

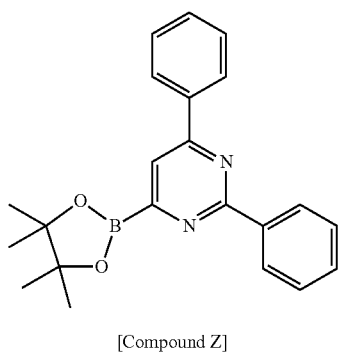

[Compound Z]

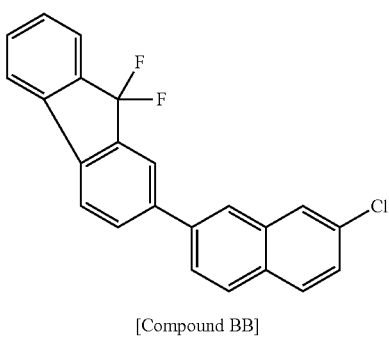

[Compound BB]

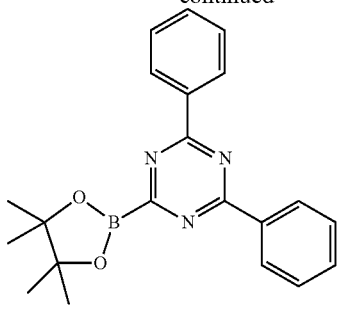

[Compound J]

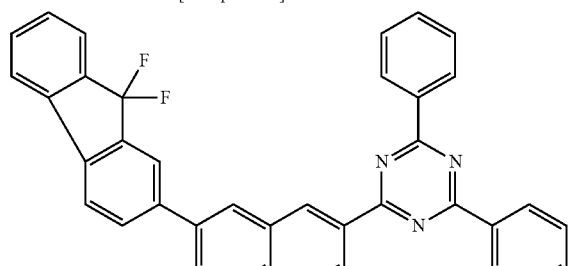

[Compound 14]

Compound BB was prepared in the same manner as Compound E except that Compound AA was used instead of Compound C, and Compound W was used instead of Compound D. Next, Compound 14 was prepared in the same manner as Compound 2 except that Compound BB was used instead of Compound E, and Compound J was used instead of Compound F.

Preparation Example 15: Synthesis of the Following Compound 15

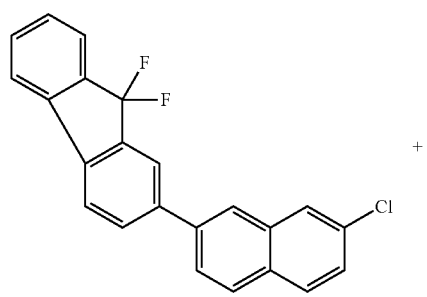

[Compound BB]

+

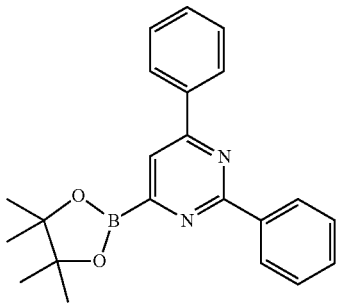

[Compound Z]

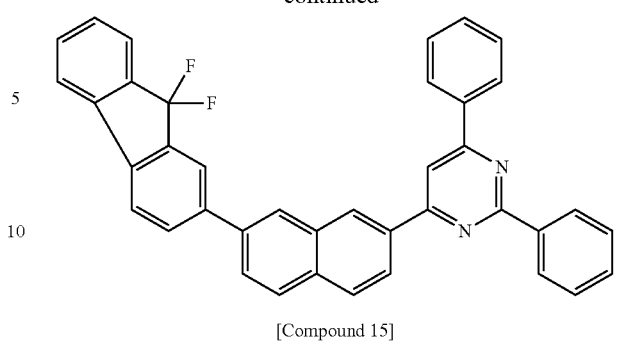

[Compound 15]

Compound 15 was prepared in the same manner as Compound 14 except that Compound Z was used instead of Compound J.

Preparation Example 16: Synthesis of the Following Compound 16

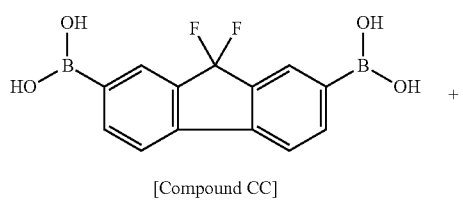

[Compound CC]

+

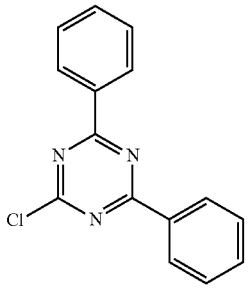

[Compound DD]

→

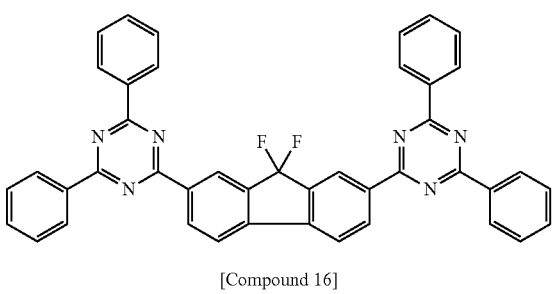

[Compound 16]

Compound 16 was prepared in the same manner as Compound 2 except that Compound DD was used instead of Compound E, and Compound CC was used instead of Compound F.

Preparation Example 17: Synthesis of the Following Compound 17

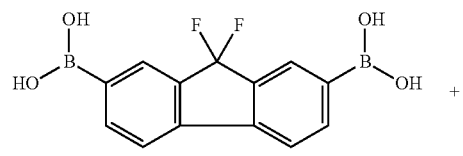

[Compound CC]

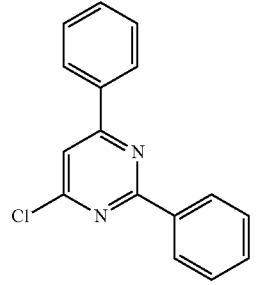

[Compound FF]

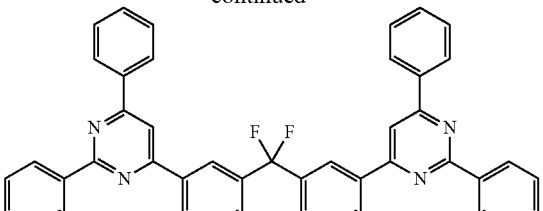

[Compound 17]

Compound 17 was prepared in the same manner as Compound 2 except that Compound FF was used instead of Compound E, and Compound CC was used instead of Compound F.

Preparation Example 18: Synthesis of the Following Compound 18

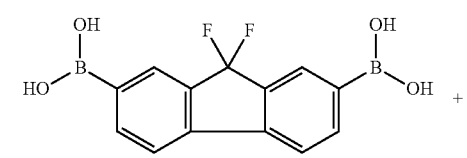

[Compound CC]

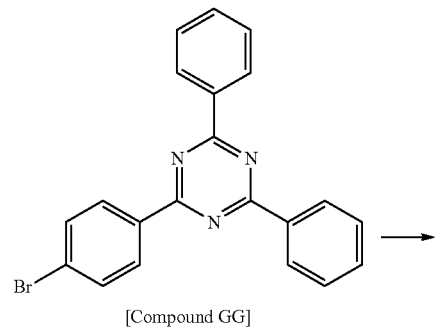

[Compound GG]

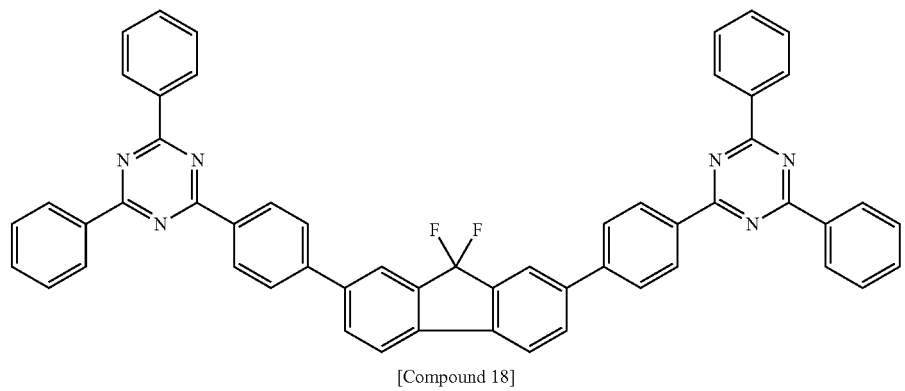

[Compound 18]

Compound 18 was prepared in the same manner as Compound 2 except that Compound GG was used instead of Compound E, and Compound CC was used instead of Compound F.

Preparation Example 19: Synthesis of the Following Compound 19

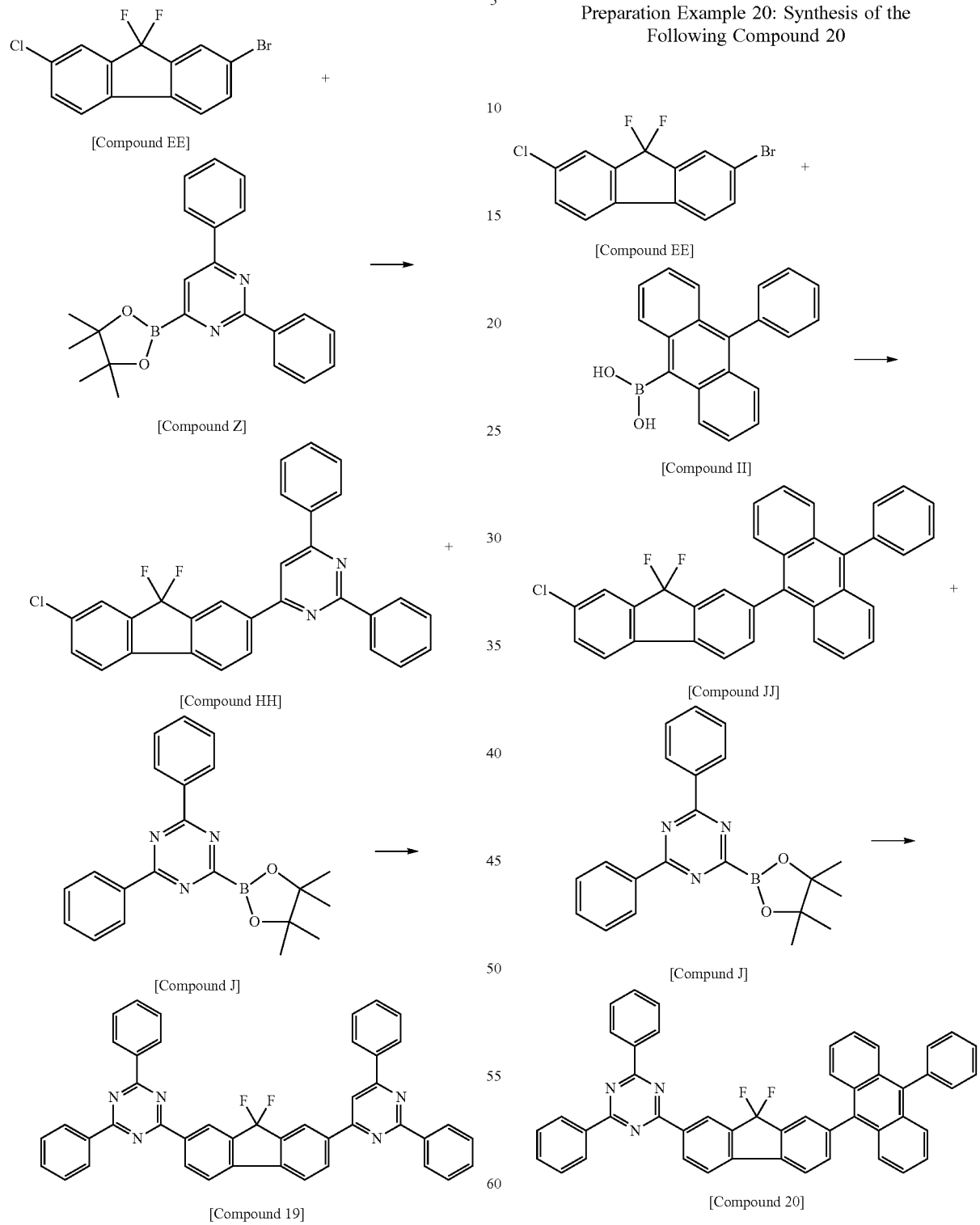

Compound HH was prepared in the same manner as Compound E except that Compound EE was used instead of Compound C, and Compound Z was used instead of Compound E. Next, Compound 19 was prepared in the same manner as Compound 2 except that Compound HH was used instead of Compound E, and Compound J was used instead of Compound F.

Preparation Example 20: Synthesis of the Following Compound 20

Compound JJ was prepared in the same manner as Compound E except that Compound EE was used instead of Compound C, and Compound II was used instead of Compound E. Next, Compound 20 was prepared in the same manner as Compound 2 except that Compound JJ was used instead of Compound E, and Compound J was used instead of Compound F.

Preparation Example 21: Synthesis of the Following Compound 21

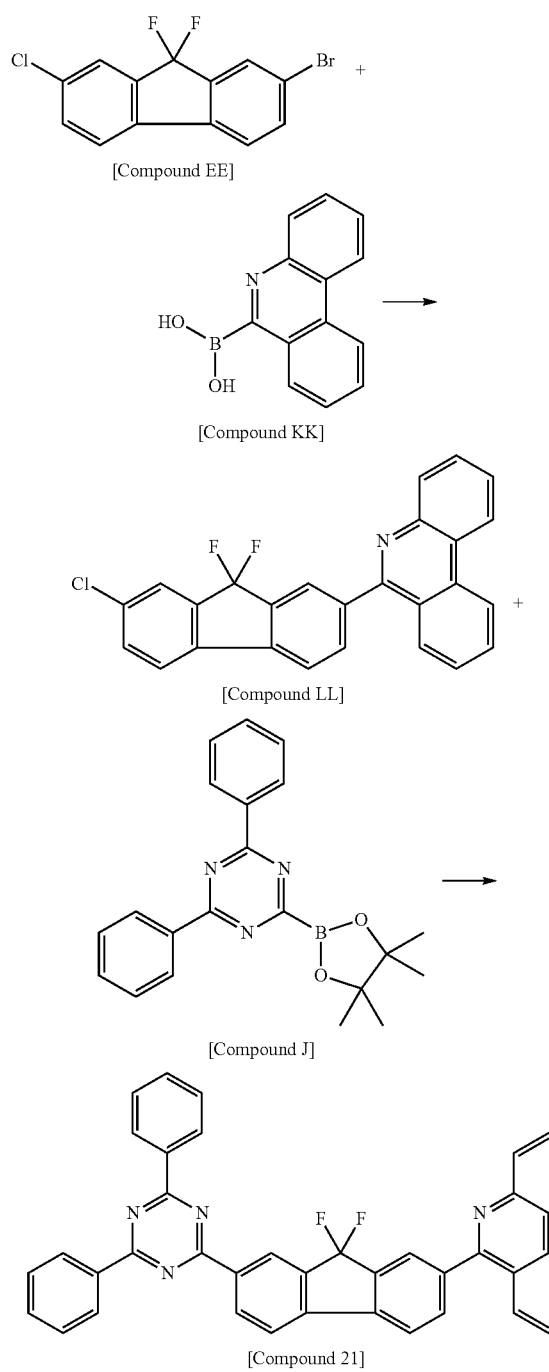

Compound LL was prepared in the same manner as Compound E except that Compound EE was used instead of Compound C, and Compound KK was used instead of Compound E. Next, Compound 21 was prepared in the same manner as Compound 2 except that Compound LL was used instead of Compound E, and Compound J was used instead of Compound F.

Preparation Example 22: Synthesis of the Following Compound 22

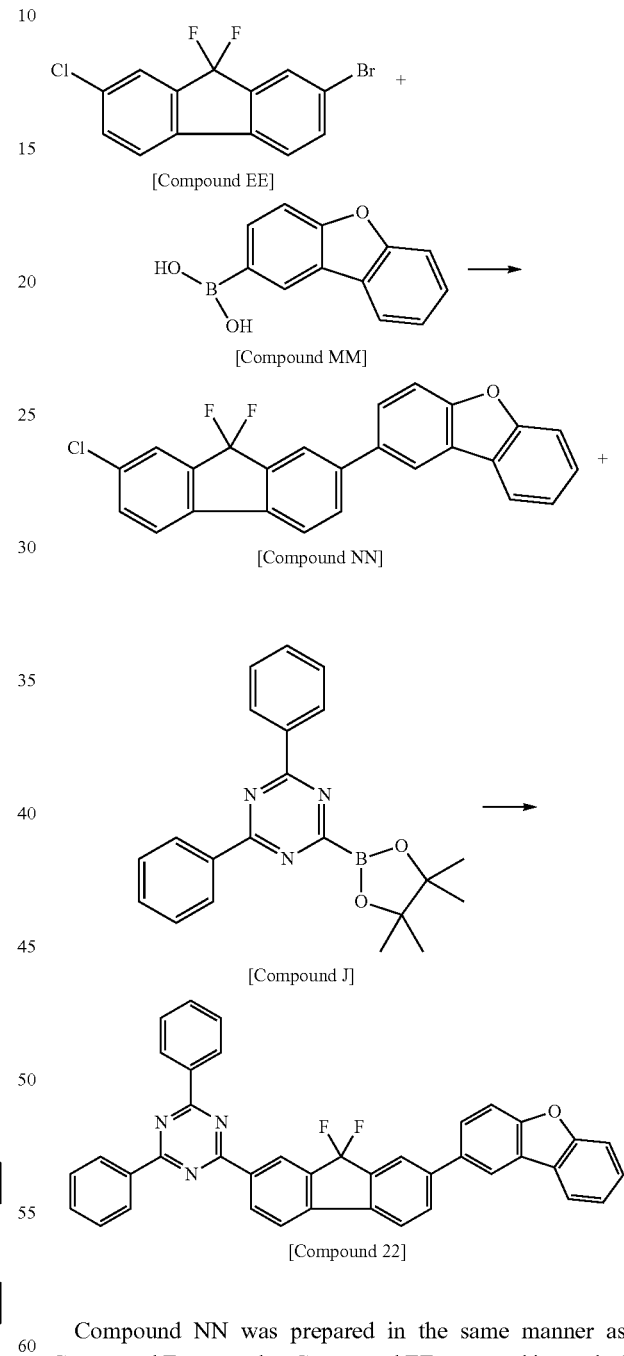

Compound NN was prepared in the same manner as Compound E except that Compound EE was used instead of Compound C, and Compound MM was used instead of Compound E. Next, Compound 22 was prepared in the same manner as Compound 2 except that Compound NN was used instead of Compound E, and Compound J was used instead of Compound F.

Preparation Example 23: Synthesis of the Following Compound 23

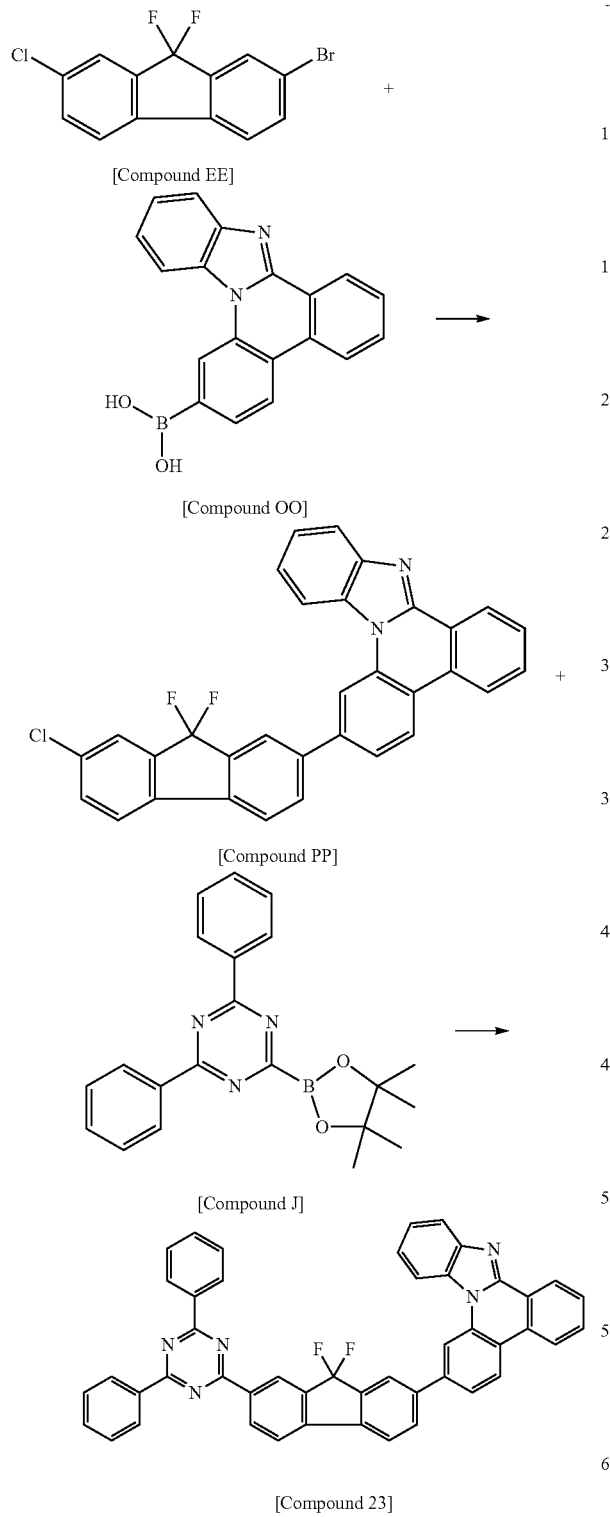

Compound PP was prepared in the same manner as Compound E except that Compound EE was used instead of Compound C, and Compound OO was used instead of Compound E. Next, Compound 23 was prepared in the same manner as Compound 2 except that Compound PP was used instead of Compound E, and Compound J was used instead of Compound F.

<OLED Device Manufacture and Evaluation>

Comparative Example 1

A glass substrate on which indium tin oxide (ITO) was coated as a thin film to a thickness of 1,500 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. A hole injection layer was formed on the substrate by thermal vacuum depositing hexanitrile hexaazatriphenylene (HAT) of the following chemical formula for 5 minutes to a thickness of 100 Å using oxygen plasma.

A hole transfer layer was formed on the hole injection layer by consecutively vacuum depositing 4-4'-bis[N-(1-naphthyl)-N-phenylamino]biphenyl (NPB) of the following chemical formula (700 Å), hexanitrile hexaazatriphenylene (HAT) (50 Å) and 4-4'-bis[N-(1-naphthyl)-N-phenylamino]biphenyl (NPB) (700 Å).

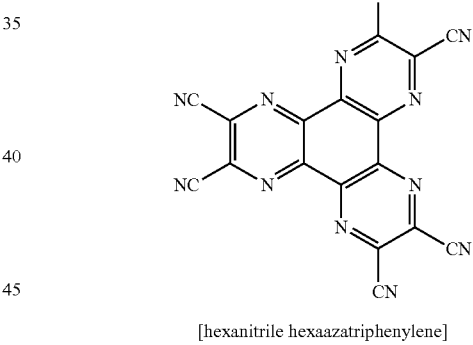

[hexanitrile hexaazatriphenylene]

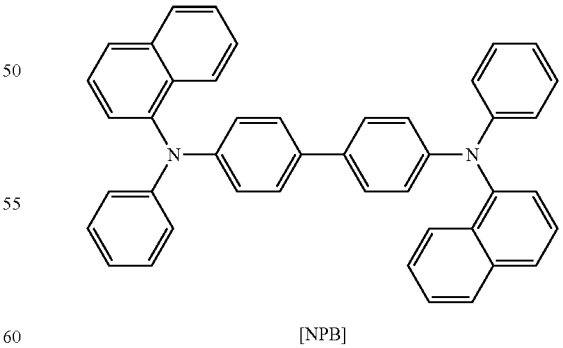

[NPB]

Subsequently, a light emitting layer was formed on the hole transfer layer to a film thickness of 200 Å by vacuum depositing H1 and D1 shown below in a weight ratio of 25:1. An electron transfer layer was formed on the light emitting layer to a thickness of 100 Å of E1.

[H1]

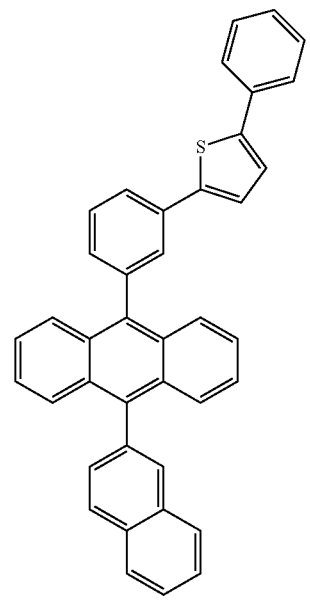

[D1]

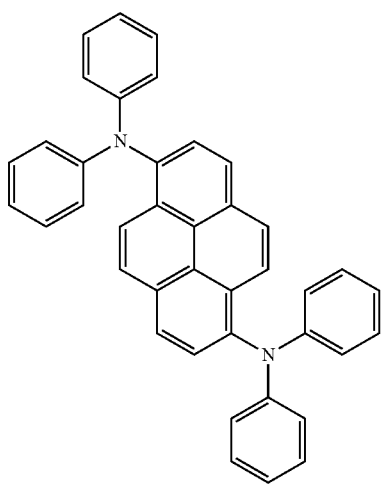

[E1]

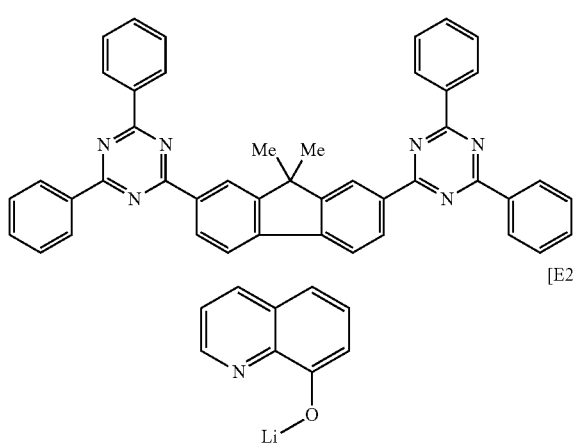

[E2]

[E3]

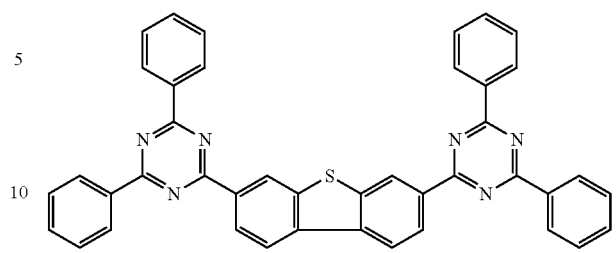

An electron injection and electron transfer layer was formed on the electron transfer layer to a thickness of 200 Å by vacuum depositing E1 and E2 in a weight ratio of 1:1. A cathode was formed on the electron injection and transfer layer by depositing lithium fluoride (LiF) to a thickness of 15 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2\times10^{-7}$ torr to $5\times10^{-8}$ torr.

Comparative Example 2

An experiment was carried out in the same manner as in Comparative Example 1 except that E3 was used instead of the electron injection and electron transfer layer E1.

Example 1

An experiment was carried out in the same manner as in Comparative Example 1 except that Compound 1 was used instead of the electron injection and electron transfer layer E1.

Example 2

An experiment was carried out in the same manner as in Comparative Example 1 except that Compound 4 was used instead of the electron injection and electron transfer layer E1.

Example 3

An experiment was carried out in the same manner as in Comparative Example 1 except that Compound 9 was used instead of the electron injection and electron transfer layer E1.

Example 4

An experiment was carried out in the same manner as in Comparative Example 1 except that Compound 11 was used instead of the electron injection and electron transfer layer E1.

Example 5

An experiment was carried out in the same manner as in Comparative Example 1 except that Compound 12 was used instead of the electron injection and electron transfer layer E1.

Example 6

An experiment was carried out in the same manner as in Comparative Example 1 except that Compound 14 was used instead of the electron injection and electron transfer layer E1.

Example 7

An experiment was carried out in the same manner as in Comparative Example 1 except that Compound 16 was used instead of the electron injection and electron transfer layer E1.

Example 8

An experiment was carried out in the same manner as in Comparative Example 1 except that Compound 18 was used instead of the electron injection and electron transfer layer E1.

Results of testing the organic light emitting devices manufactured using each of the compounds of Comparative Examples 1 and 2, and Examples 1 to 8 are shown in Table 1.

TABLE 1

| Test Example 10 mA/cm² | Material Used in Electron Injection and Electron Transfer Layer | Voltage (V) | Current Efficiency (cd/A) |
|---|---|---|---|
| Comparative Example 1 | E1 + E2 | 4.2 | 4.6 |
| Comparative Example 2 | E3 + E2 | 4.3 | 4.7 |
| Example 1 | Compound 1 + E2 | 4.1 | 4.2 |
| Example 2 | Compound 4 + E2 | 4.1 | 4.1 |
| Example 3 | Compound 9 + E2 | 4.3 | 4.5 |
| Example 4 | Compound 11 + E2 | 4.2 | 4.3 |
| Example 5 | Compound 12 + E2 | 4.2 | 4.4 |
| Example 6 | Compound 14 + E2 | 4.2 | 4.3 |
| Example 7 | Compound 16 + E2 | 4.0 | 4.1 |
| Example 8 | Compound 18 + E2 | 4.0 | 4.2 |

From the above device evaluation results, it can be seen that the heterocyclic compound according to the present specification may be used as materials of an organic material layer of organic electronic devices including organic light emitting devices, and organic electronic devices including organic light emitting devices using the heterocyclic compound exhibits excellent properties in efficiency, driving voltage and the like.

The invention claimed is:

1. A compound represented by any one of the following Chemical Formula 2 to Chemical Formula 4:

[Chemical Formula 2]

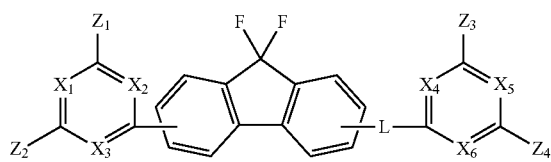

[Chemical Formula 3]

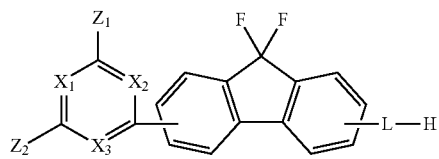

[Chemical Formula 4]

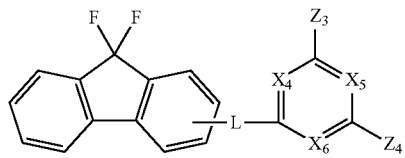

wherein, in Chemical Formula 2 to Chemical Formula 4,

L is a direct bond; a substituted or unsubstituted arylene group; or a substituted or unsubstituted heteroarylene group;

$X_1$ to $X_6$ are N or CH;

at least one of $X_1$ to $X_3$ is N;

at least one of $X_4$ to $X_6$ is N; and $Z_1$ to $Z_4$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkoxy group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

2. The compound of claim 1, wherein the compound of Chemical Formula 2 is represented by any one of the following Chemical Formula 5 to Chemical Formula 8:

[Chemical Formula 5]

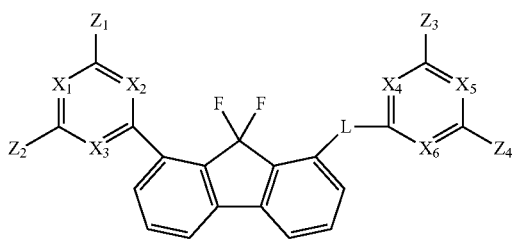

[Chemical Formula 6]

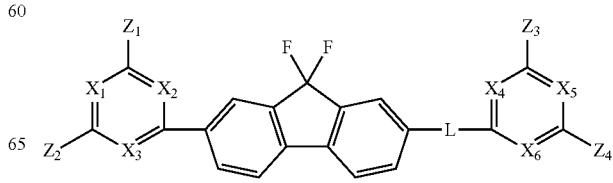

127

-continued

[Chemical Formula 7]

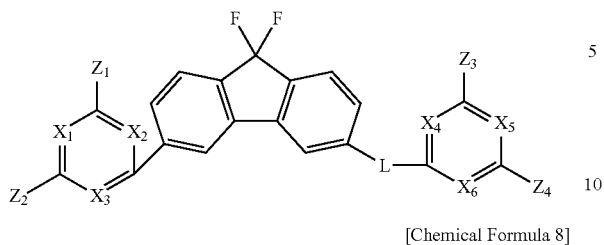

[Chemical Formula 8]

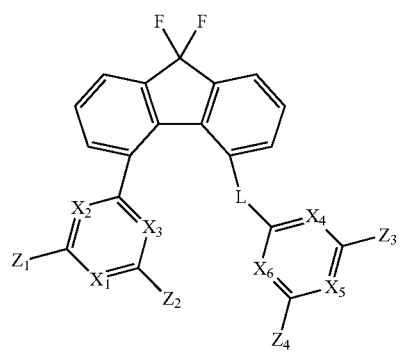

wherein, in Chemical Formula 5 to Chemical Formula 8, definitions of L, $X_1$ to $X_6$ and $Z_1$ to $Z_4$ are the same as in Chemical Formula 2.

3. The compound of claim 1, wherein the compound of Chemical Formula 3 is represented by any one of the following Chemical Formula 9 to Chemical Formula 12:

[Chemical Formula 9]

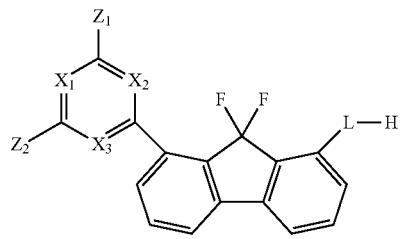

[Chemical Formula 10]

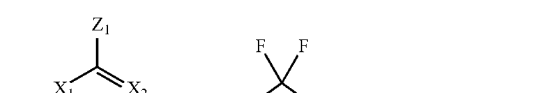

[Chemical Formula 11]

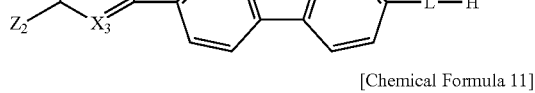

128

-continued

[Chemical Formula 12]

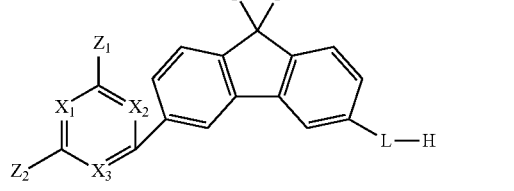

wherein, in Chemical Formula 9 to Chemical Formula 12, definitions of L, $X_1$ to $X_3$, $Z_1$ and $Z_2$ are the same as in Chemical Formula 3.

4. The compound of claim 1, wherein the compound of Chemical Formula 4 is represented by any one of the following Chemical Formula 13 to Chemical Formula 16:

[Chemical Formula 13]

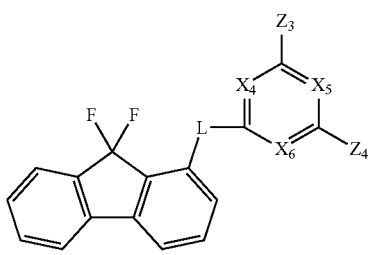

[Chemical Formula 14]

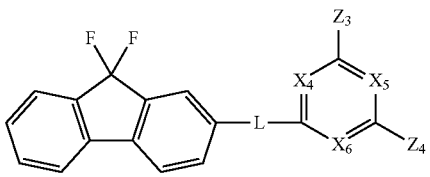

[Chemical Formula 15]

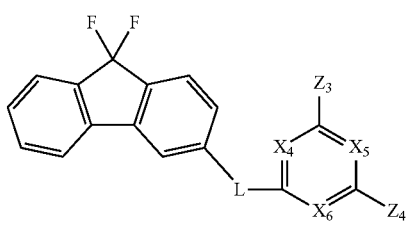

[Chemical Formula 16]

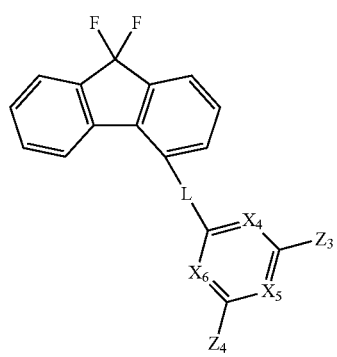

wherein, in Chemical Formula 13 to Chemical Formula 16,
definitions of L, $X_4$ to $X_6$, $Z_3$ and $Z_4$ are the same as in Chemical Formula 4.
5. A compound selected from among the following structures:
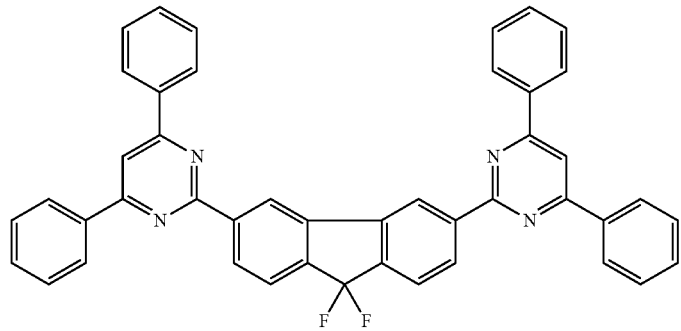
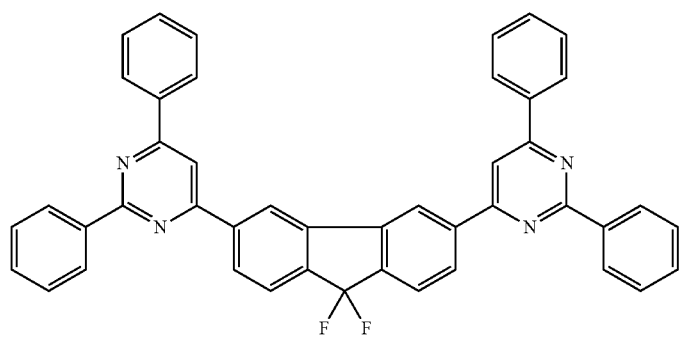
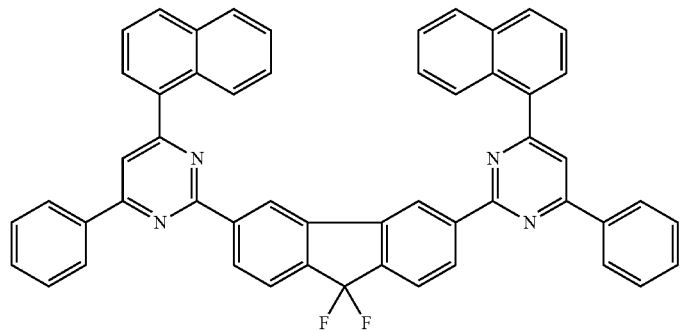
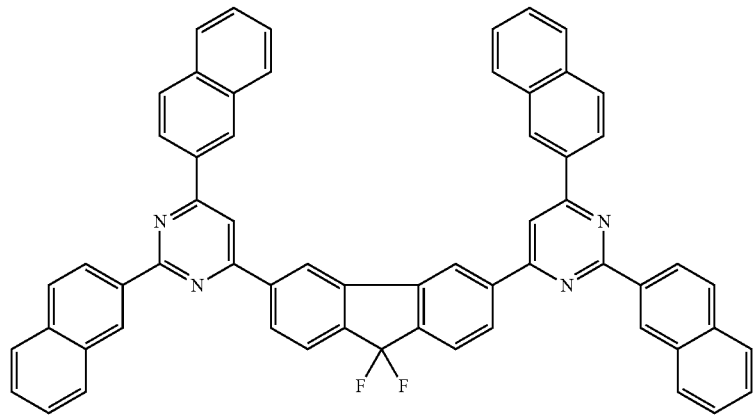

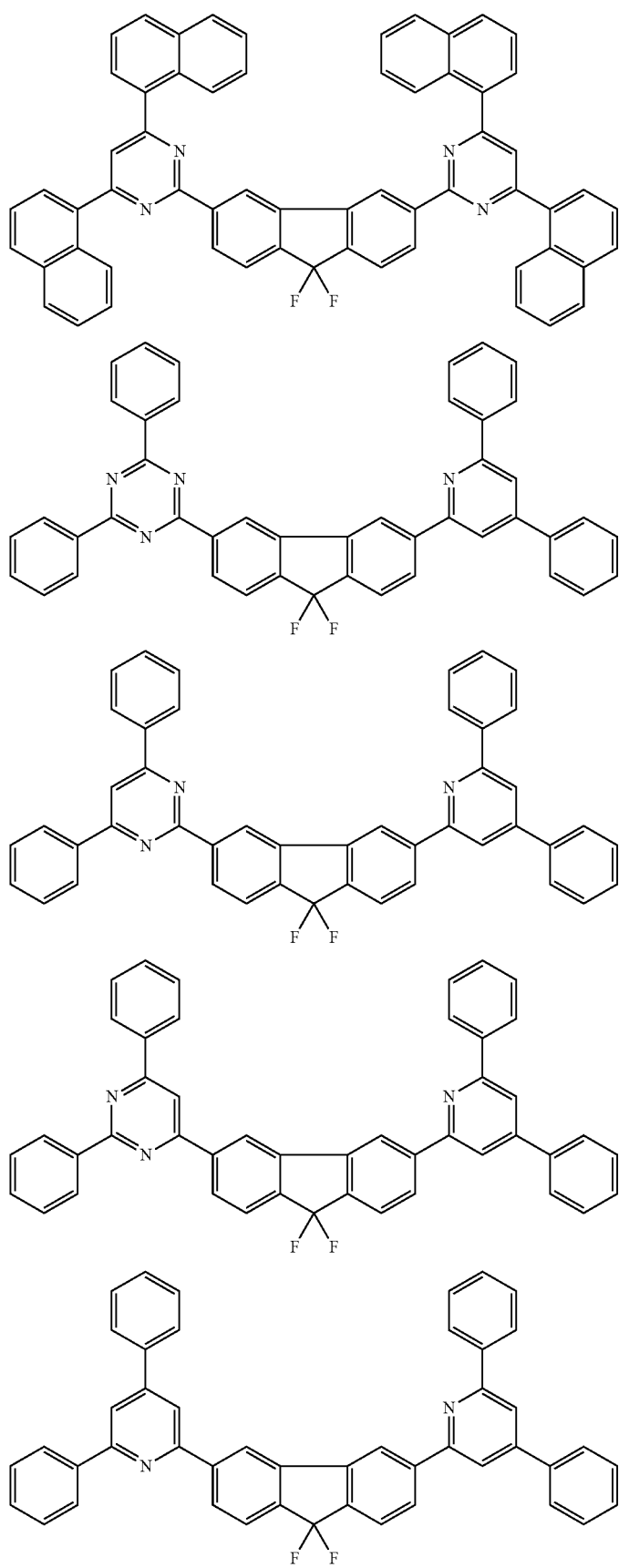

-continued
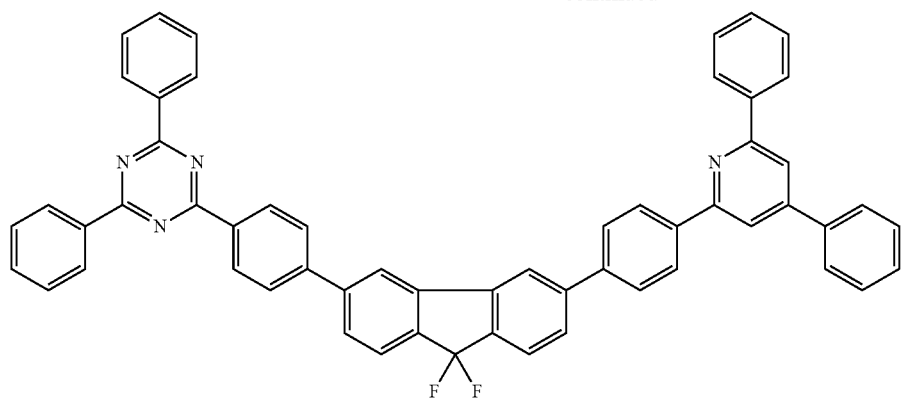
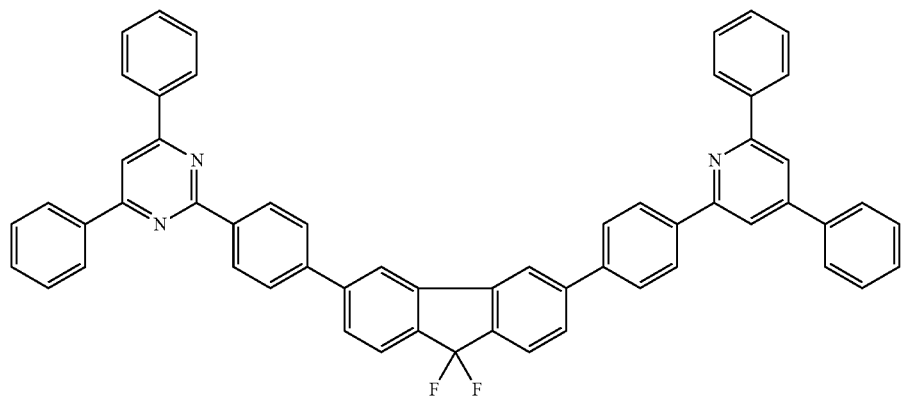
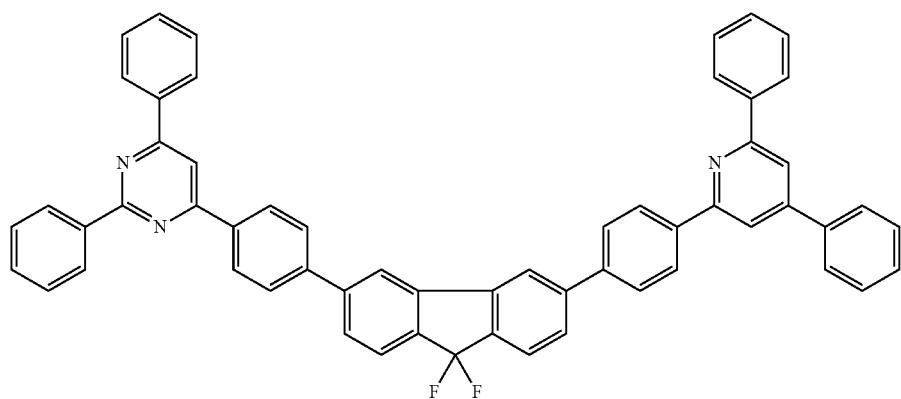
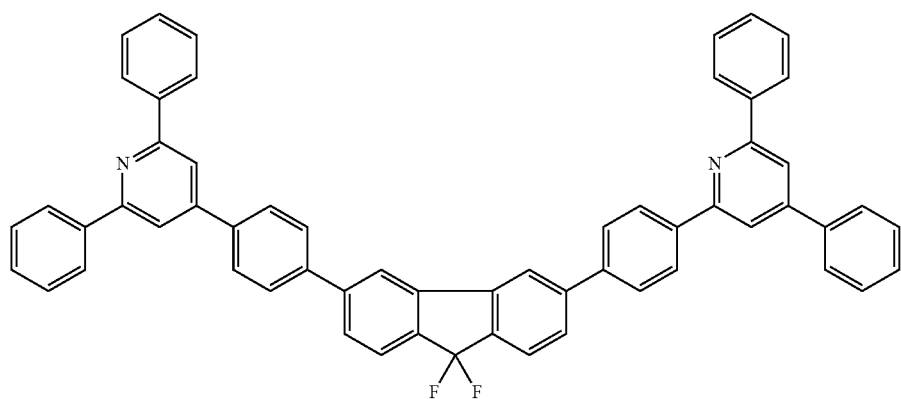

-continued
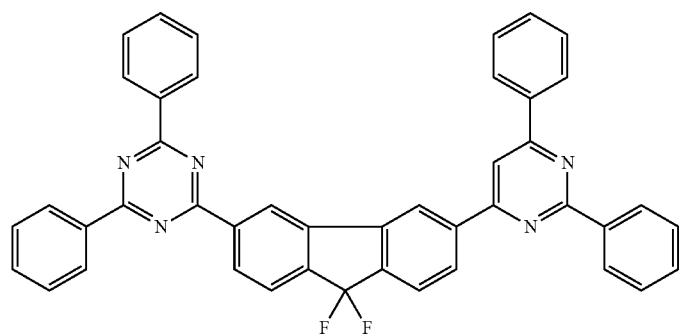
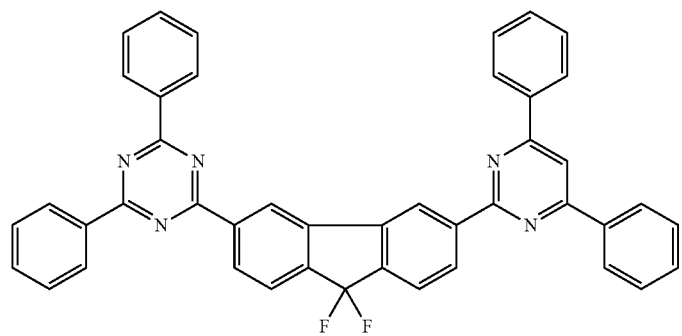
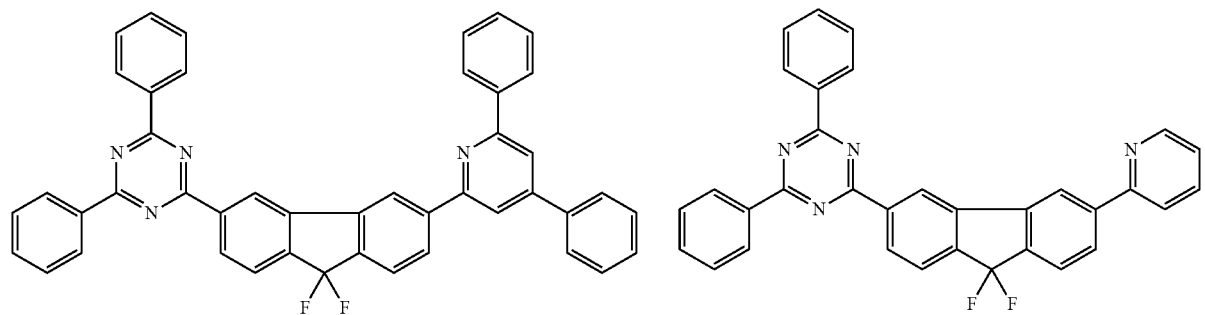
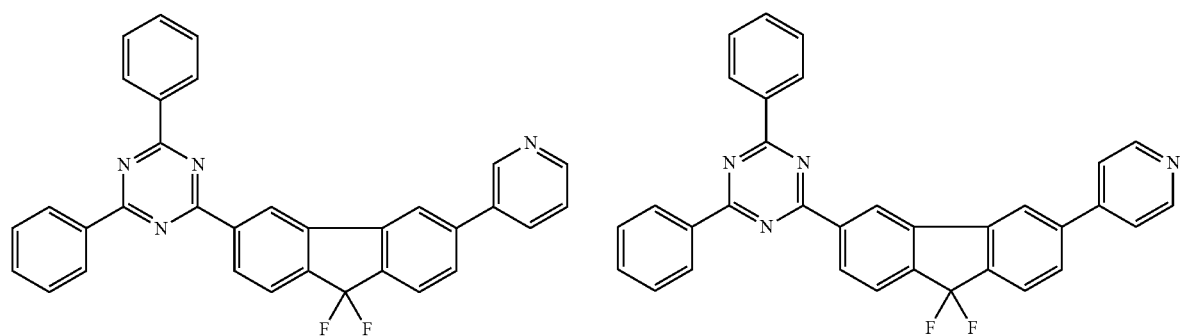
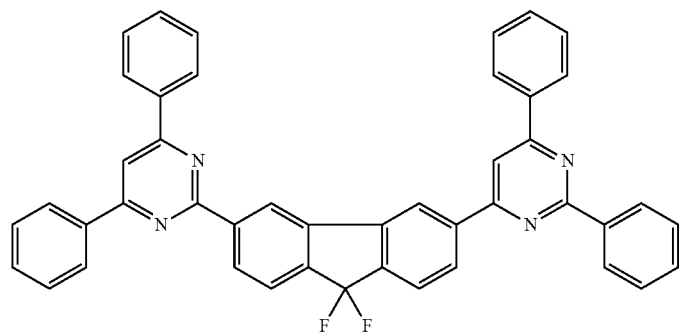

-continued
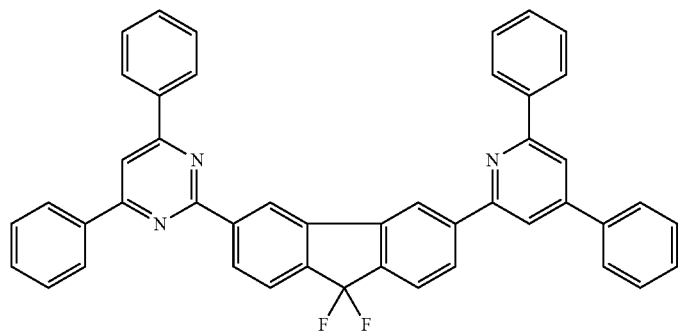
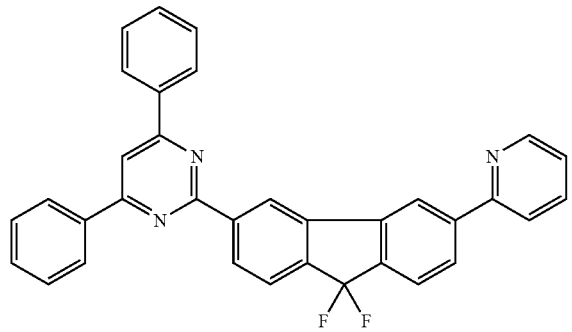
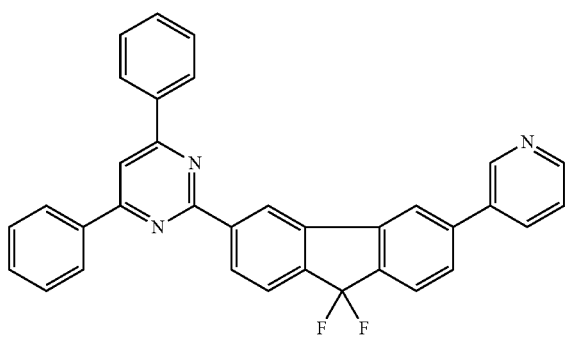
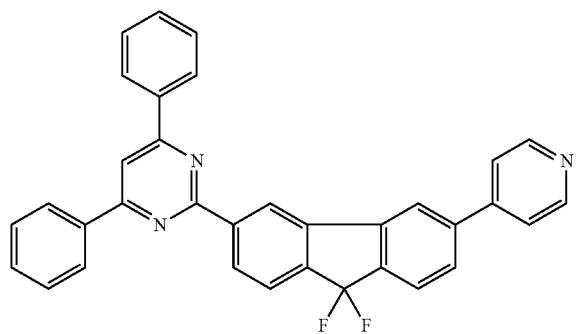
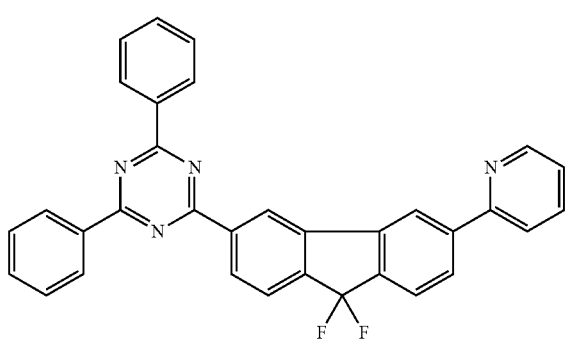
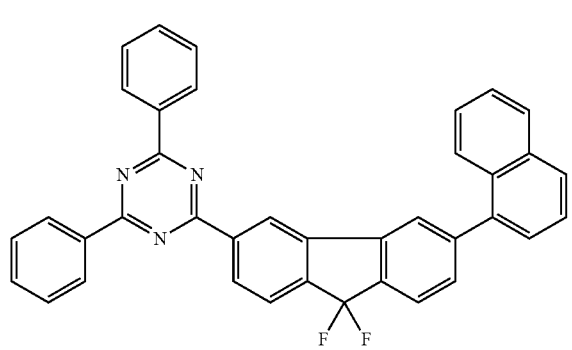
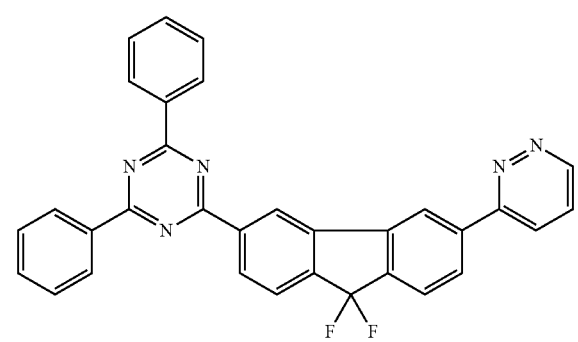
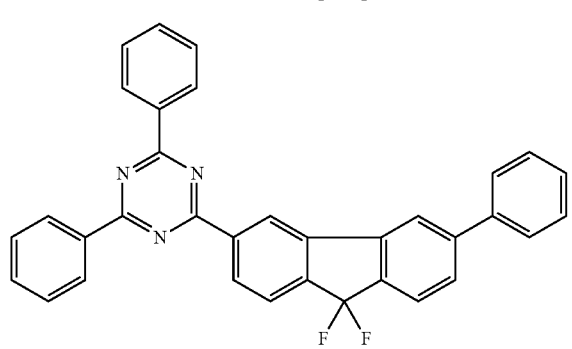
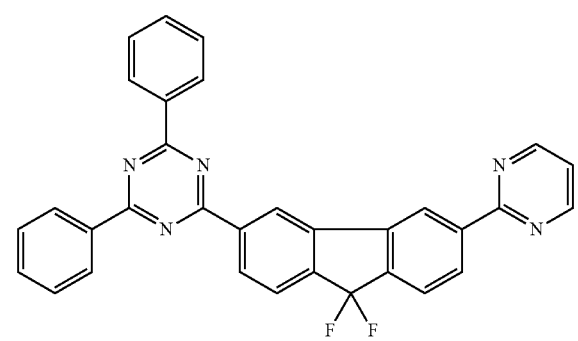

-continued
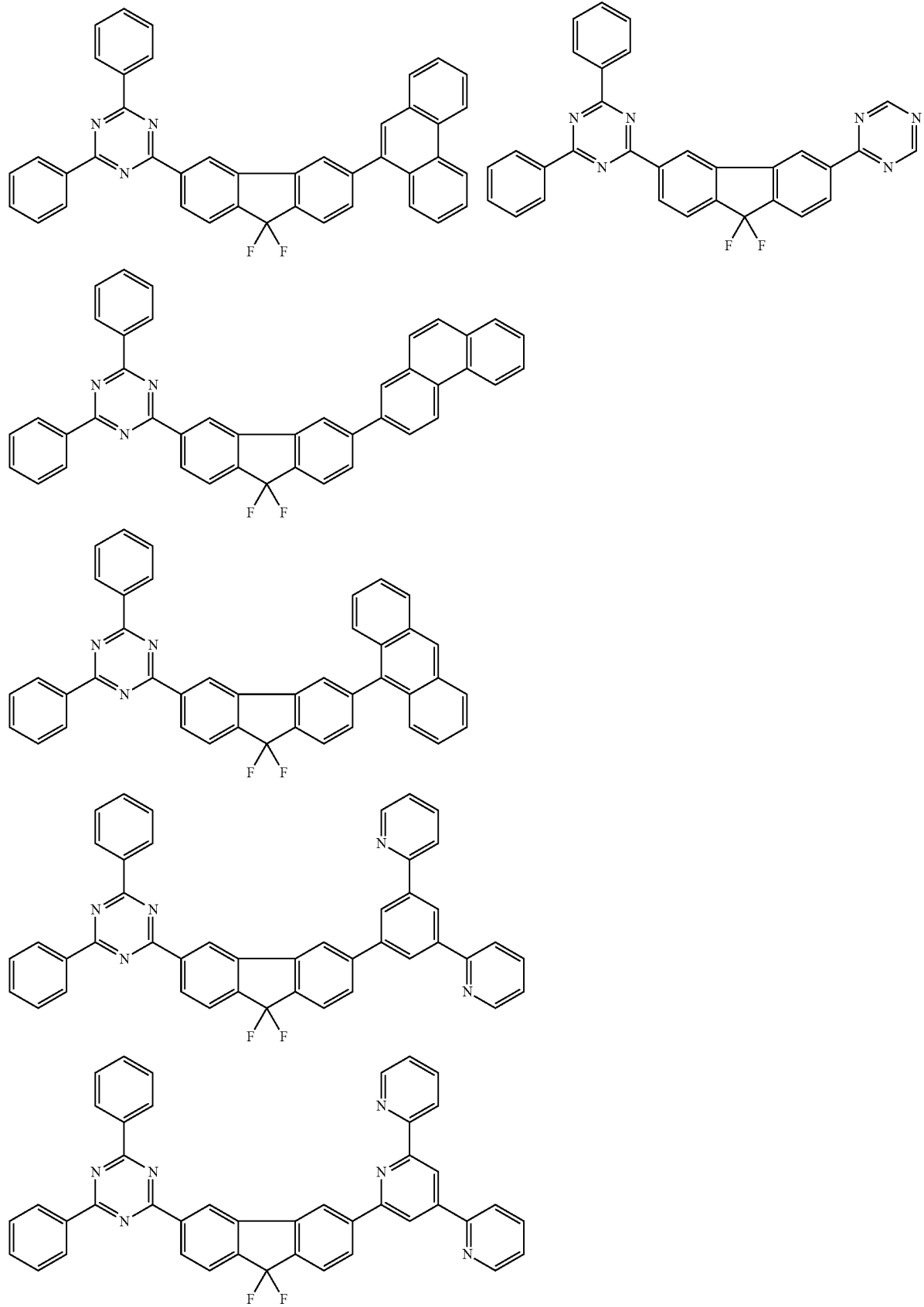

-continued
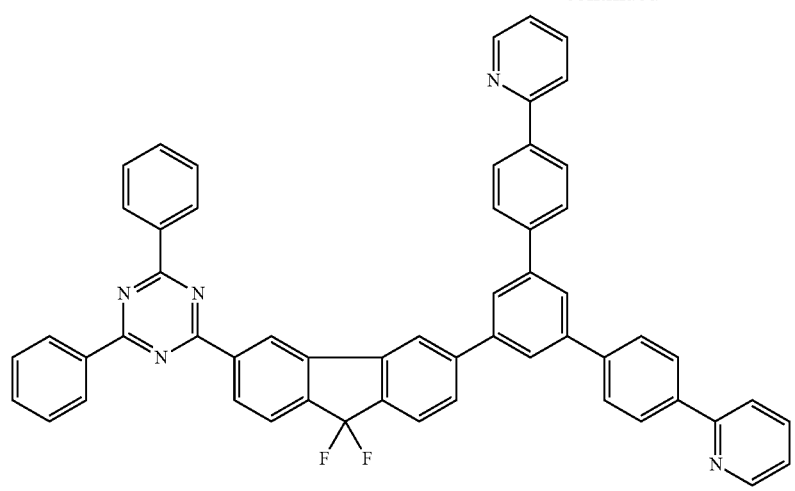
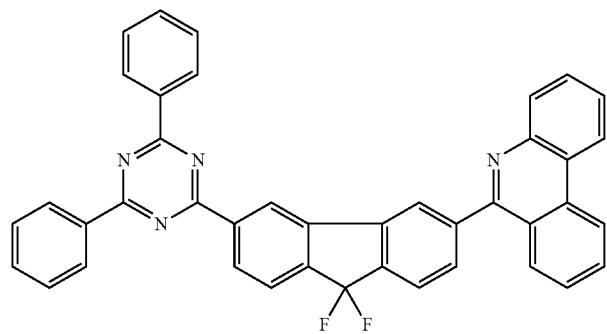
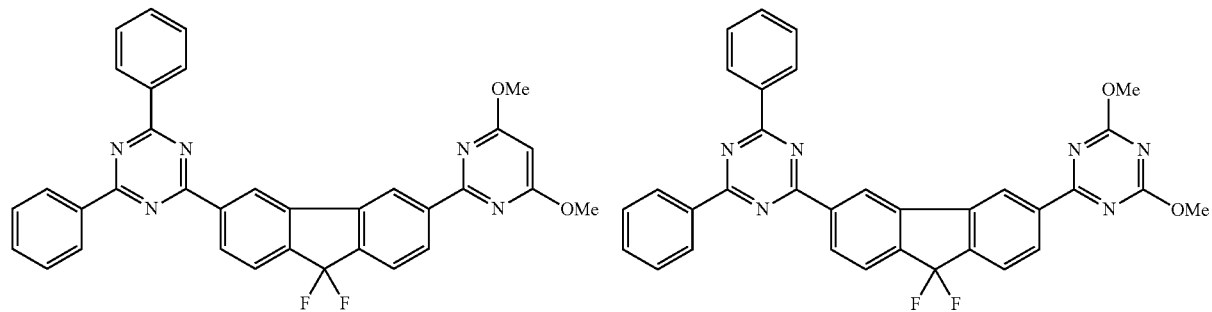
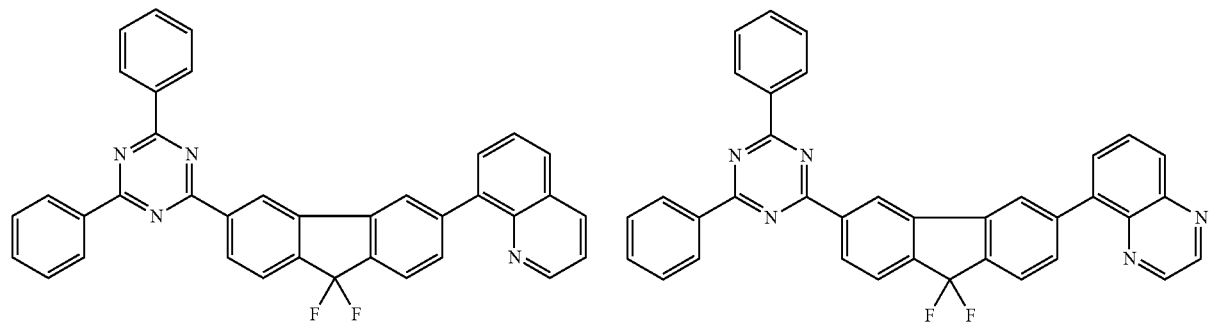

-continued
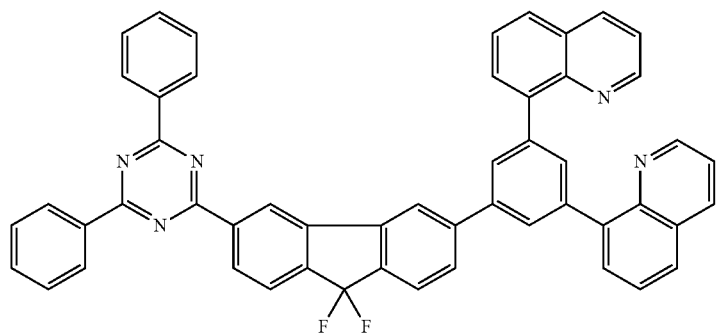
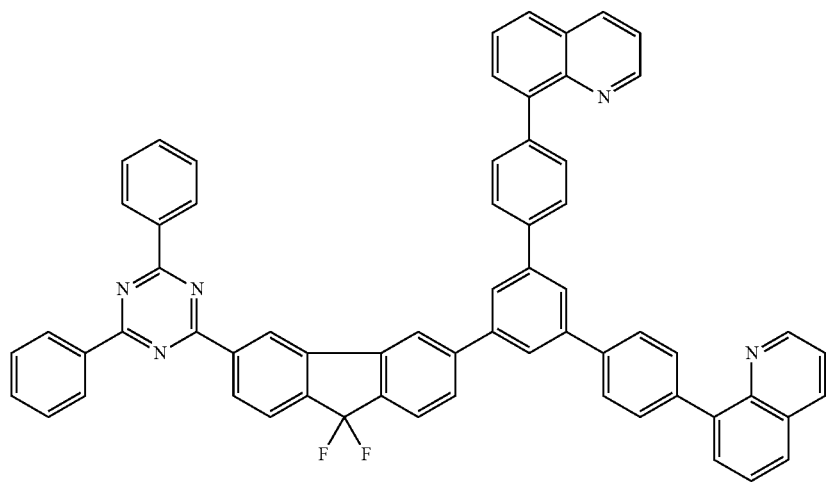
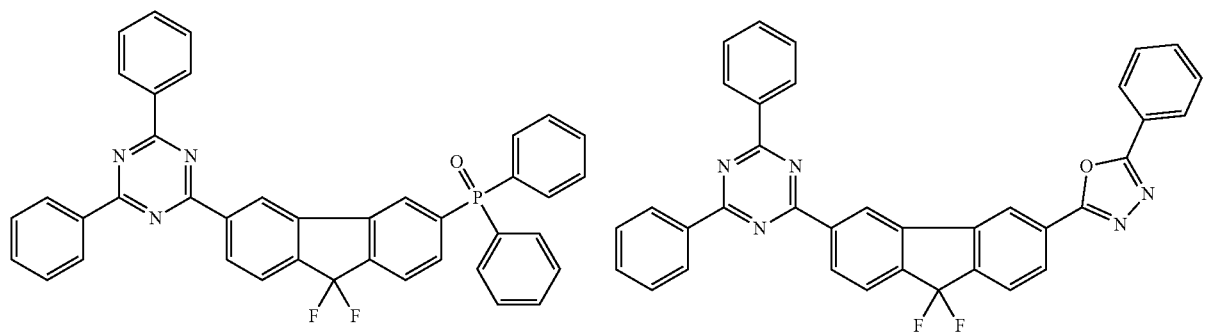
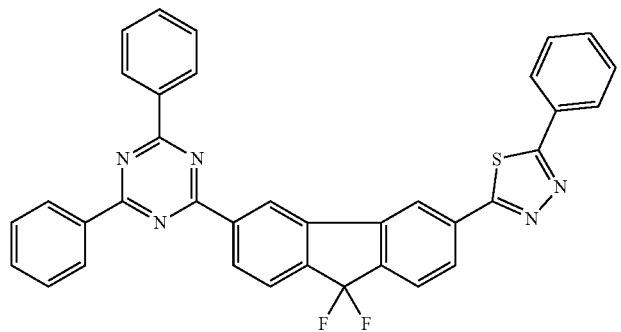

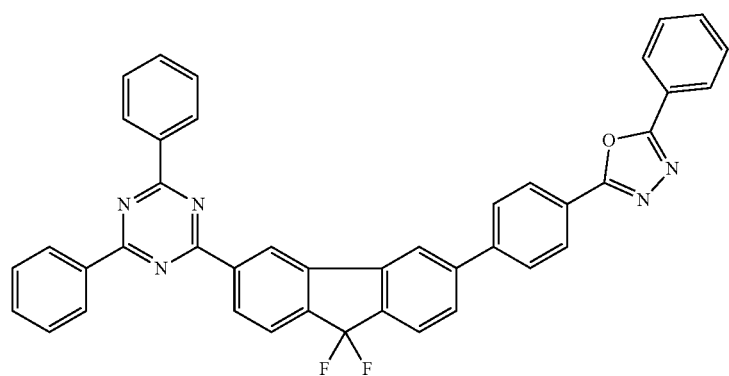
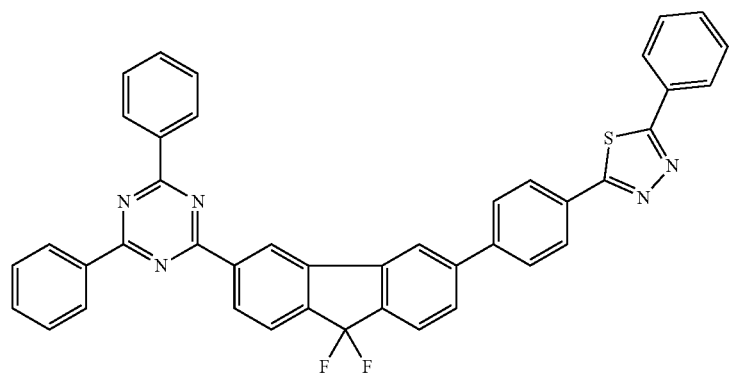
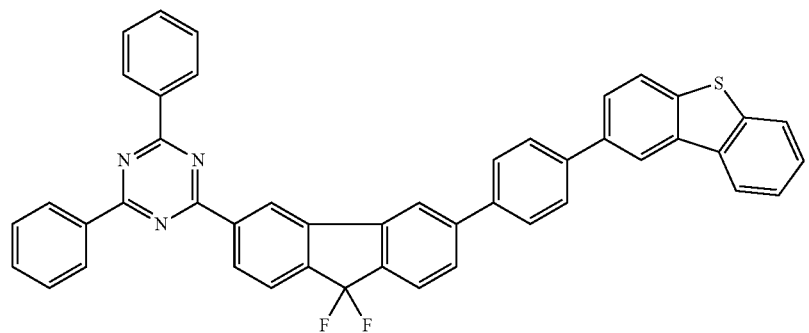
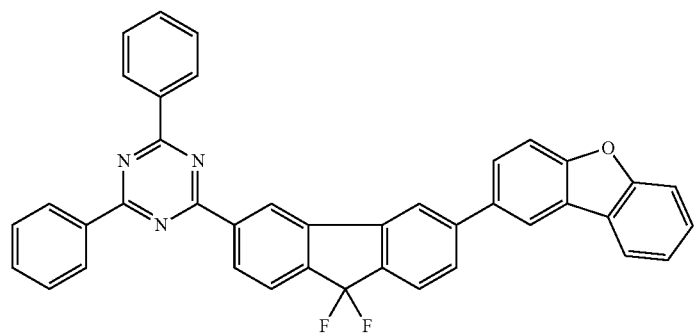

-continued
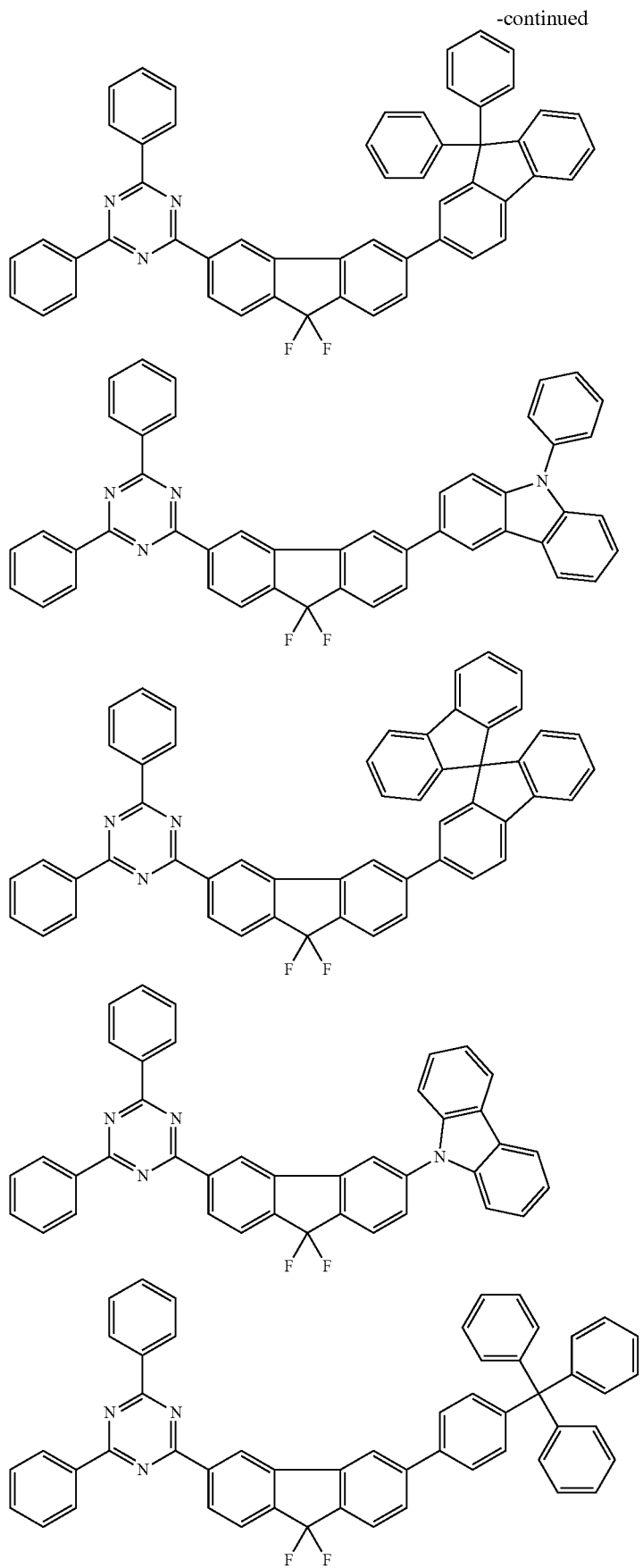

-continued
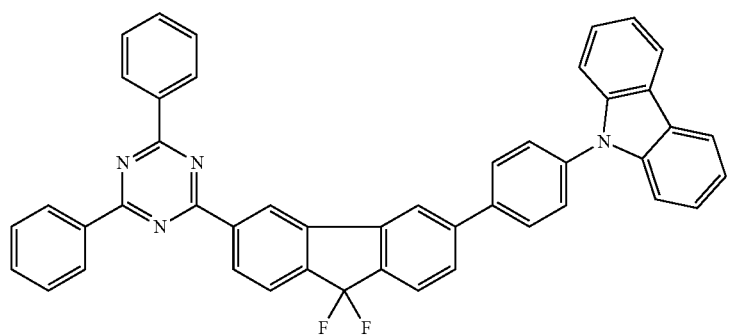
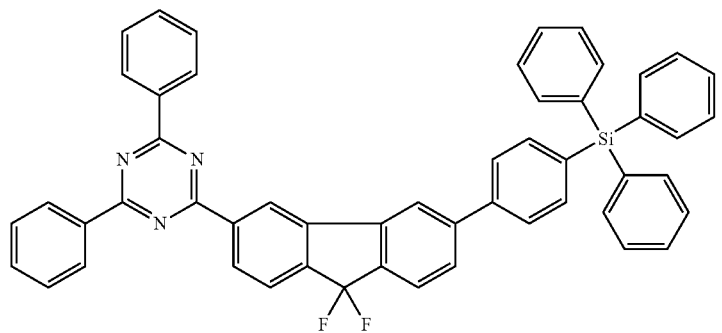
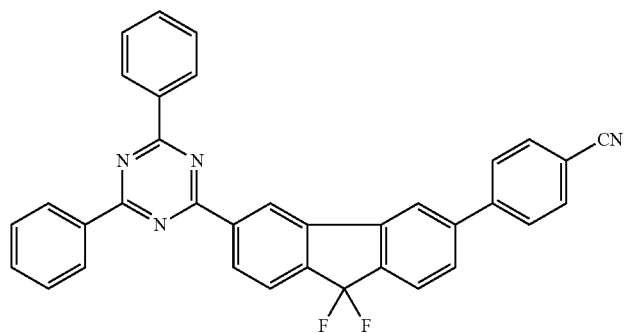
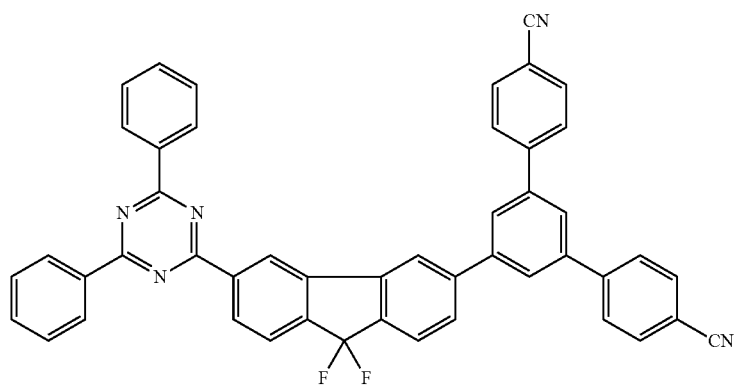
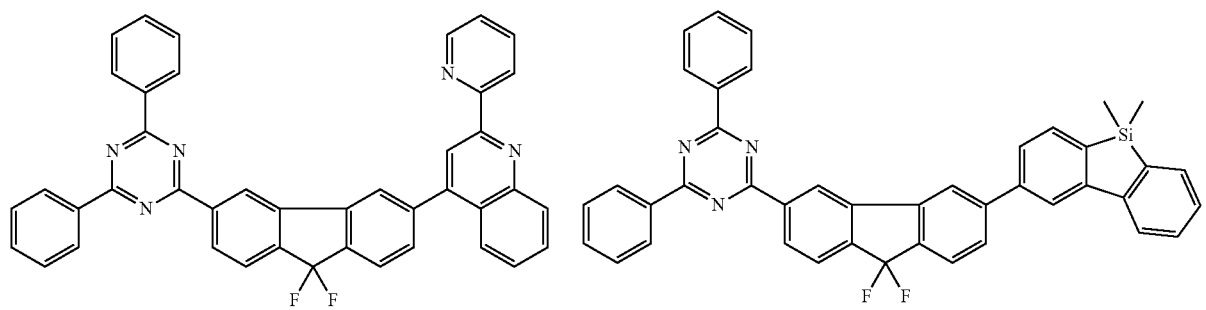

-continued
151
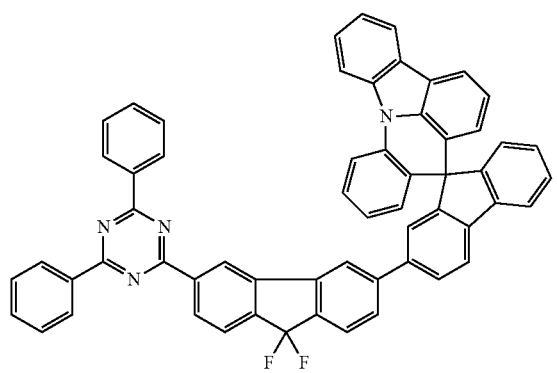
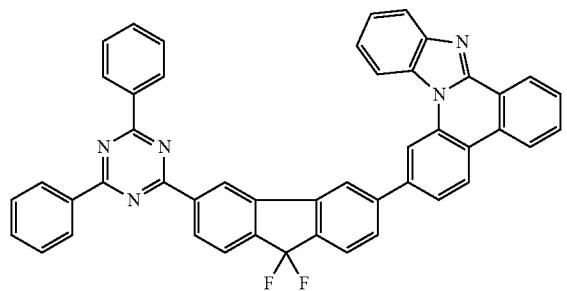
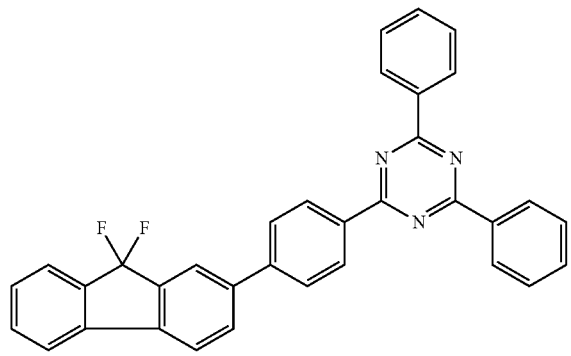
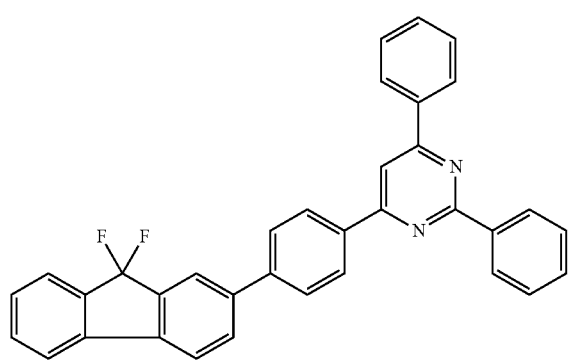
152
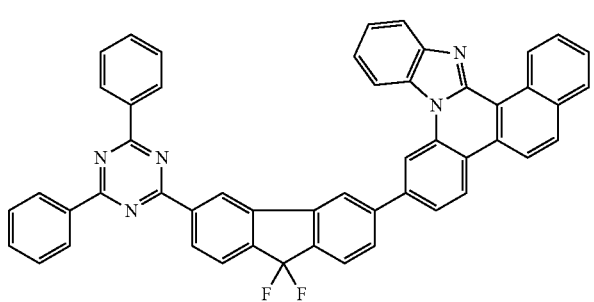
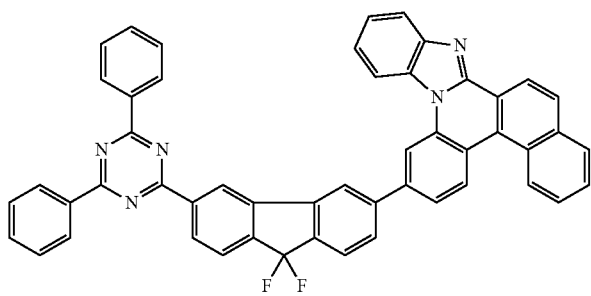
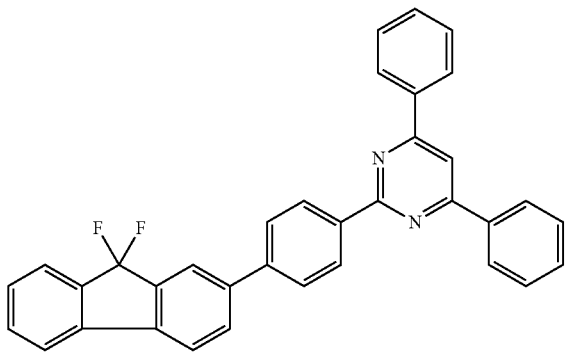
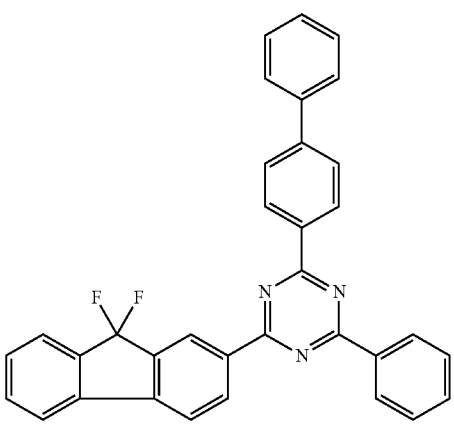

153
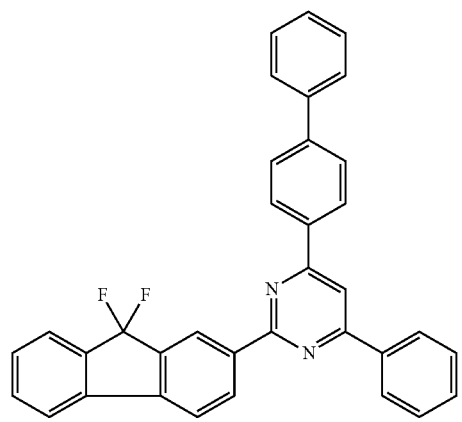
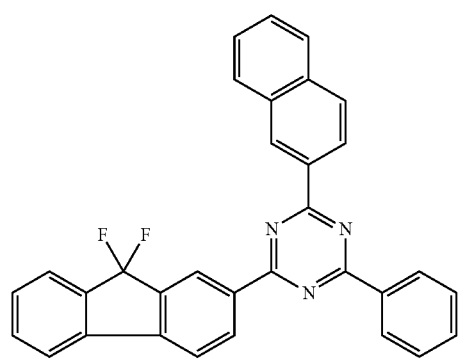
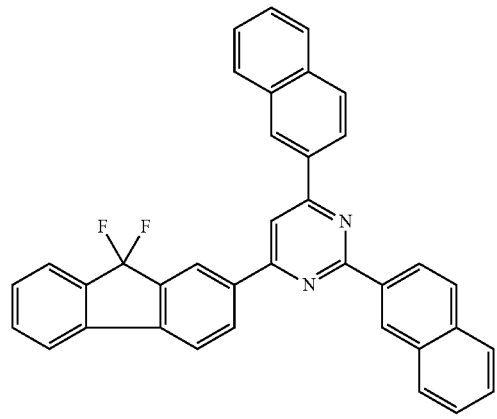
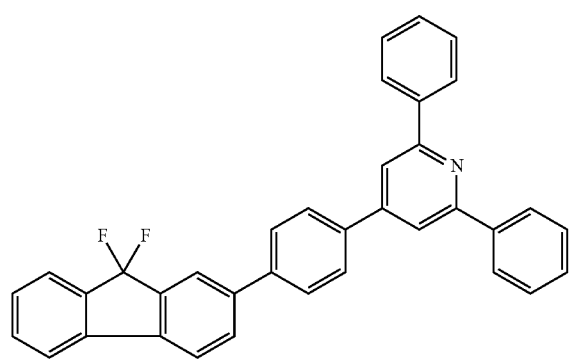
154
-continued
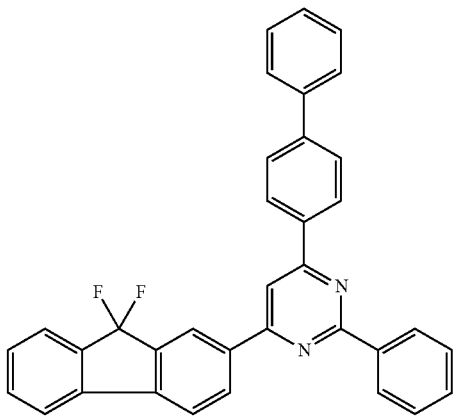
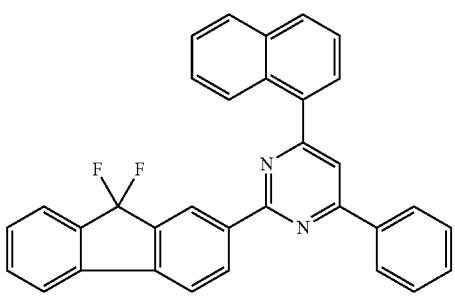
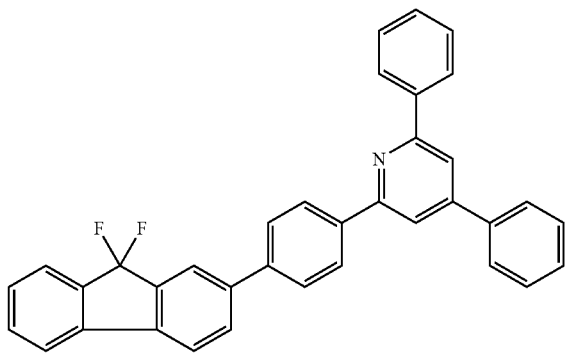
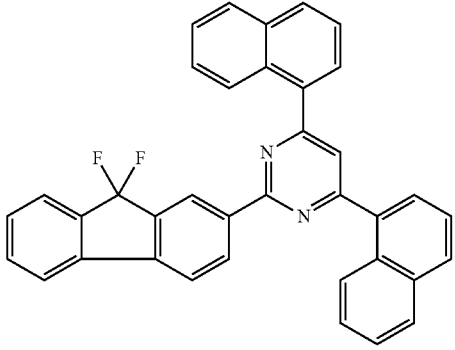

155
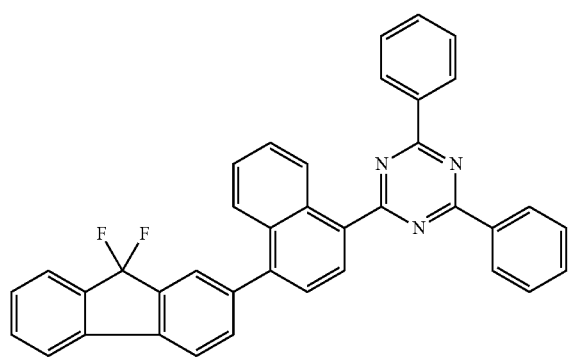
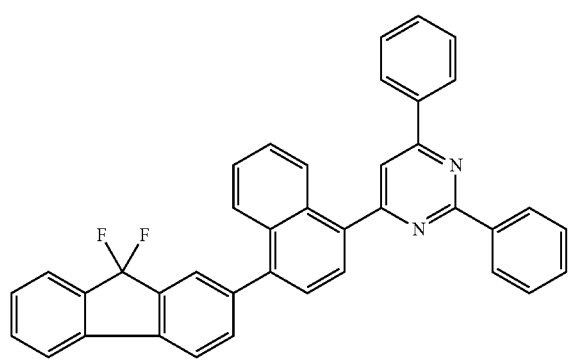
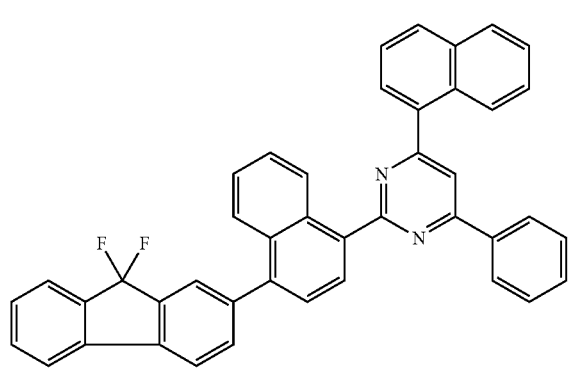
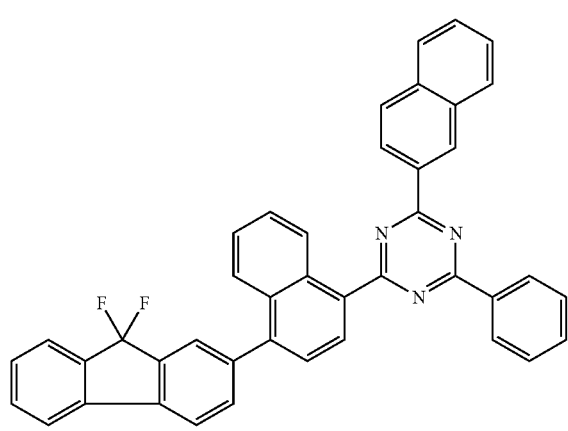
156
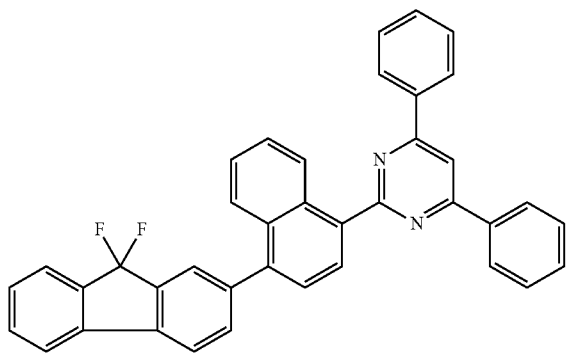
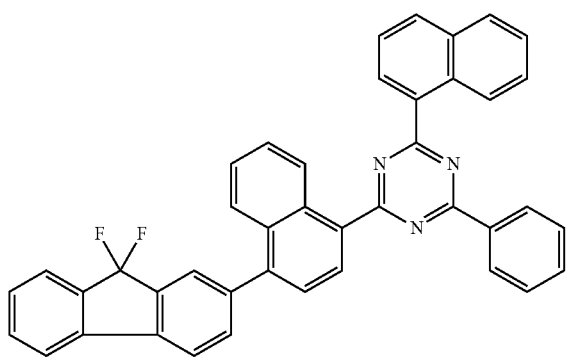
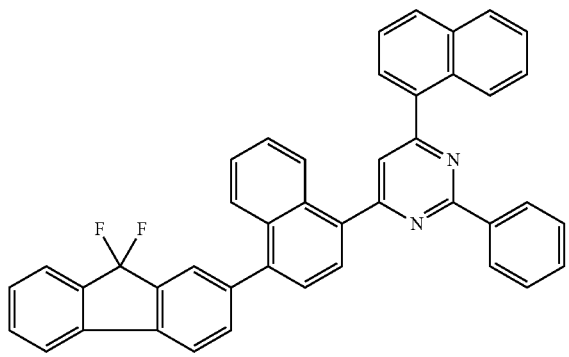
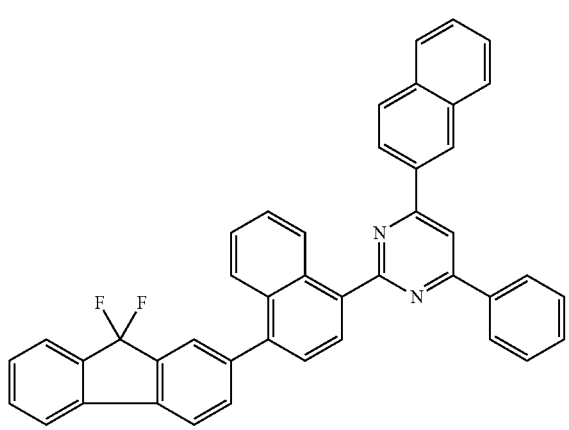

157
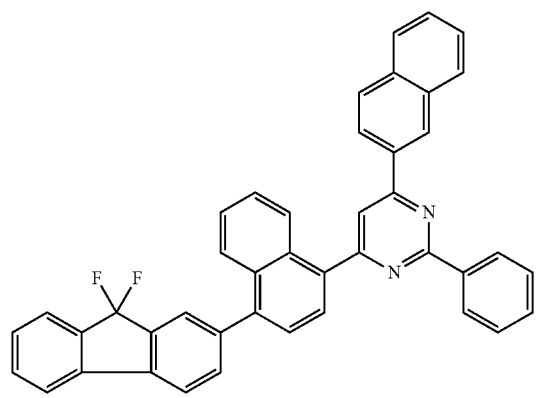
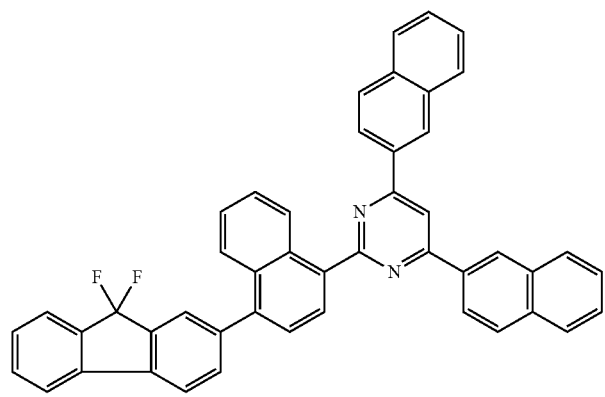
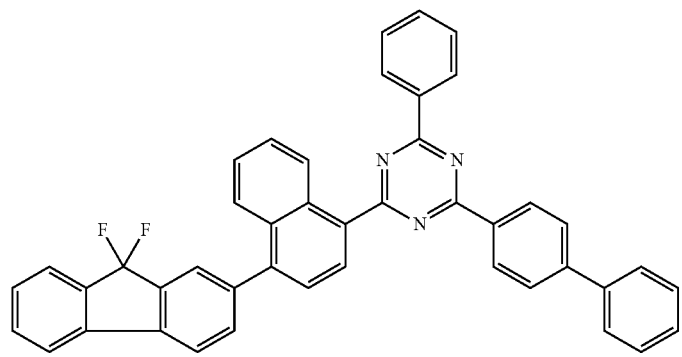
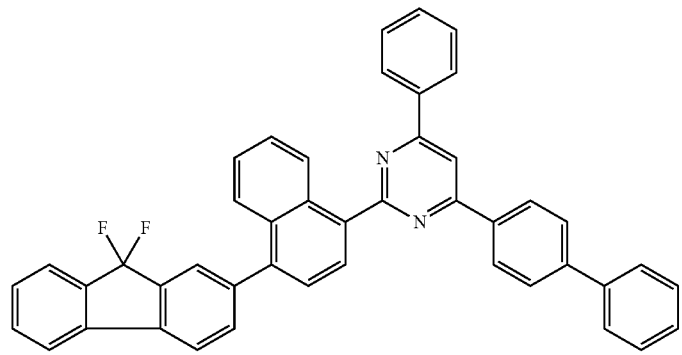
158
-continued
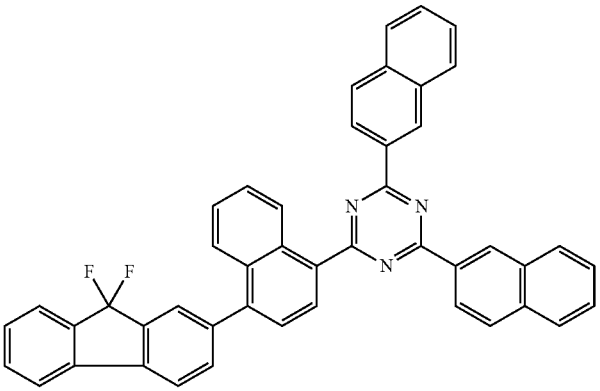
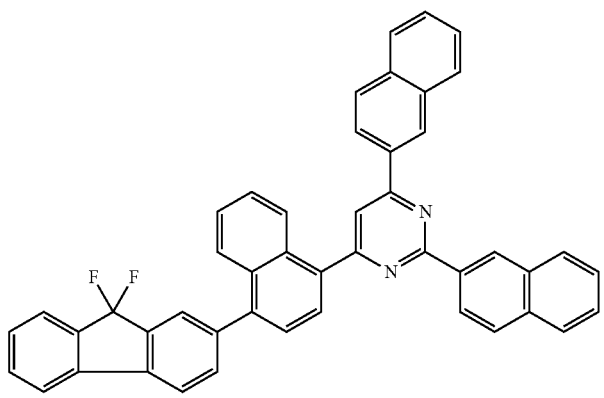

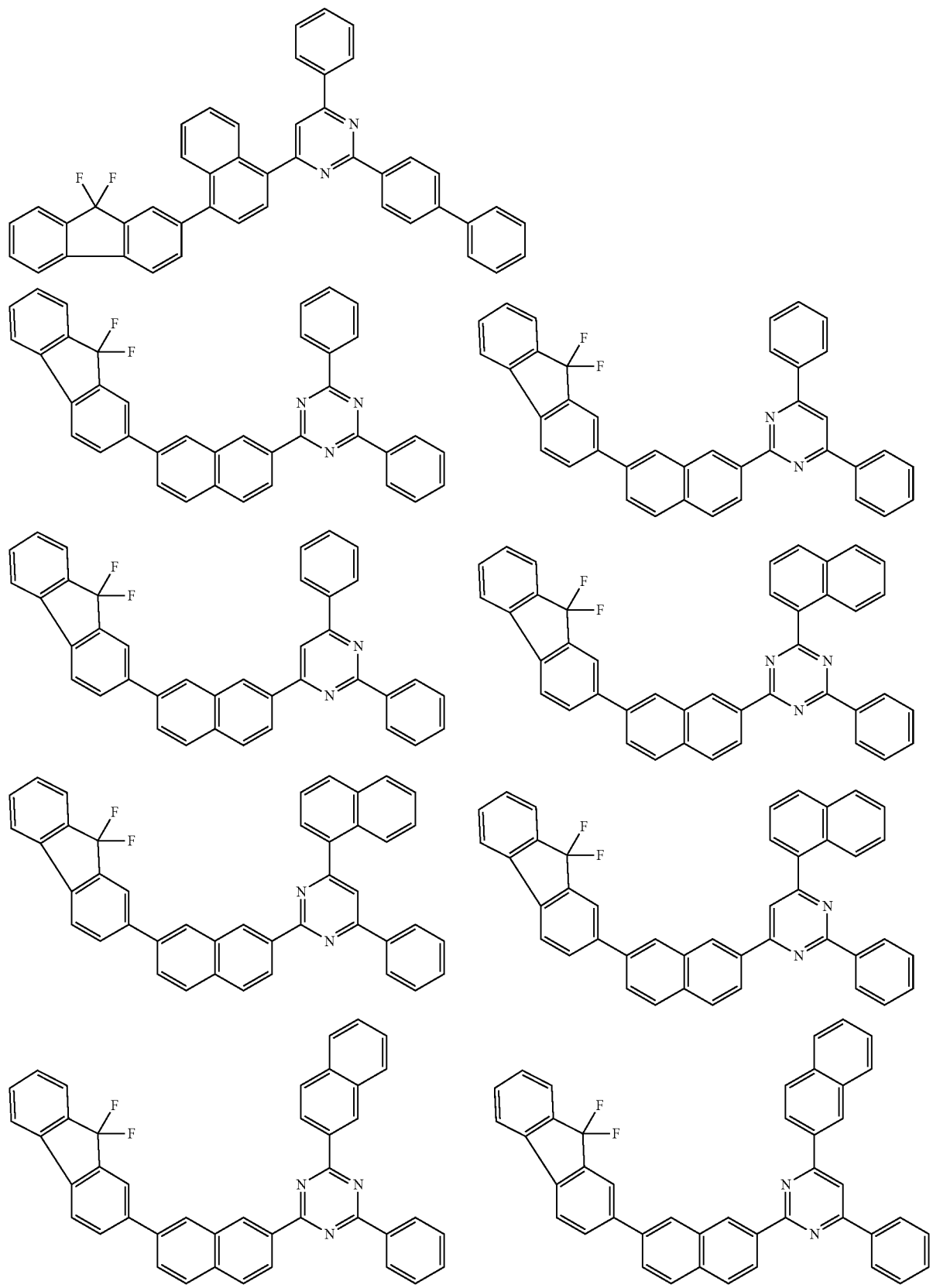

-continued
161
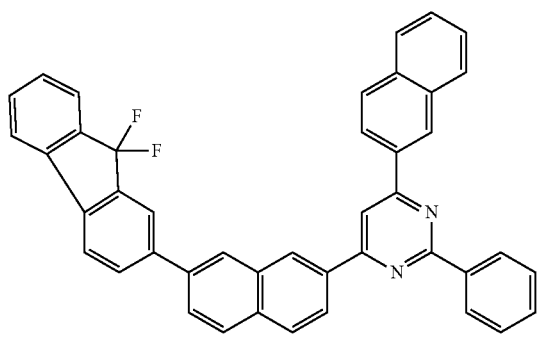
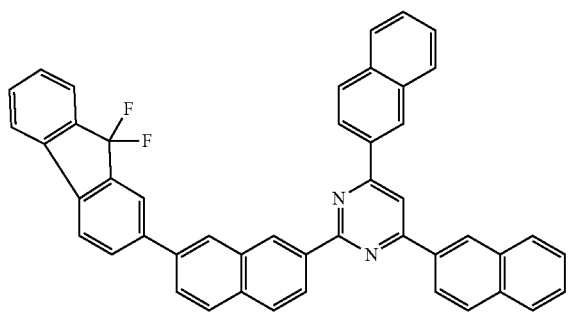
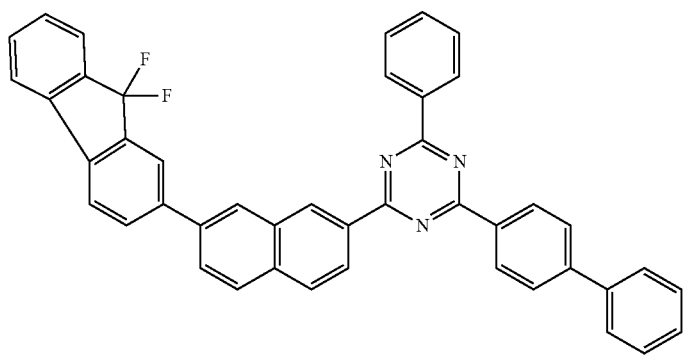
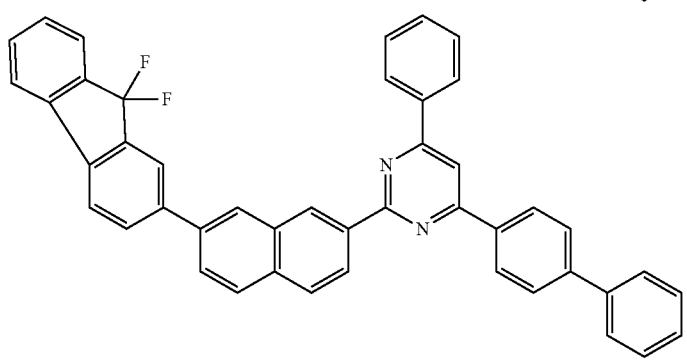
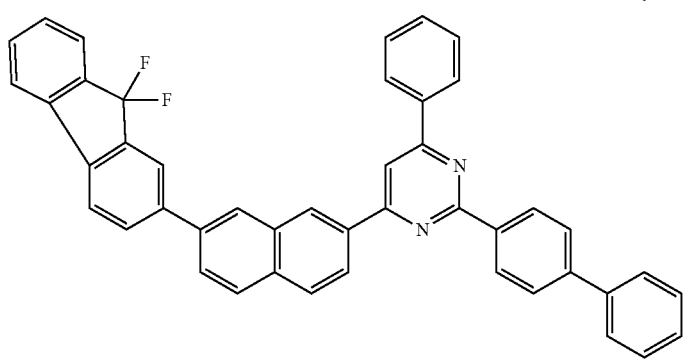
162
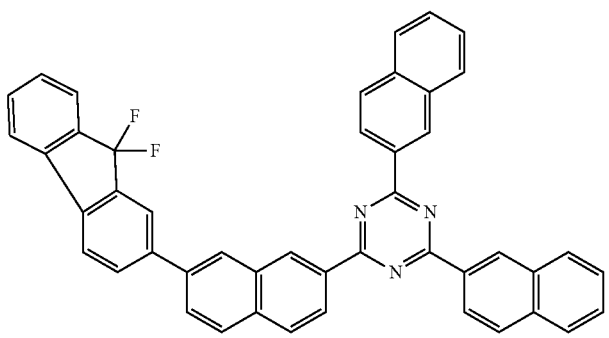
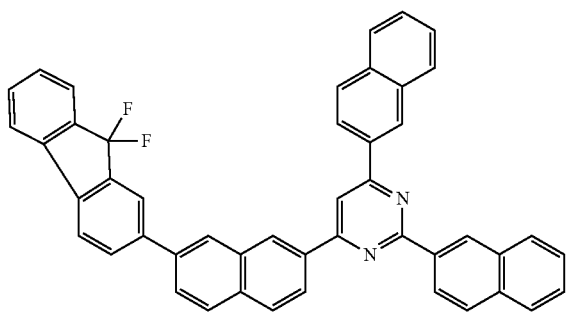

-continued
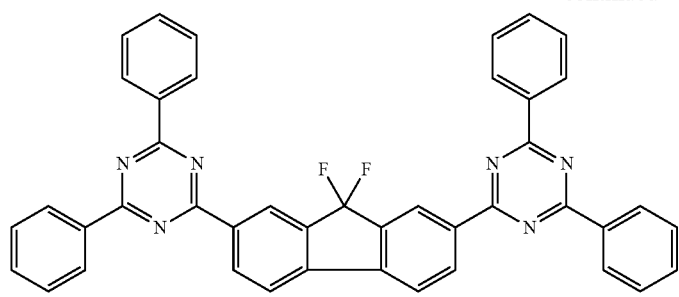
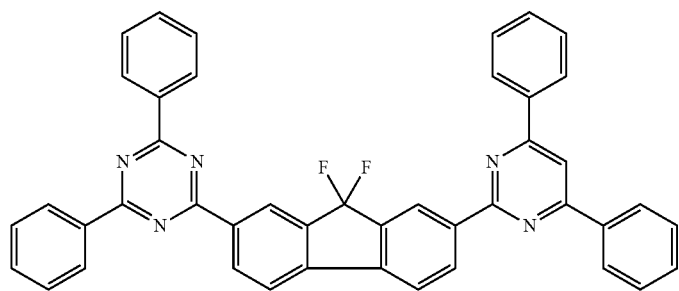
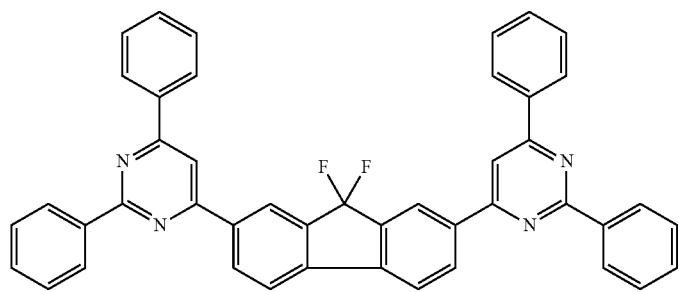
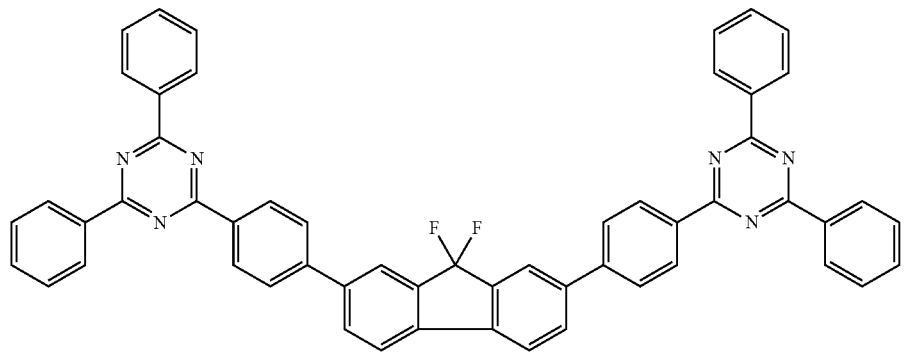
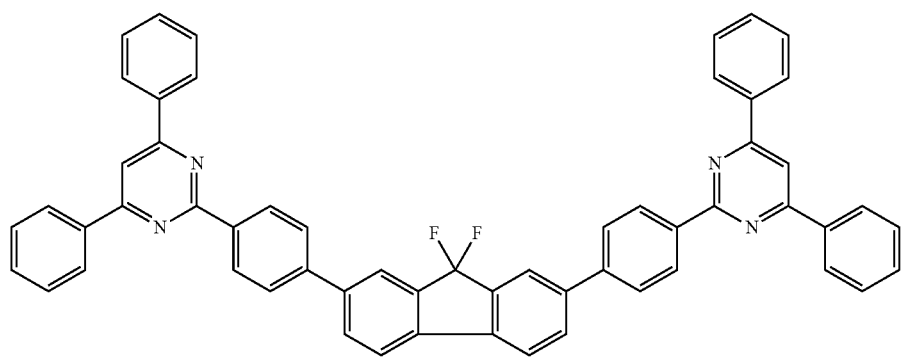

-continued
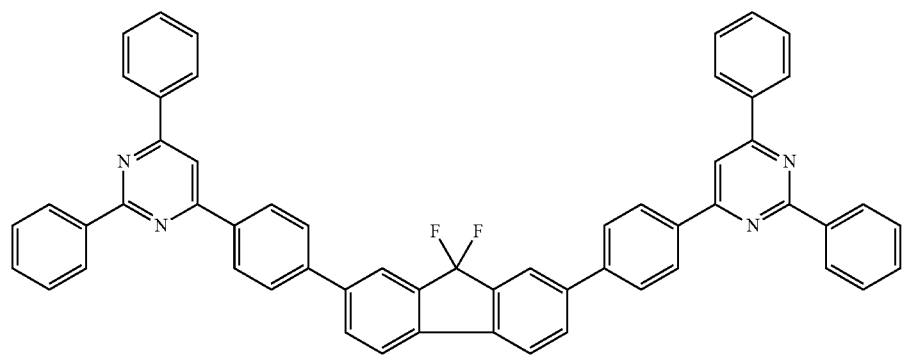
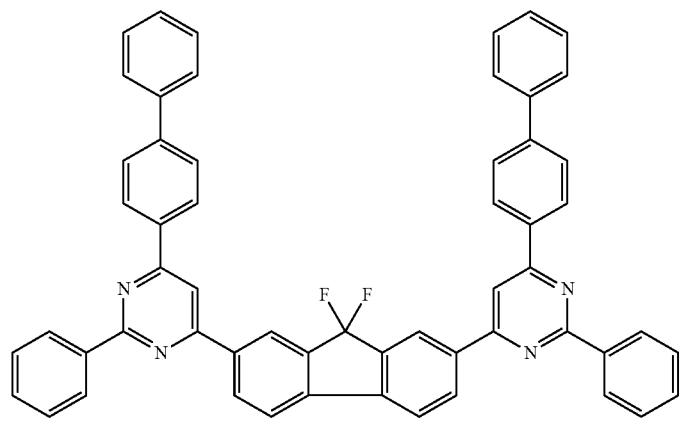
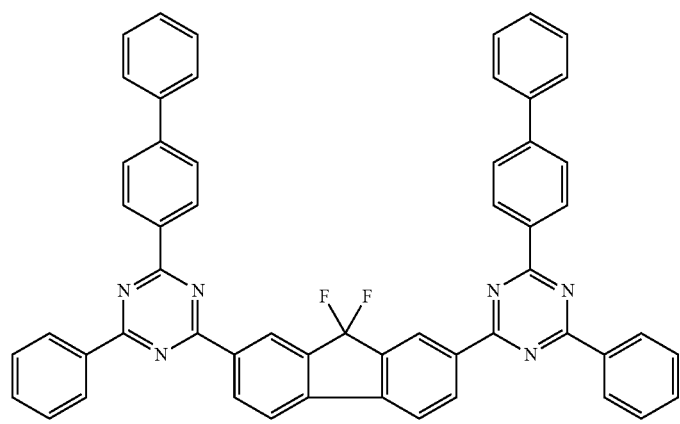
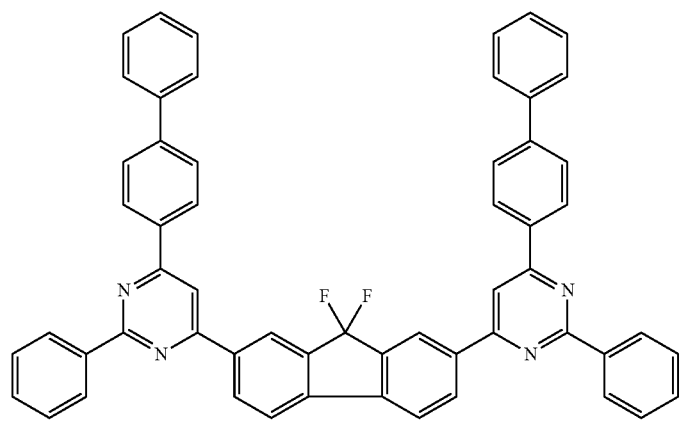

-continued
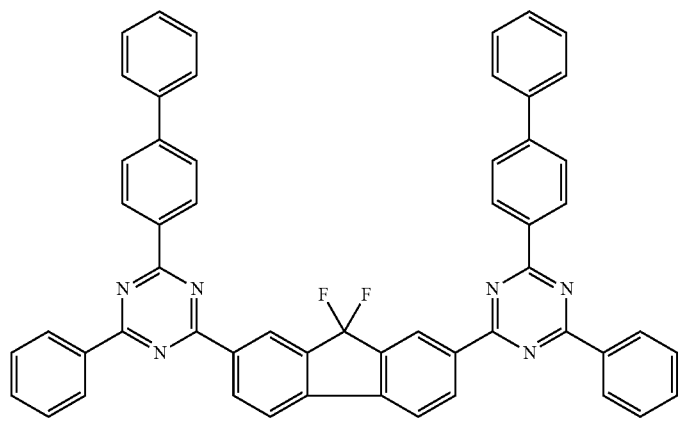
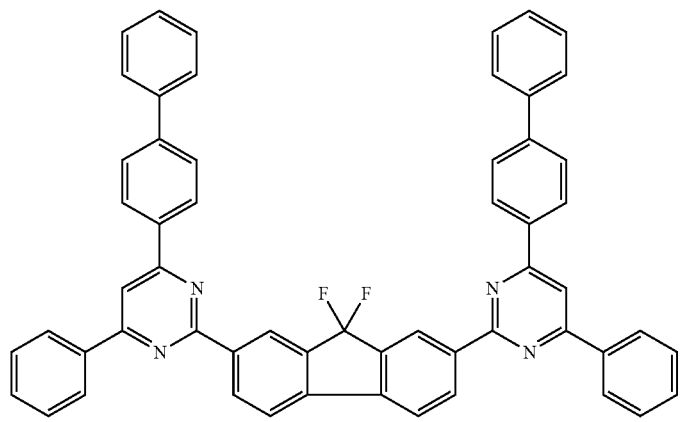
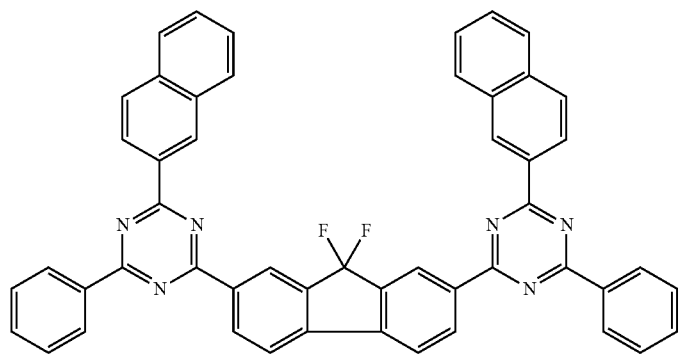
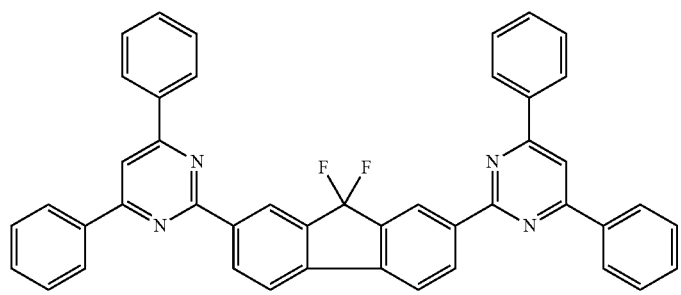

-continued
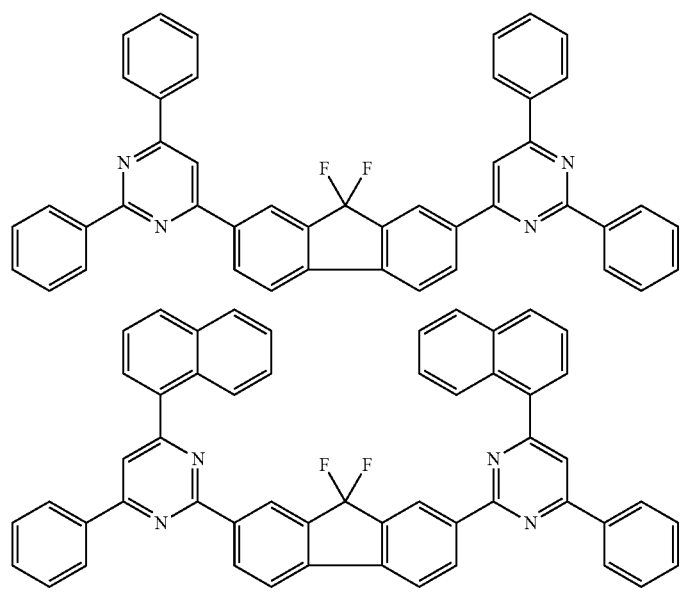
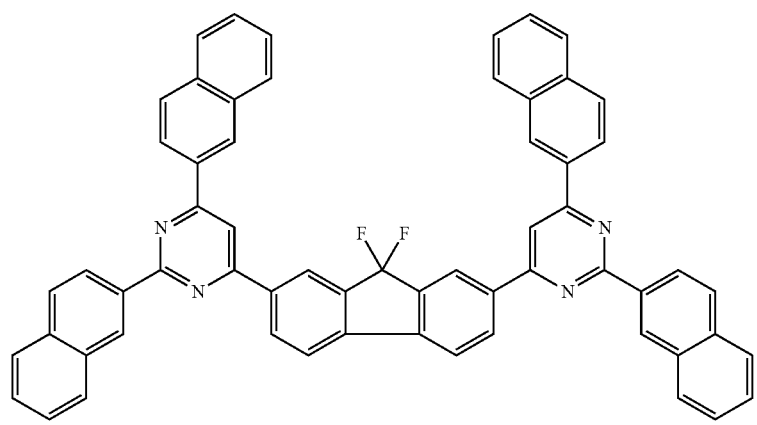
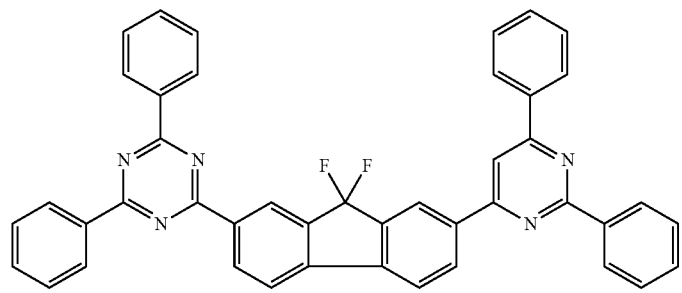
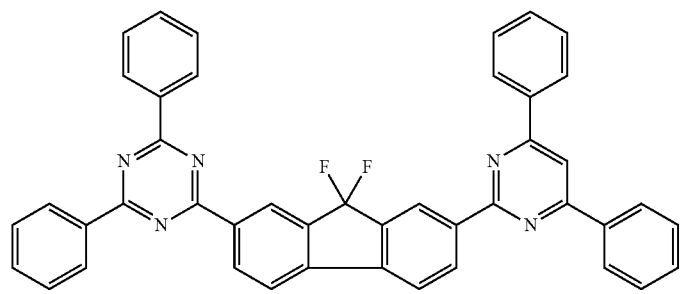

-continued
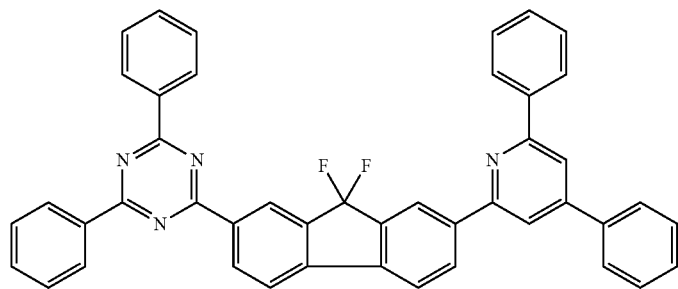
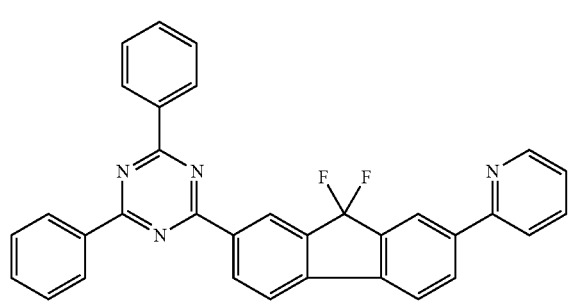
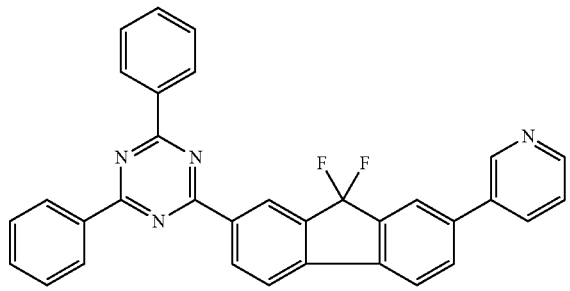
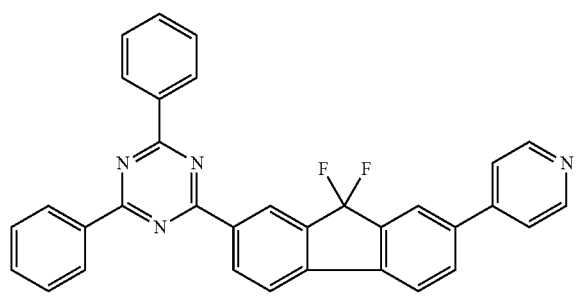
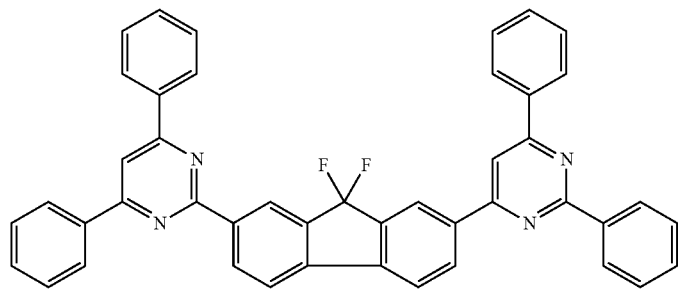
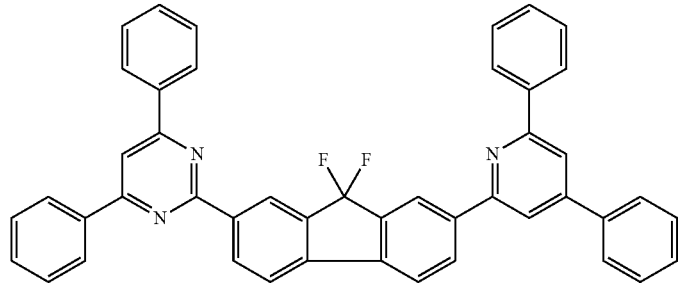

-continued
173
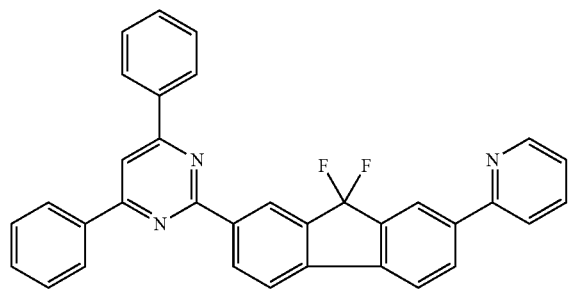
174
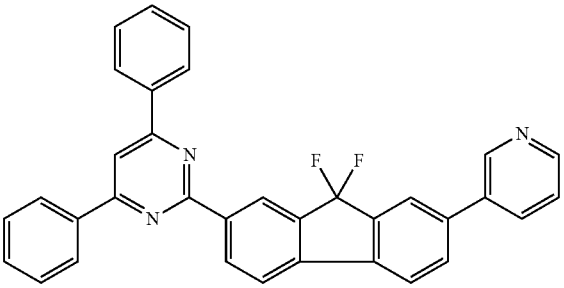
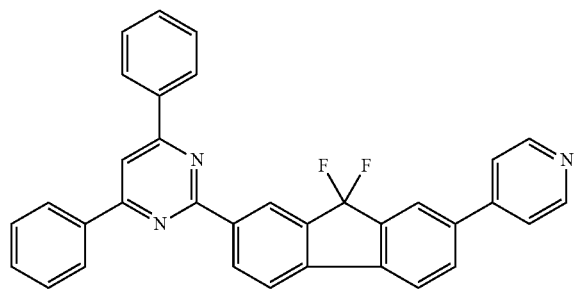
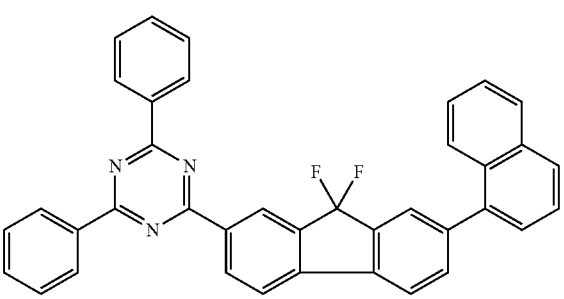
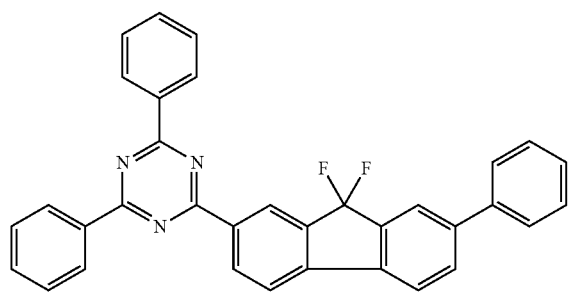
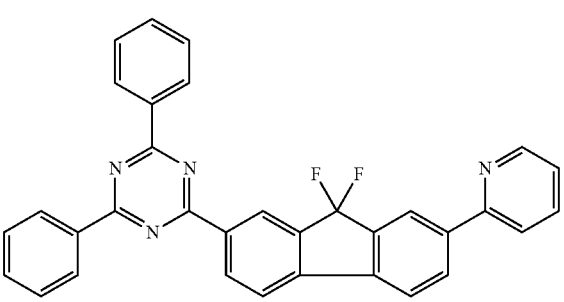
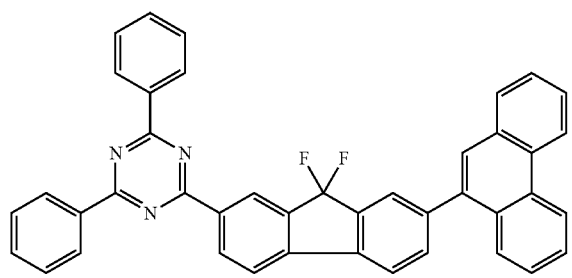
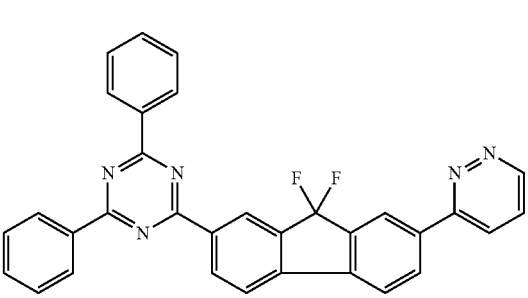
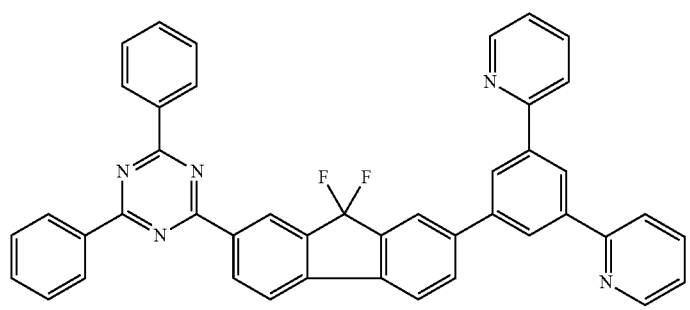

-continued
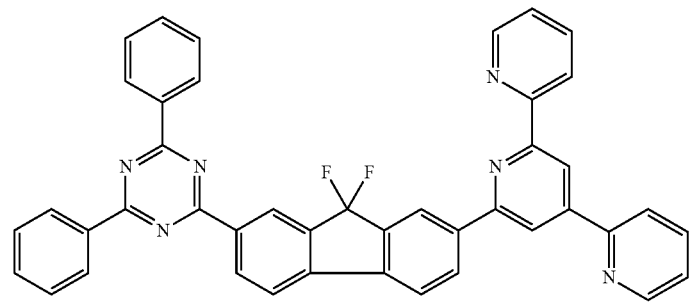
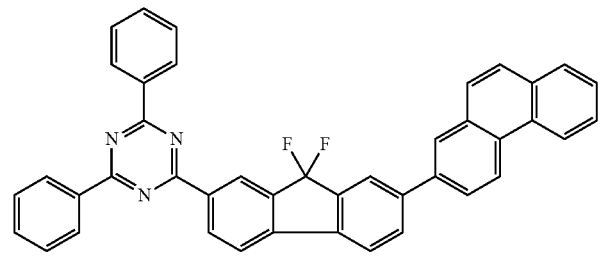
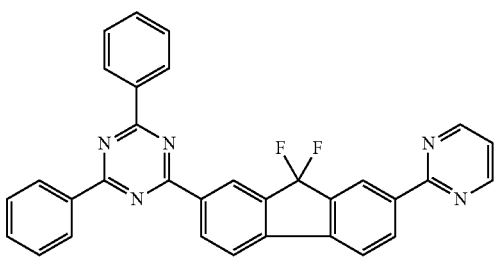
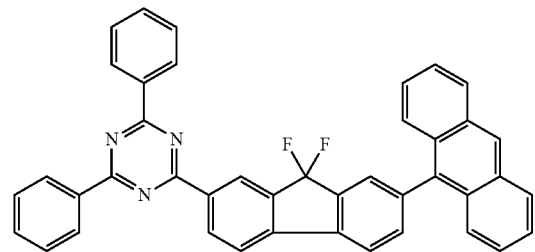
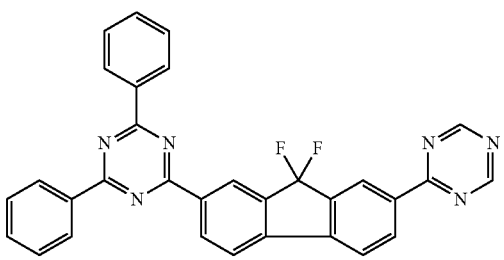
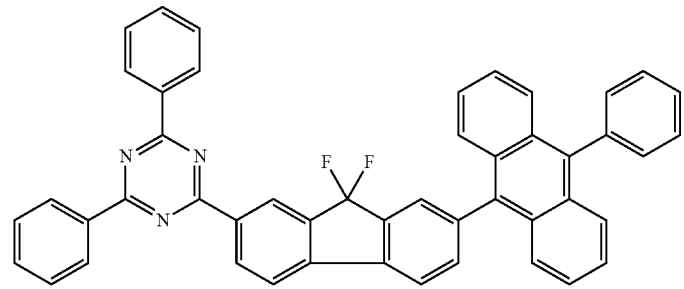
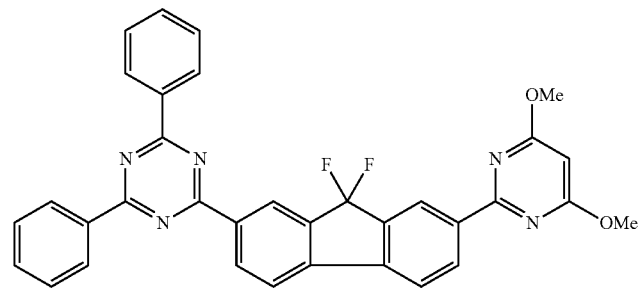
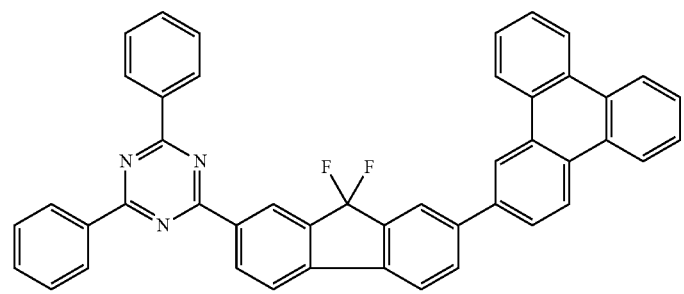

-continued
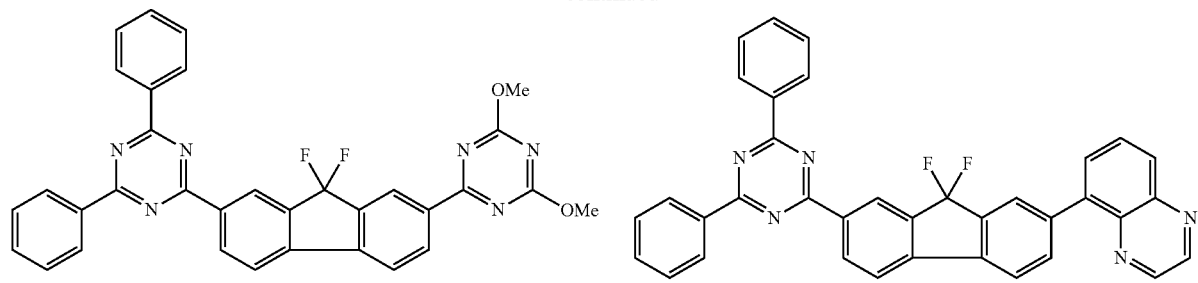
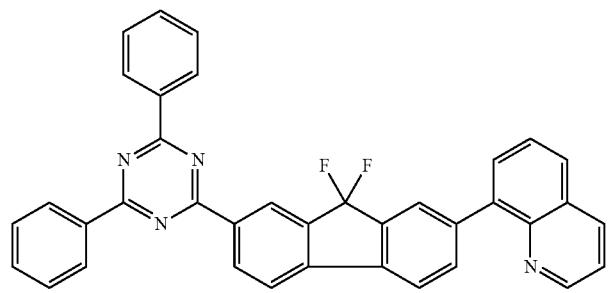
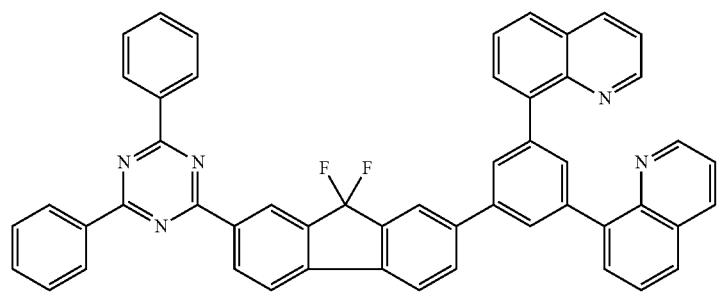
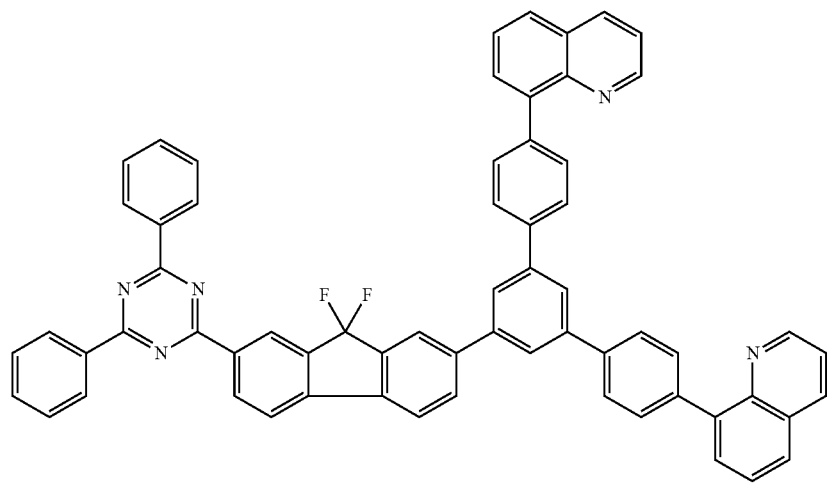

-continued
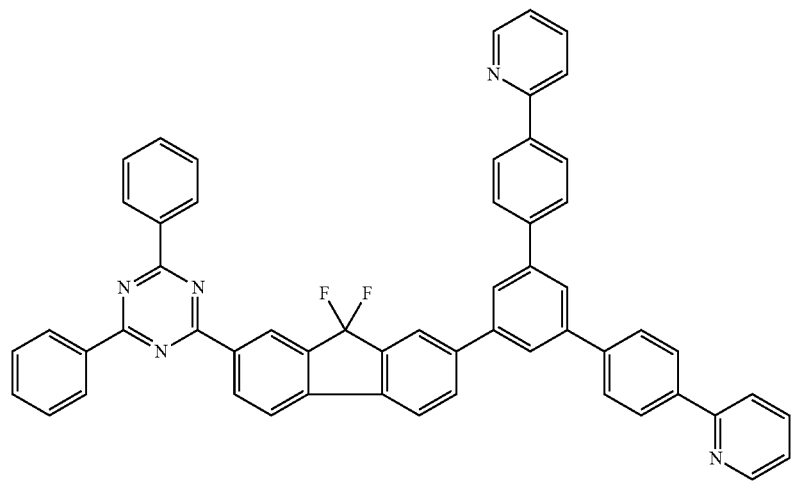
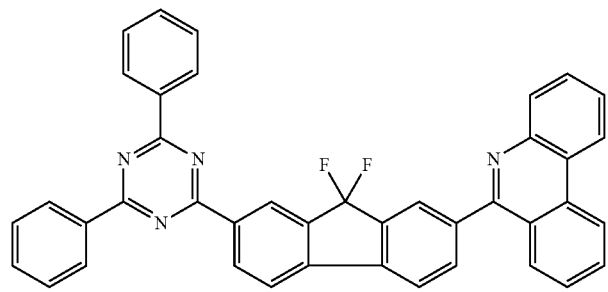
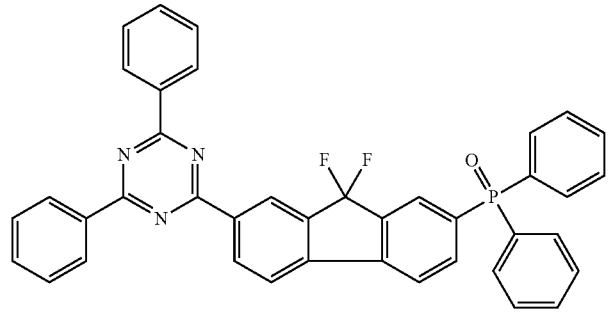
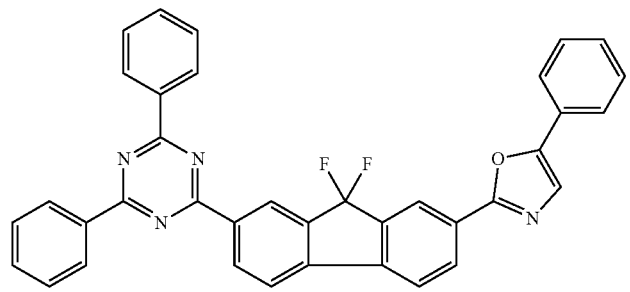
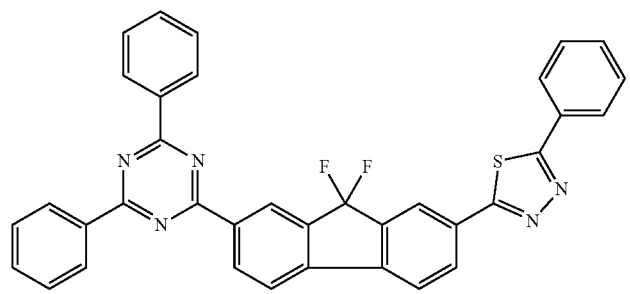

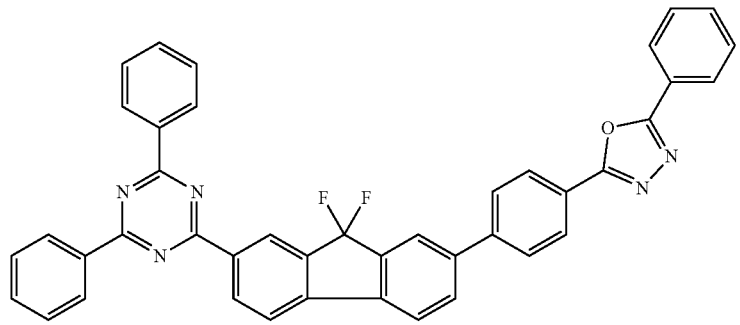
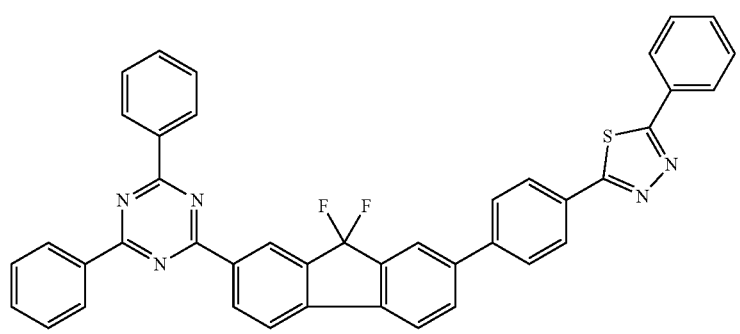
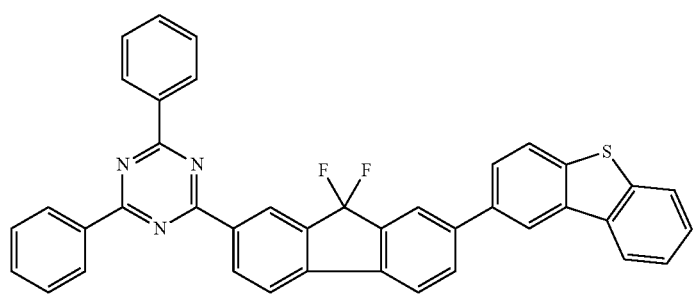
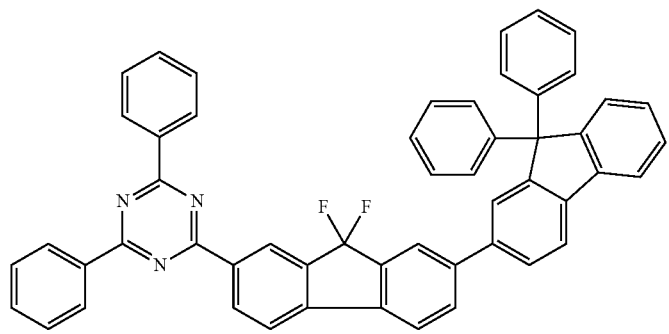
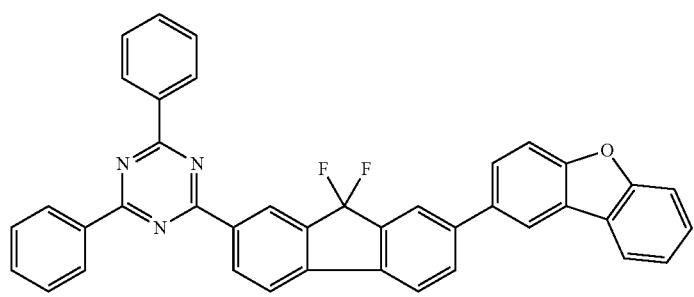

-continued
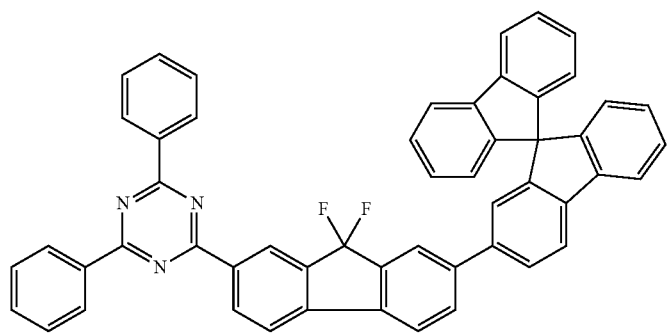
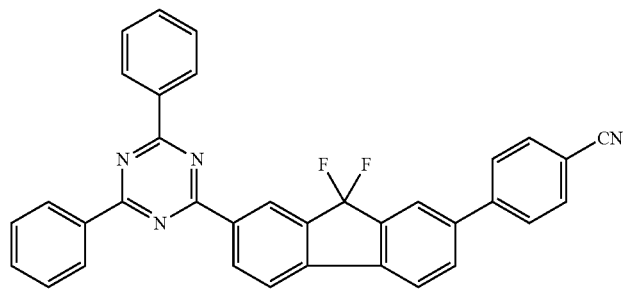
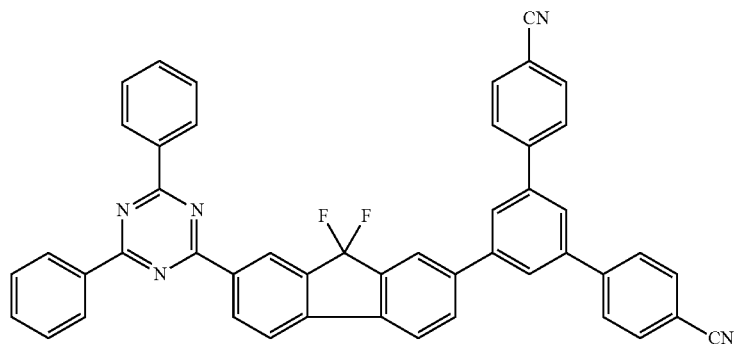
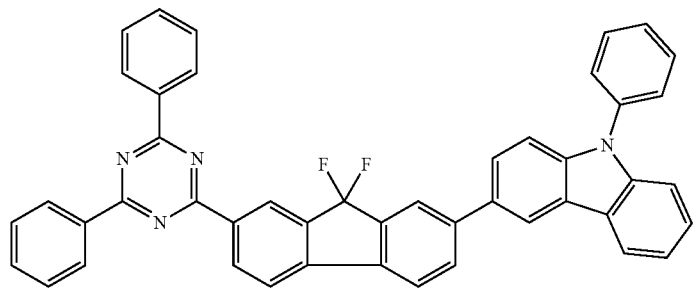
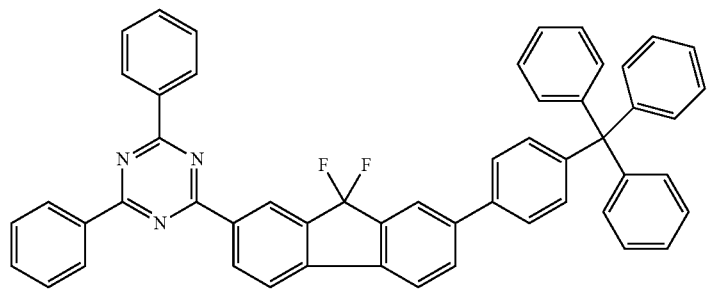

-continued
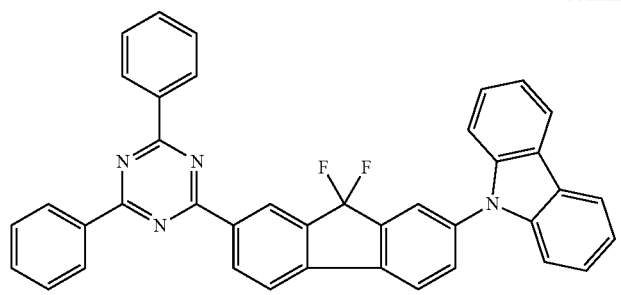
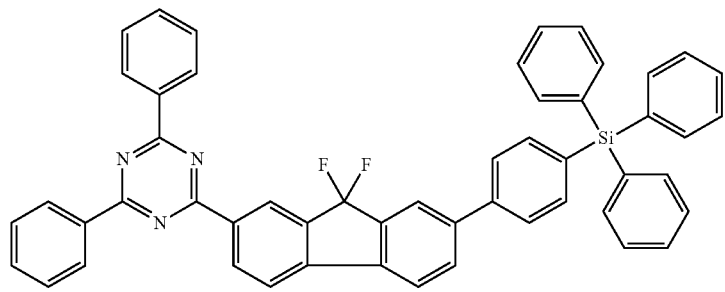
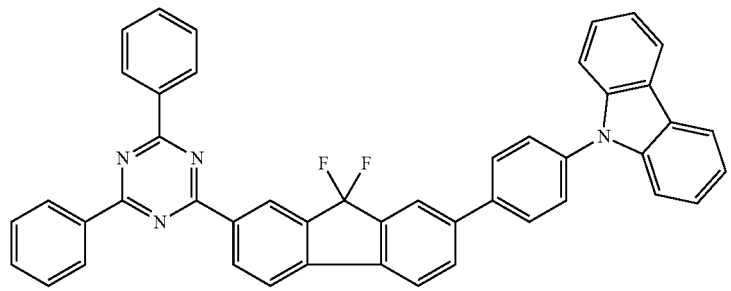
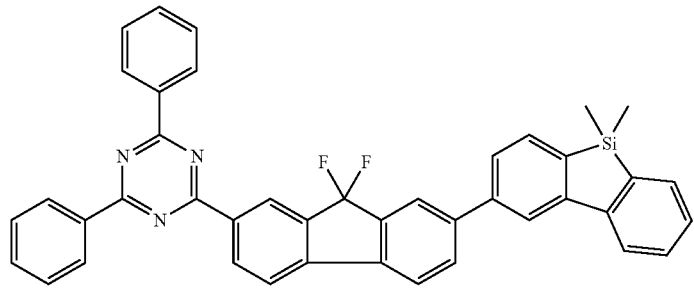
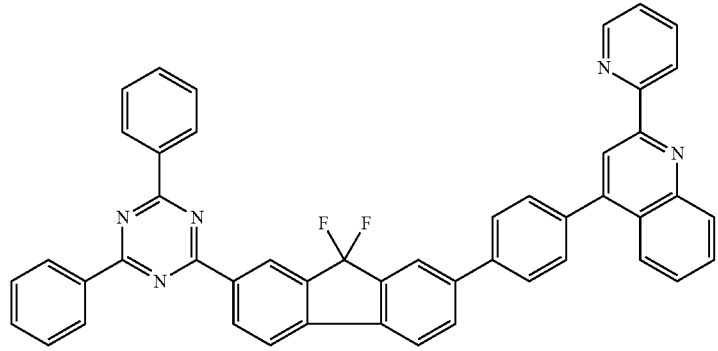

-continued

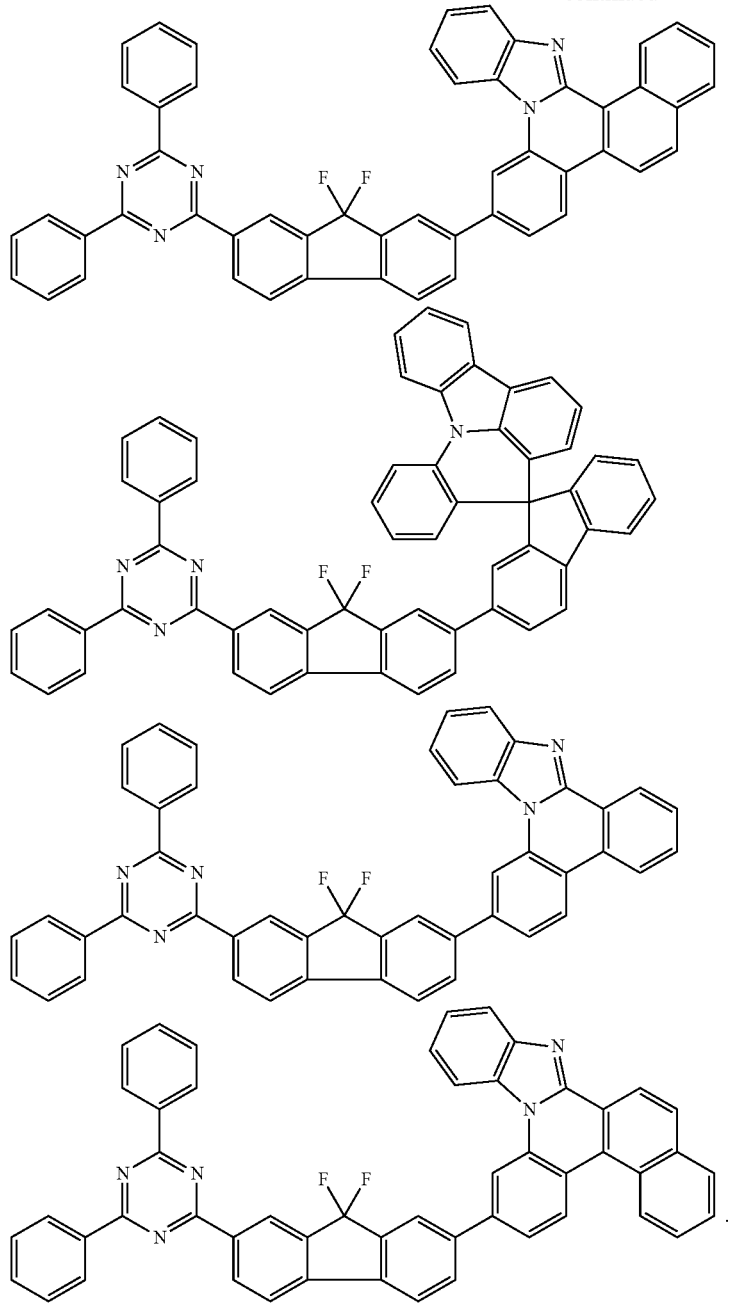

6. An organic light emitting device comprising:
a first electrode;
a second electrode; and
one or more organic material layers disposed between the first electrode and the second electrode,
wherein one or more layers of the organic material layers comprise the compound of claim 1.

7. The organic light emitting device of claim 6, wherein the organic material layer comprises at least one layer of an electron injection layer and an electron transfer layer, and one or more layers of the layers comprise the compound.

8. The organic light emitting device of claim 6, wherein the organic material layer comprises a light emitting layer, and the light emitting layer comprises the compound as a host of the light emitting layer.

9. The organic light emitting device of claim 6, wherein the organic material layer comprises one or more layers of a hole injection layer, a hole transfer layer, and a layer carrying out hole injection and hole transfer at the same time, and one or more layers of the layers comprise the compound.

10. The organic light emitting device of claim 6, wherein the organic material layer comprises the compound as a host, and comprises other organic compounds, metals or metal compounds as a dopant.

11. The organic light emitting device of claim 6, wherein the organic material layer comprises a light emitting layer, and the light emitting layer comprises a compound represented by the following Chemical Formula 17:

[Chemical Formula 17]

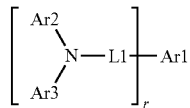

wherein, in Chemical Formula 17, r is an integer of 1 or greater;

Ar1 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group;

L1 is a direct bond; a substituted or unsubstituted arylene group; or a substituted or unsubstituted heteroarylene group;

Ar2 and Ar3 are the same as or different from each other, and each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or may bond to each other to form a substituted or unsubstituted ring; and when r is 2 or greater, the structures in the parentheses are the same as or different from each other.

12. The organic light emitting device of claim 11, wherein L1 is a direct bond, Ar1 is a substituted or unsubstituted divalent pyrene group, Ar2 and Ar3 are the same as or different from each other and each independently an aryl group, and r is 2.

* * * * *